United States Patent
Anazawa et al.

(10) Patent No.: US 11,543,355 B2
(45) Date of Patent: Jan. 3, 2023

(54) LIGHT-EMITTING DETECTION DEVICE

(71) Applicant: Hitachi High-Tech Corporation, Tokyo (JP)

(72) Inventors: Takashi Anazawa, Tokyo (JP); Motohiro Yamazaki, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 0 days.

(21) Appl. No.: 17/879,970

(22) Filed: Aug. 3, 2022

(65) Prior Publication Data

US 2022/0381694 A1 Dec. 1, 2022

Related U.S. Application Data

(63) Continuation of application No. 16/076,212, filed as application No. PCT/JP2016/055031 on Feb. 22, 2016, now Pat. No. 11,442,016.

(51) Int. Cl.
*G01N 21/64* (2006.01)
*G02B 3/00* (2006.01)
*G02B 27/14* (2006.01)
*C12Q 1/6869* (2018.01)
*B01L 3/00* (2006.01)

(52) U.S. Cl.
CPC .... *G01N 21/6452* (2013.01); *B01L 3/502715* (2013.01); *C12Q 1/6869* (2013.01); *G01N 21/64* (2013.01); *G02B 3/0056* (2013.01); *G02B 27/141* (2013.01); *G01N 2021/6421* (2013.01);
(Continued)

(58) Field of Classification Search
CPC . B01L 3/502715; C12Q 1/6869; G01N 21/64; G01N 21/6452; G01N 2021/6421; G01N 2021/6471; G01N 2021/6478; G02B 3/0056; G02B 27/141
See application file for complete search history.

(56) References Cited

U.S. PATENT DOCUMENTS

| 3,916,197 A | 10/1975 | Fulwyler |
| 5,312,535 A | 5/1994 | Waska et al. |

(Continued)

FOREIGN PATENT DOCUMENTS

| CN | 101995398 A | 3/2011 |
| DE | 10 2006 058 575 A1 | 6/2007 |

(Continued)

OTHER PUBLICATIONS

International Search Report (PCT/ISA/210) issued in PCT Application No. PCT/JP2016/055031 dated May 10, 2016 with English translation (four (4) pages).

(Continued)

*Primary Examiner* — Mark R Gaworecki
(74) *Attorney, Agent, or Firm* — Crowell & Moring LLP

(57) ABSTRACT

A light-emission detection apparatus is provided for individually condensing light emitted from each emission point of an emission-point array using each condensing lens of a condensing-lens array to forma light beam and detecting each light beam incident on a sensor in parallel. The light-emission detection apparatus can be downsized and high sensitivity and low crosstalk can be simultaneously accomplished when a certain relation between the diameter of each emission point, a focal length of each condensing lens, an interval of condensing lenses, and an optical path length between each condensing lens and a sensor is satisfied.

14 Claims, 28 Drawing Sheets

(52) U.S. Cl.
CPC ............... *G01N 2021/6471* (2013.01); *G01N 2021/6478* (2013.01)

(56) References Cited

U.S. PATENT DOCUMENTS

| | | | |
|---|---|---|---|
| 5,324,401 | A | 6/1994 | Yeung et al. |
| 5,582,705 | A | 12/1996 | Yeung et al. |
| 5,790,727 | A | 8/1998 | Dhadwal et al. |
| 6,191,425 | B1 | 2/2001 | Imai |
| 6,438,279 | B1 | 8/2002 | Craighead et al. |
| 6,461,492 | B1 | 10/2002 | Hayashizaki et al. |
| 6,531,044 | B1 | 3/2003 | Anazawa et al. |
| 7,029,628 | B2 | 4/2006 | Tam et al. |
| 2002/0117398 | A1 | 8/2002 | Hayashizaki et al. |
| 2003/0116436 | A1 | 6/2003 | Amirkhanian et al. |
| 2004/0003997 | A1 | 1/2004 | Anazawa et al. |
| 2007/0131870 | A1 | 6/2007 | Pang et al. |
| 2007/0158195 | A1 | 7/2007 | Inaba et al. |
| 2009/0128807 | A1 | 5/2009 | Sonehara et al. |
| 2010/0038522 | A1 | 2/2010 | Kamei et al. |
| 2011/0036992 | A1 | 2/2011 | Fukumoto et al. |

FOREIGN PATENT DOCUMENTS

| | | | |
|---|---|---|---|
| EP | 1 932 594 A1 | 6/2008 | |
| JP | 2000-321243 A | 11/2000 | |
| JP | 2001-124736 A | 5/2001 | |
| JP | 2001-264293 A | 9/2001 | |
| JP | 2006-292369 A | 10/2006 | |
| JP | 2007-171214 A | 7/2007 | |
| JP | 2007-285999 A | 11/2007 | |
| JP | 2009-145320 A | 7/2009 | |
| JP | 2009-300385 A | 12/2009 | |
| JP | 2011-59095 A | 3/2011 | |
| WO | WO 2004/017061 A1 | 2/2004 | |
| WO | WO 2015/132347 A1 | 9/2015 | |

OTHER PUBLICATIONS

Japanese-language Written Opinion (PCT/ISA/237) issued in PCT Application No. PCT/JP2016/055031 dated May 10, 2016 (four (4) pages).
Haga T. et al., "Simultaneous Four-Color Imaging of Single Molecule Fluorophores Using Dichroic Mirrors and Four Charge-Coupled Devices," Feb. 4, 2011, vol. 82(2), Review of Scientific Instruments, 023701, American Institute of Physics, United States, (seven (7) pages).
German-language Office Action issued in German Application No. 112016006197.8 dated Apr. 6, 2020 (six (6) pages).
Japanese-language Office Action issued in Japanese Application No. 2018-501420 dated Jul. 7, 2020 (four (4) pages).
Chinese-language Office Action issued in Chinese Application No. 201680081287.2 dated Dec. 11, 2020 (8 pages).

[FIG. 1]
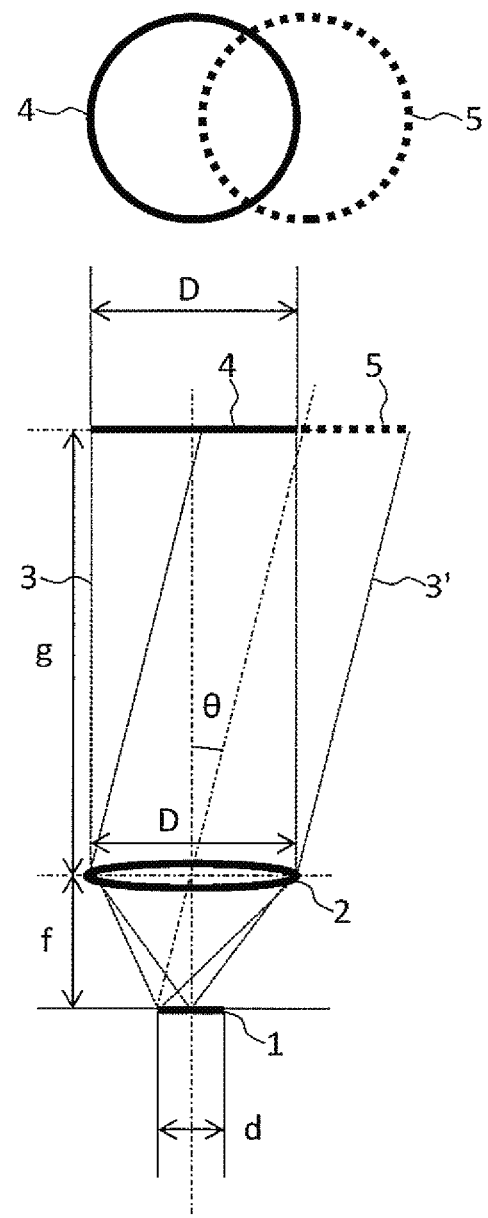

[FIG. 2]
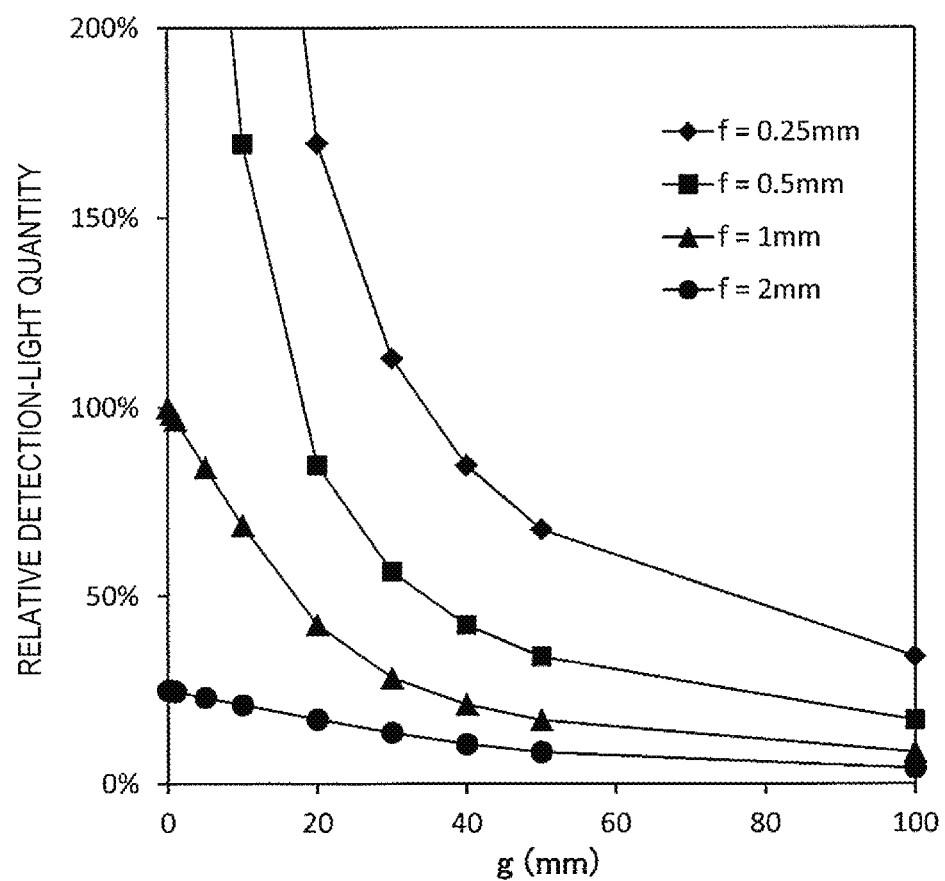

[FIG. 3]
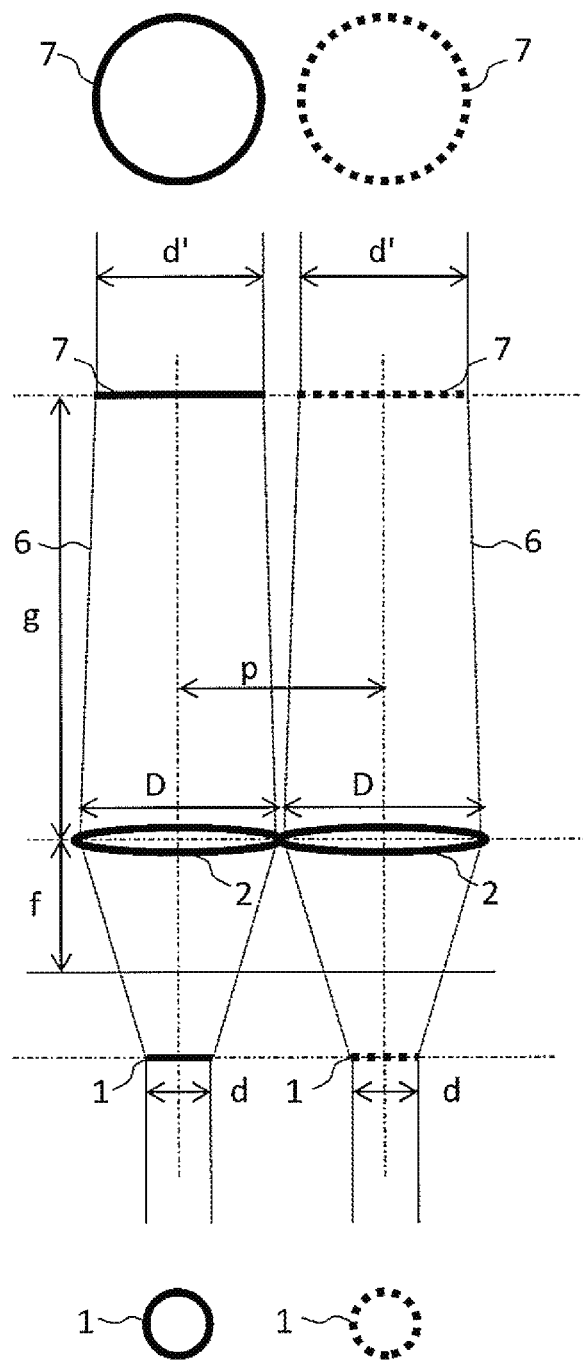

[FIG. 4]
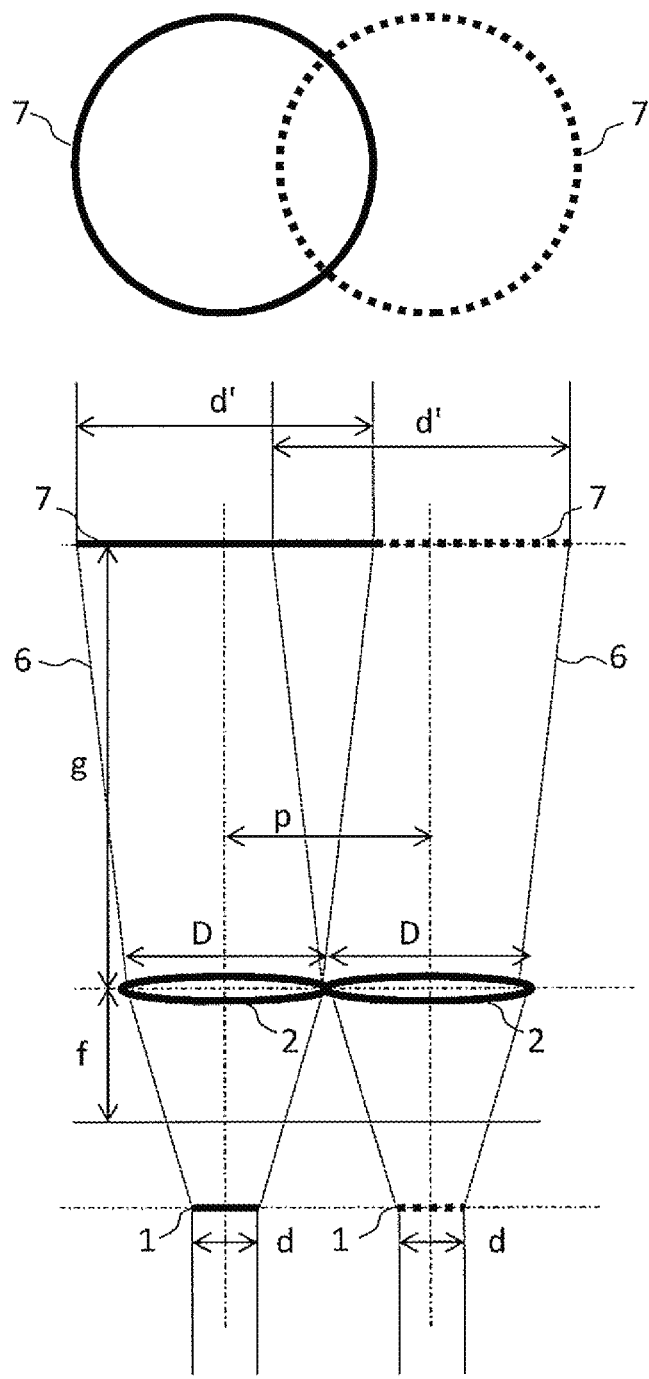

[FIG. 5]
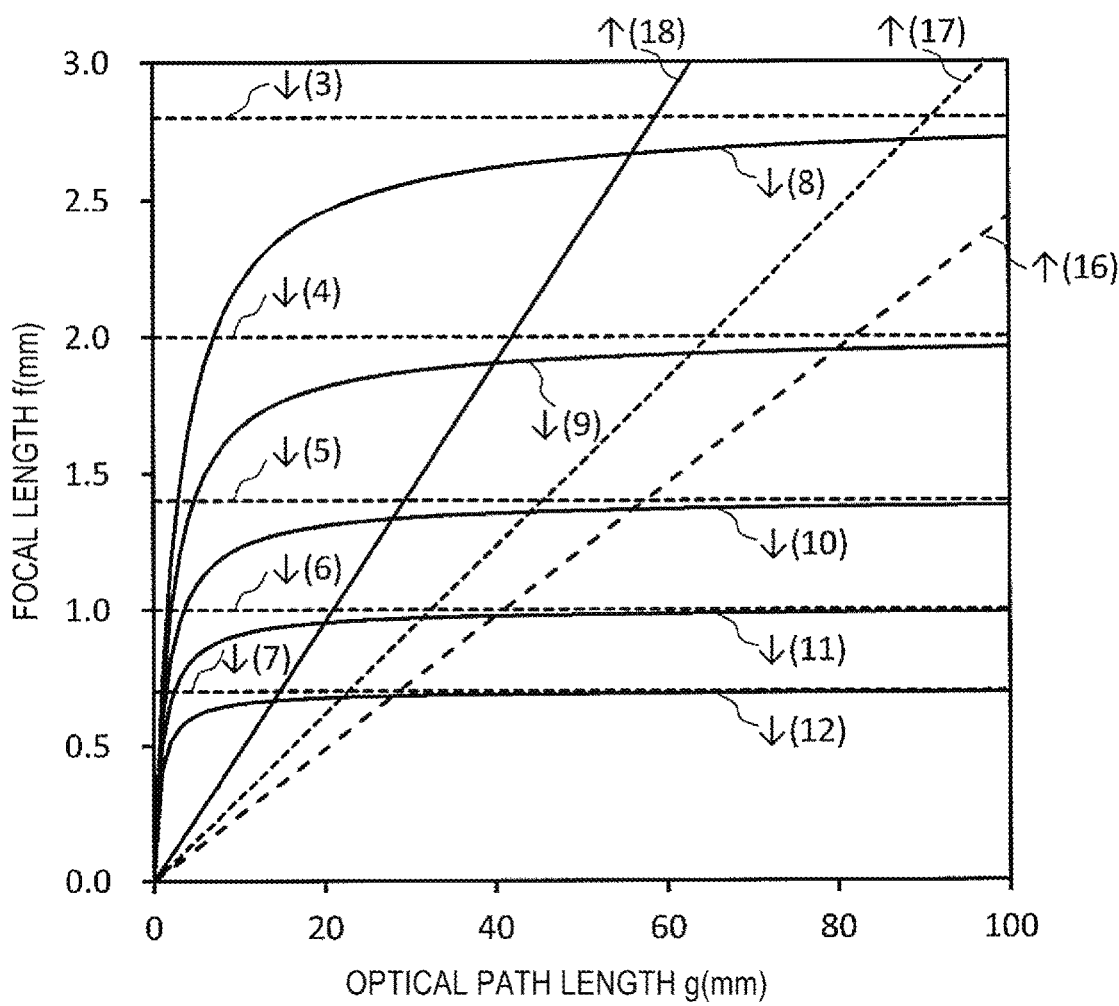

[FIG. 6A]
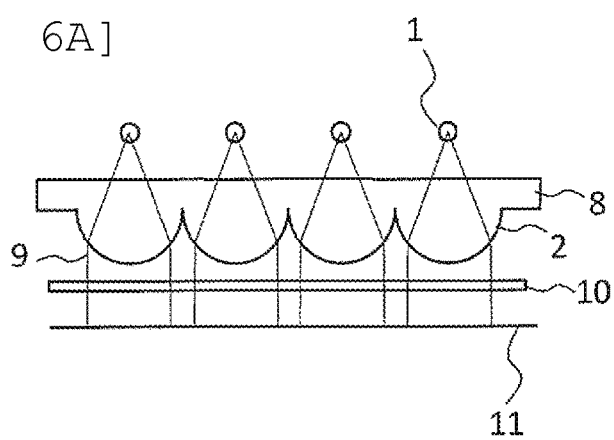
[FIG. 6B]
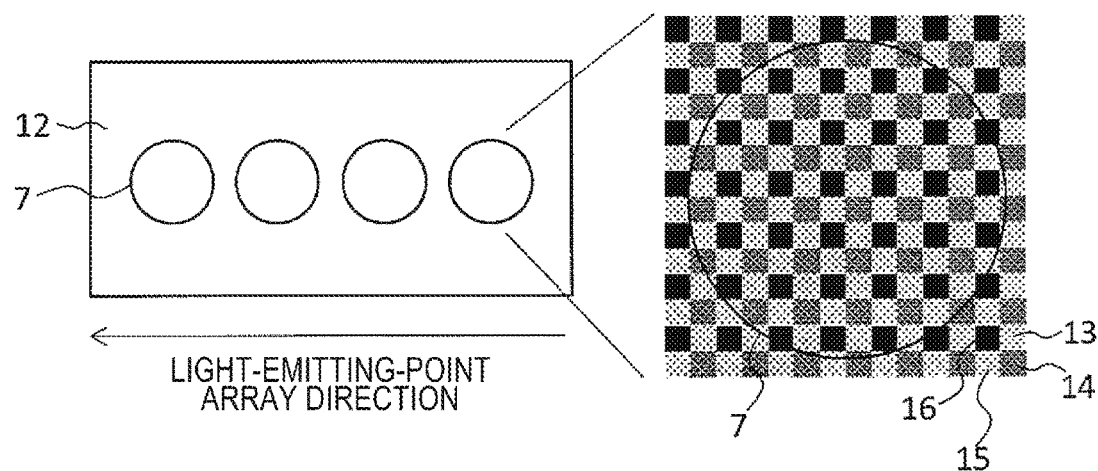
LIGHT-EMITTING-POINT ARRAY DIRECTION

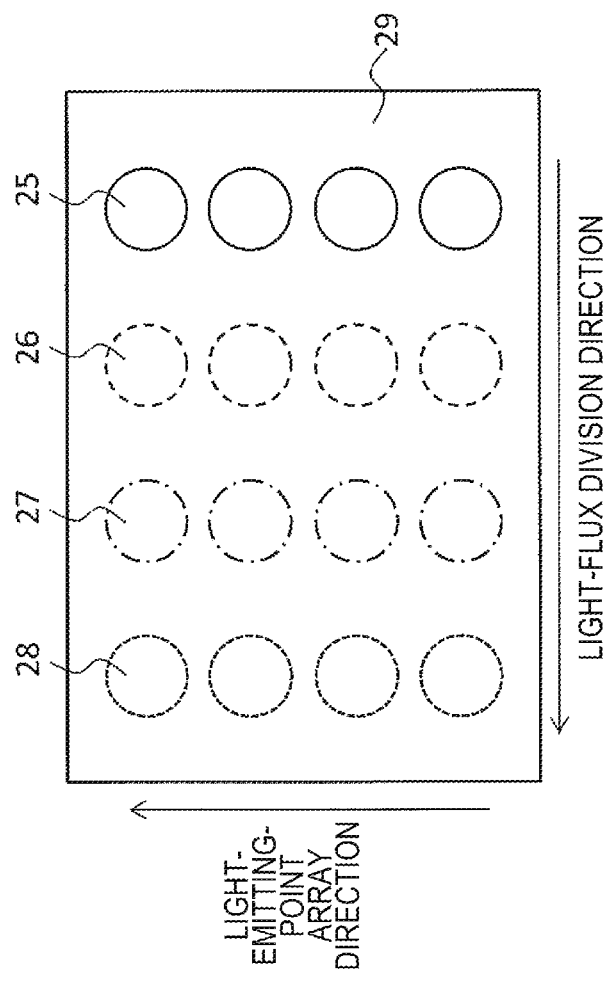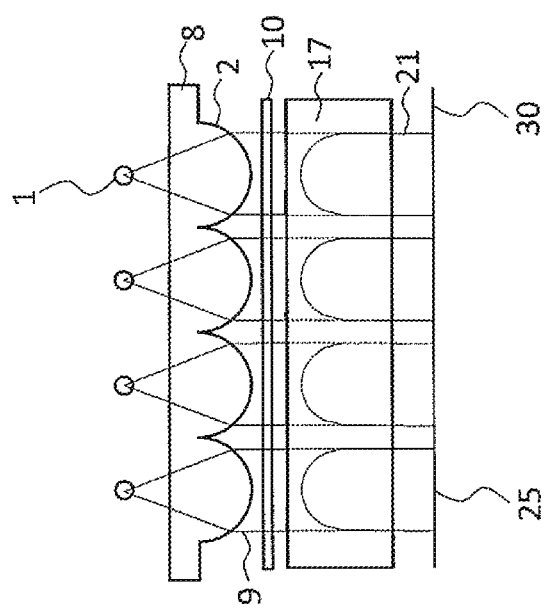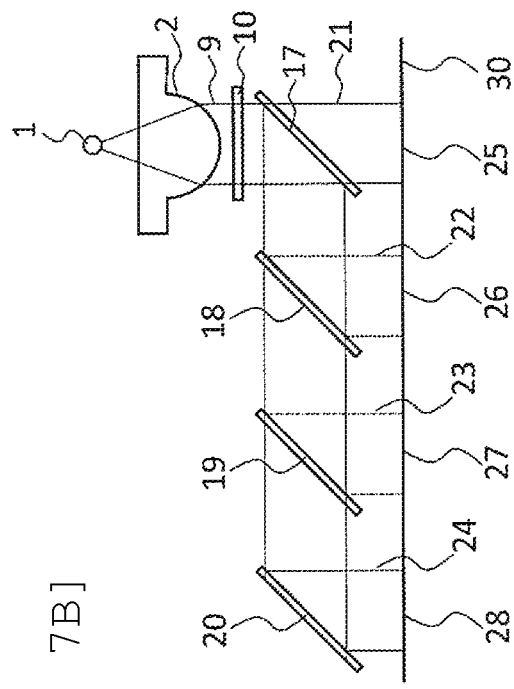

[FIG. 8A]
[FIG. 8B]
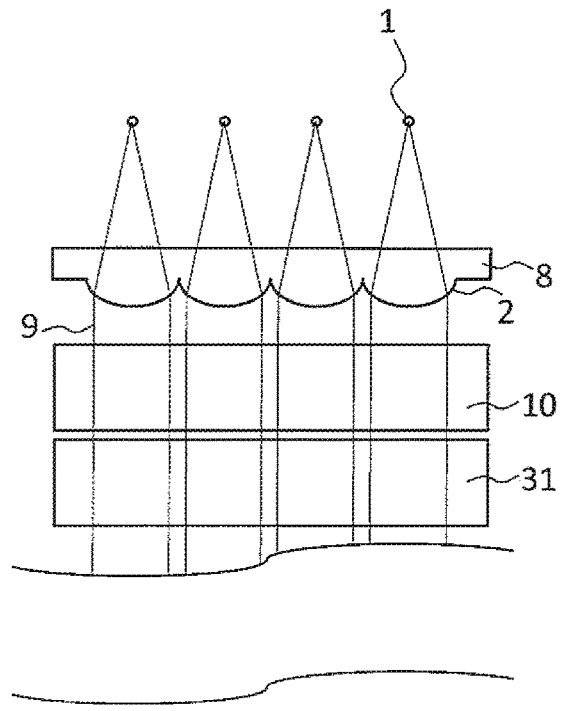
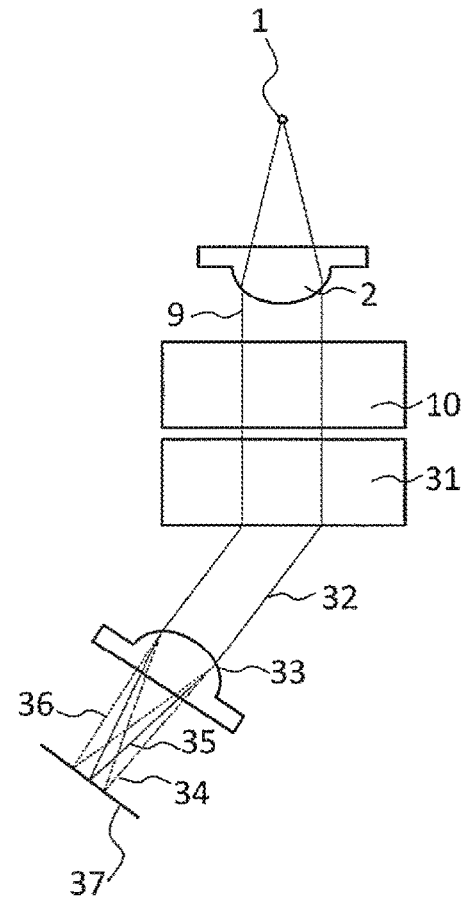
[FIG. 8C]
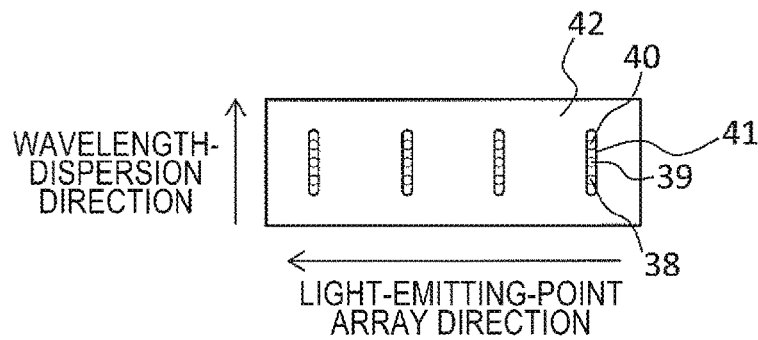
WAVELENGTH-
DISPERSION
DIRECTION
← LIGHT-EMITTING-POINT
ARRAY DIRECTION

[FIG. 9A]
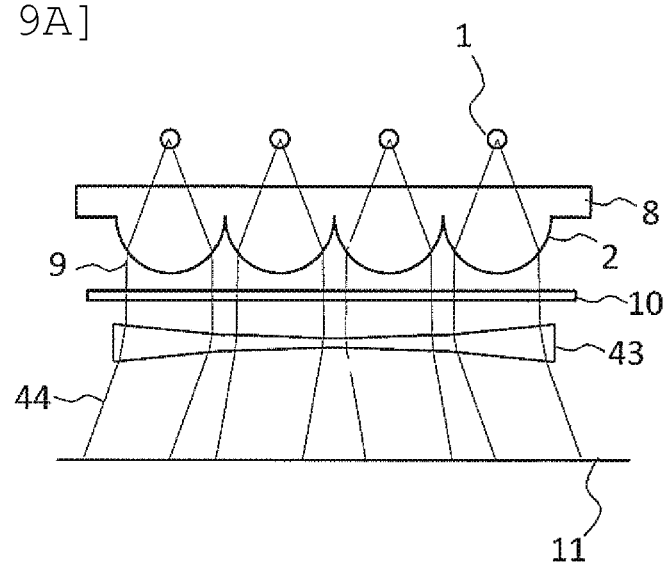
[FIG. 9B]
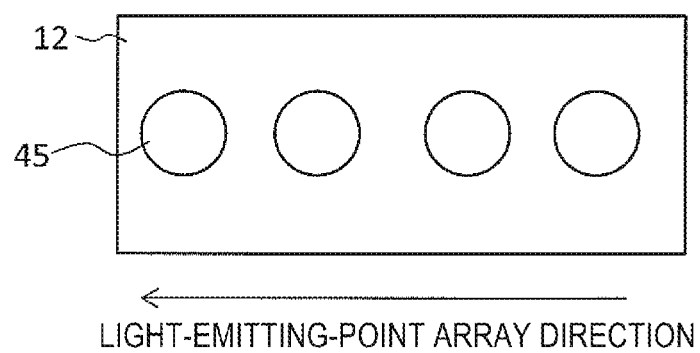
LIGHT-EMITTING-POINT ARRAY DIRECTION

[FIG. 10A]
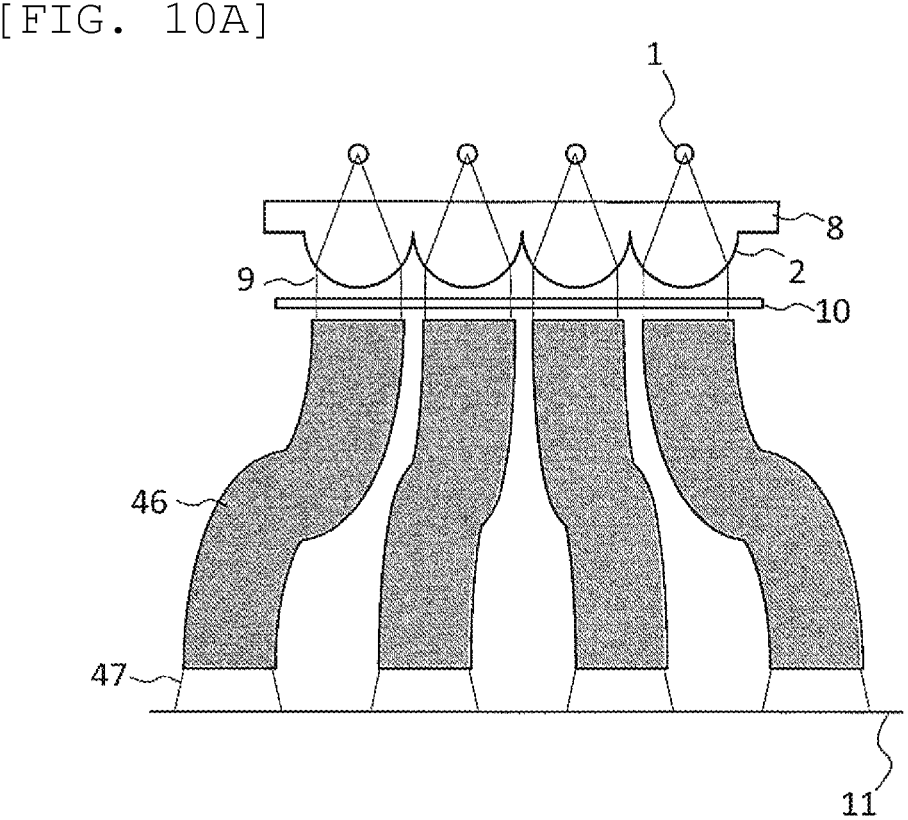
[FIG. 10B]
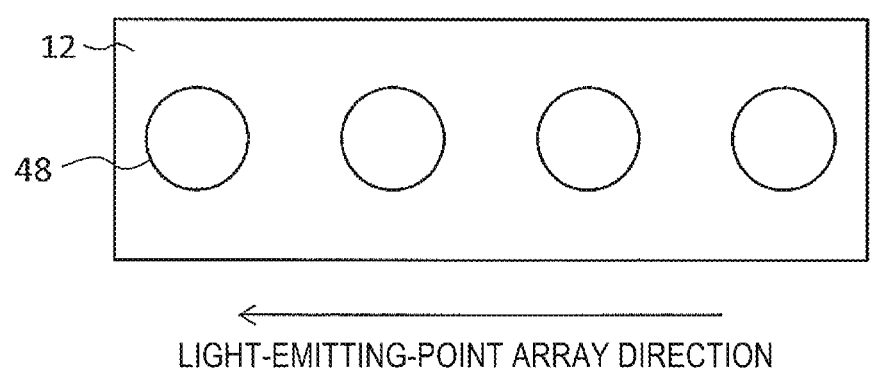
LIGHT-EMITTING-POINT ARRAY DIRECTION

[FIG. 11]
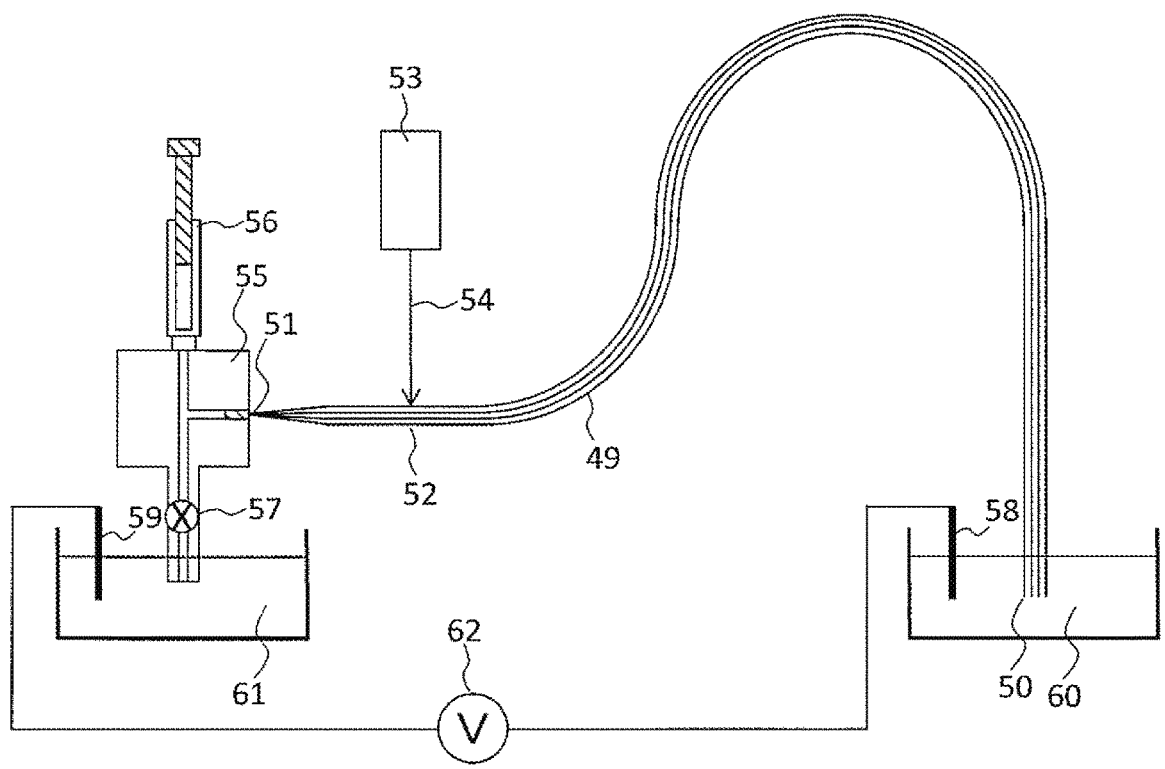

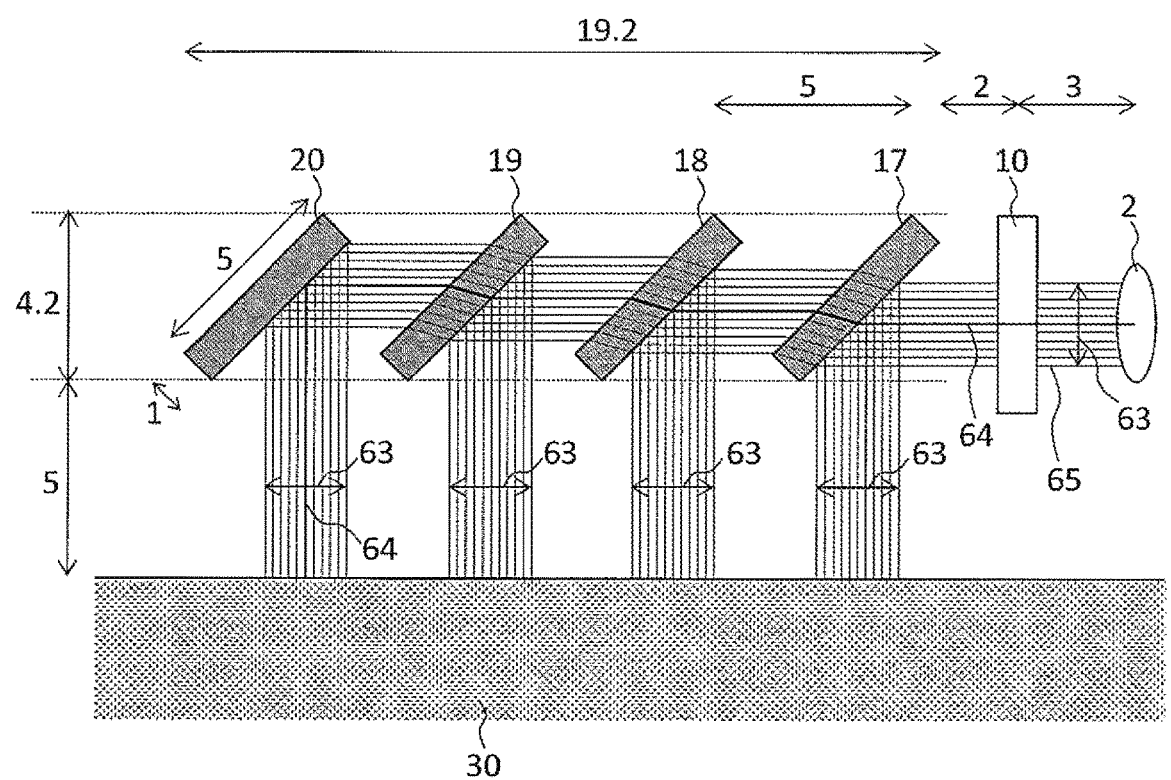
[FIG. 12]

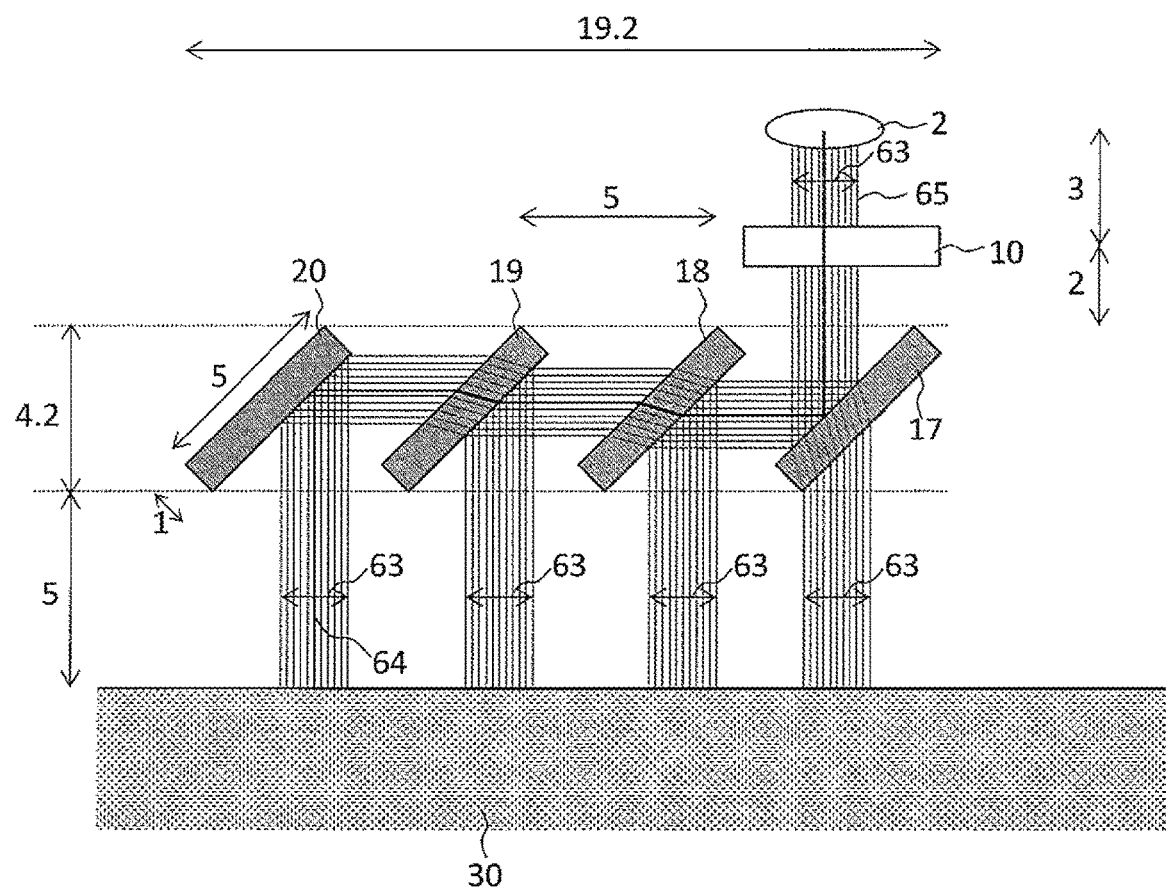
[FIG. 13]

[FIG. 14]
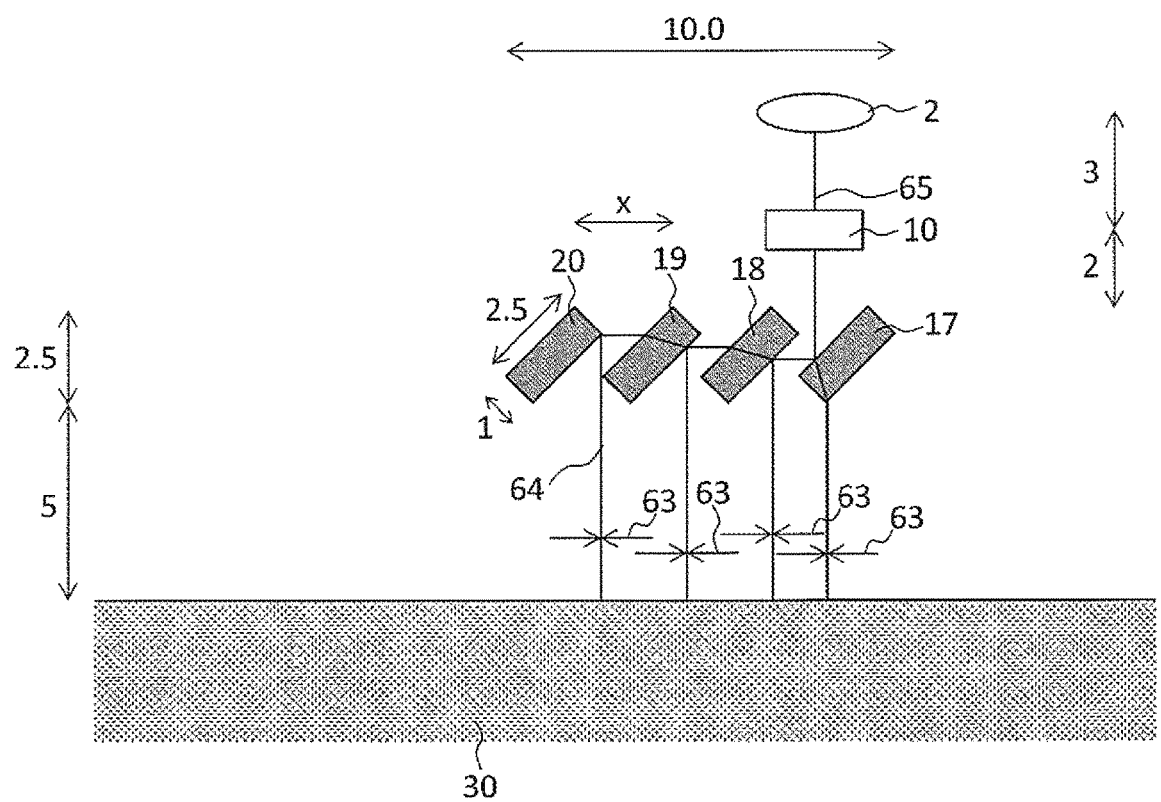

[FIG. 15]
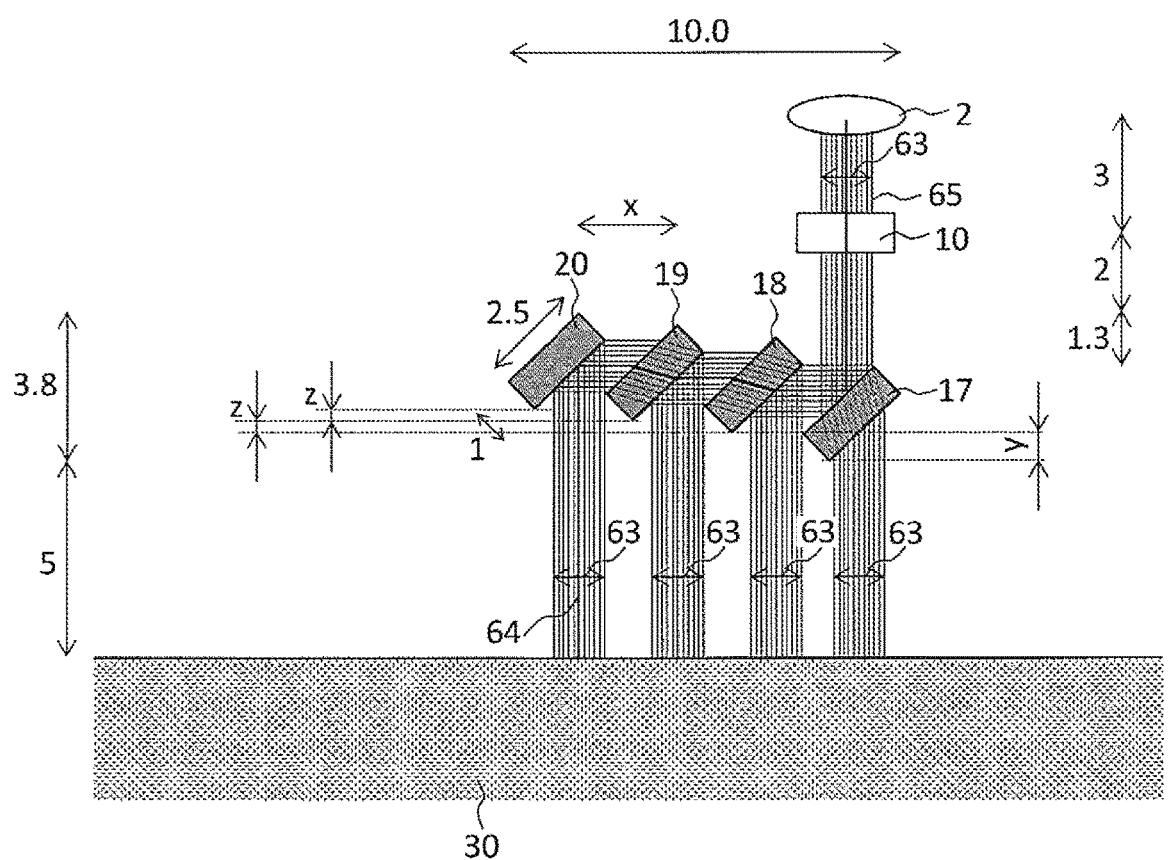

[FIG. 16]
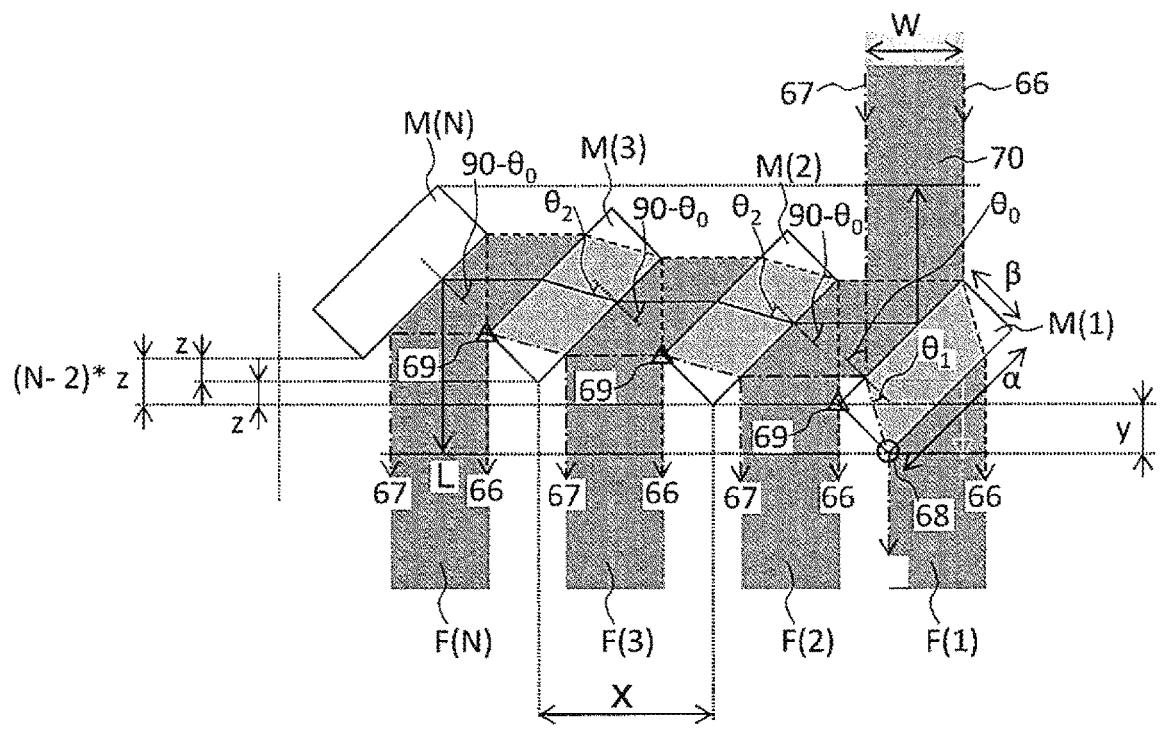

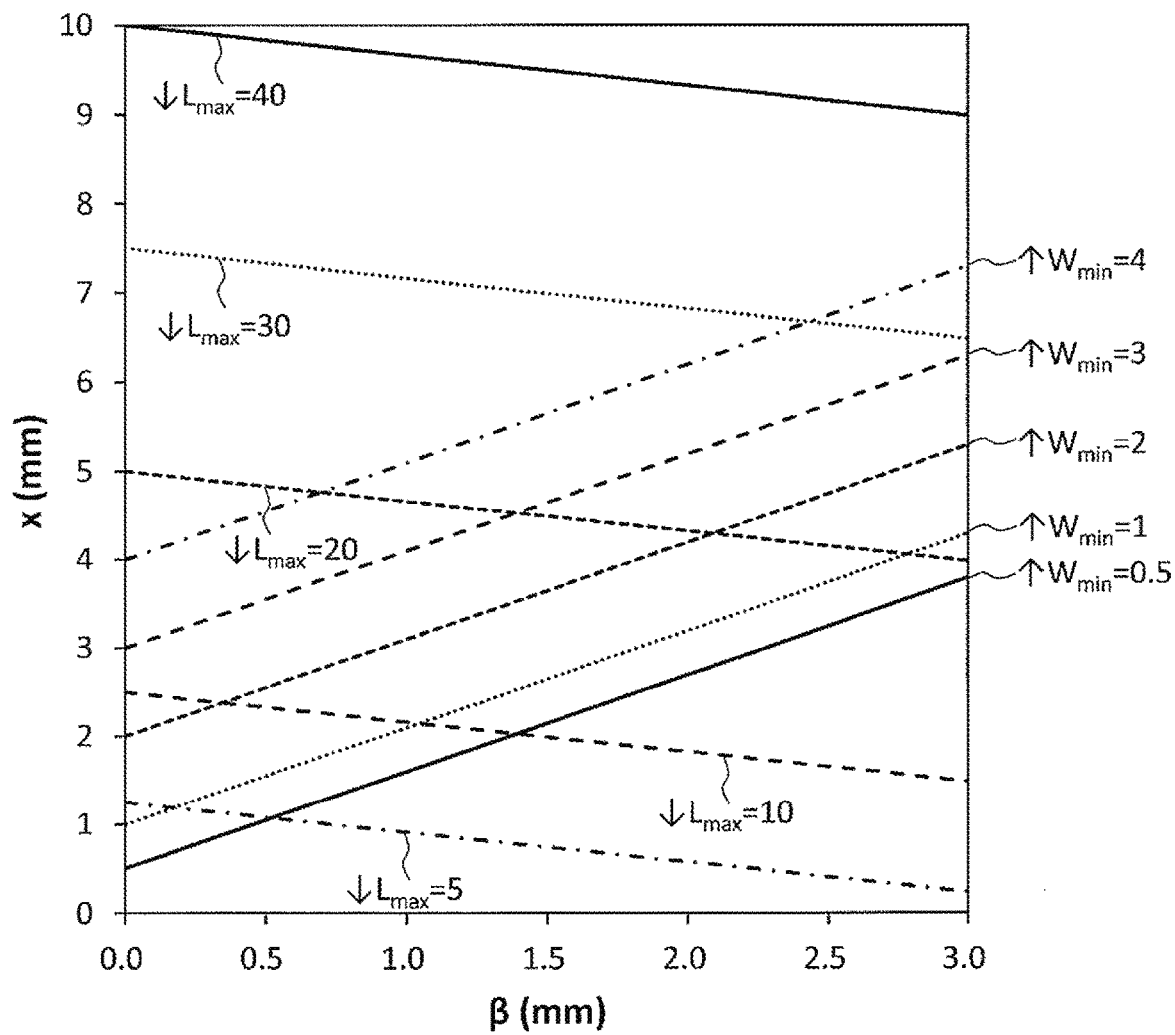
[FIG. 17]

[FIG. 18]
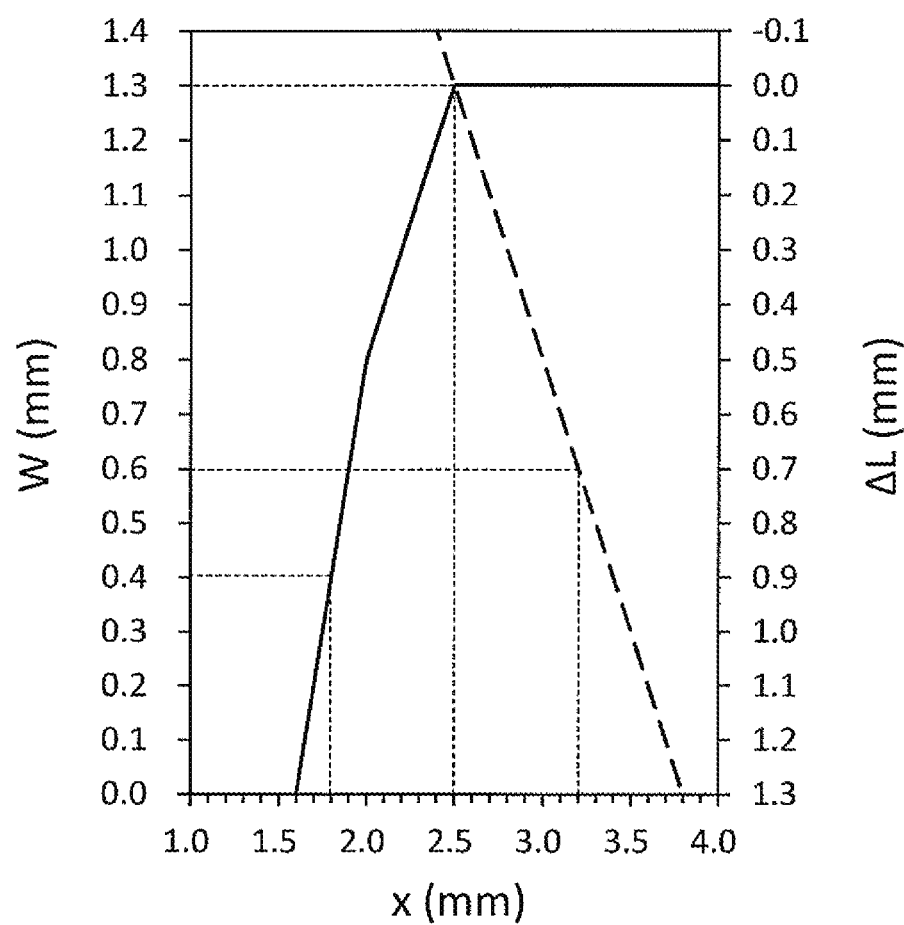

[FIG. 19A]
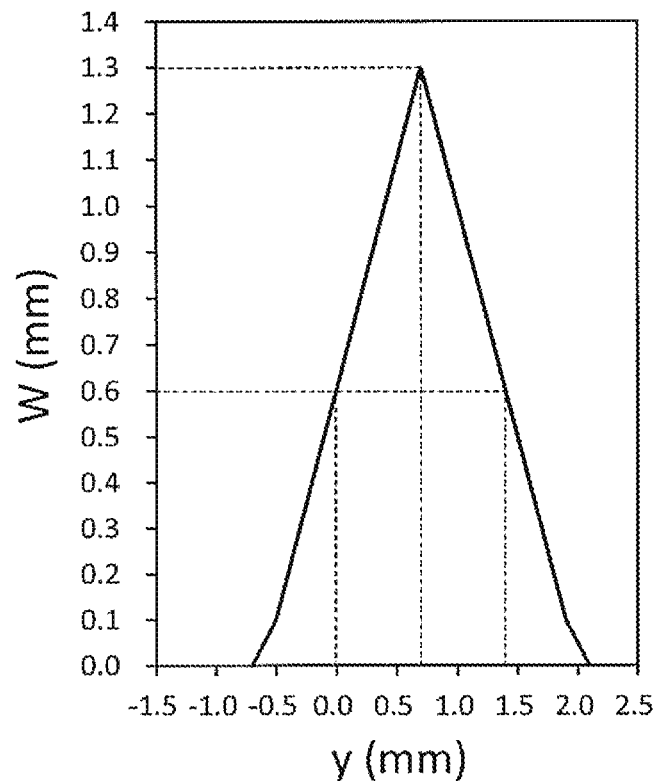
[FIG. 19B]
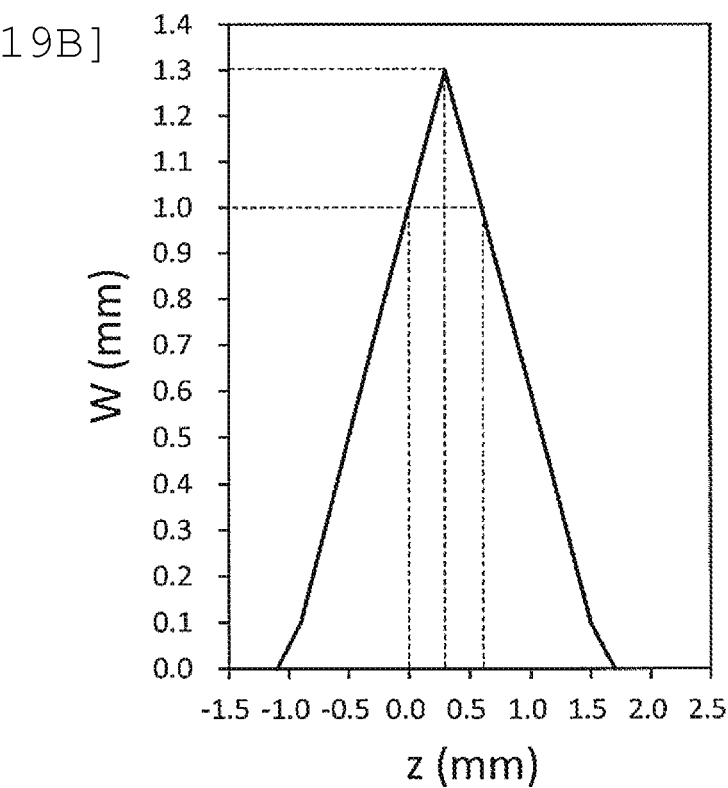

[FIG. 20]
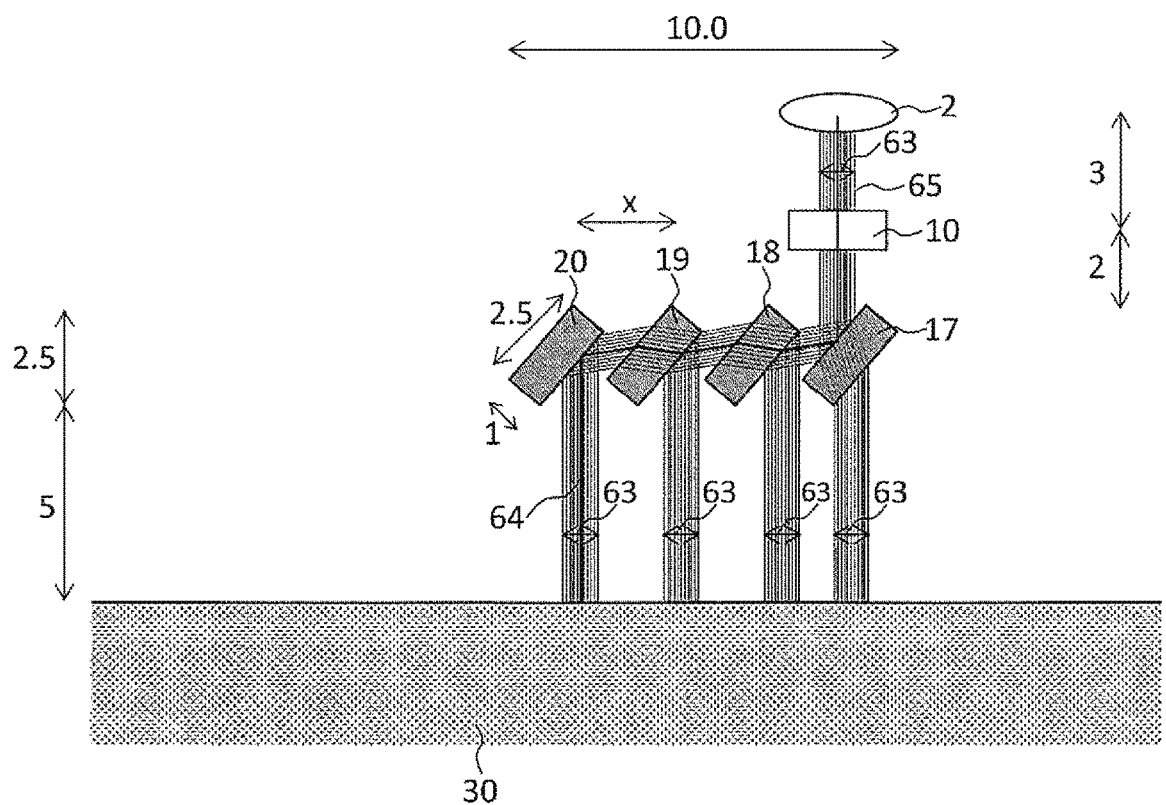

[FIG. 21]
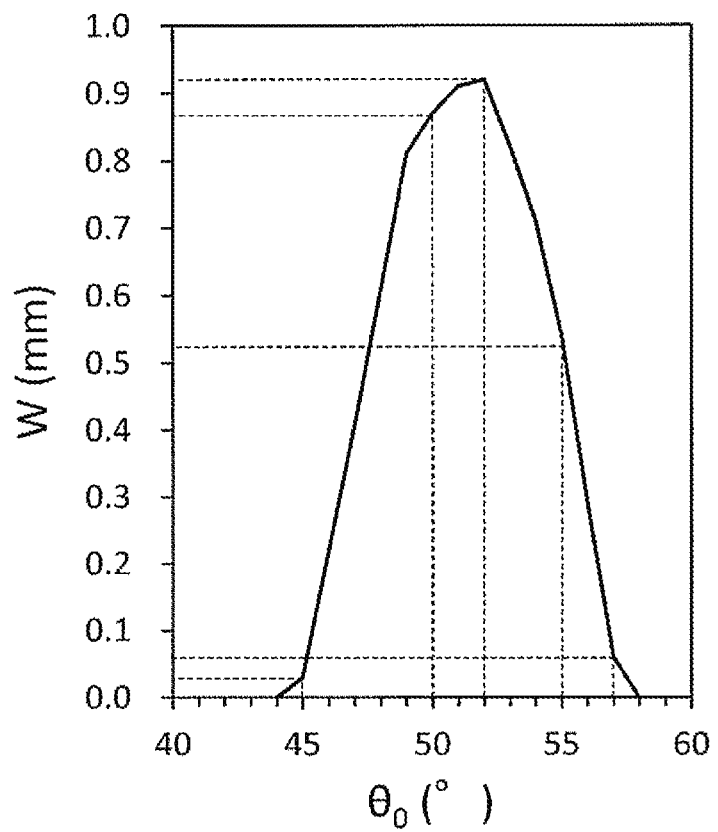

[FIG. 22A]
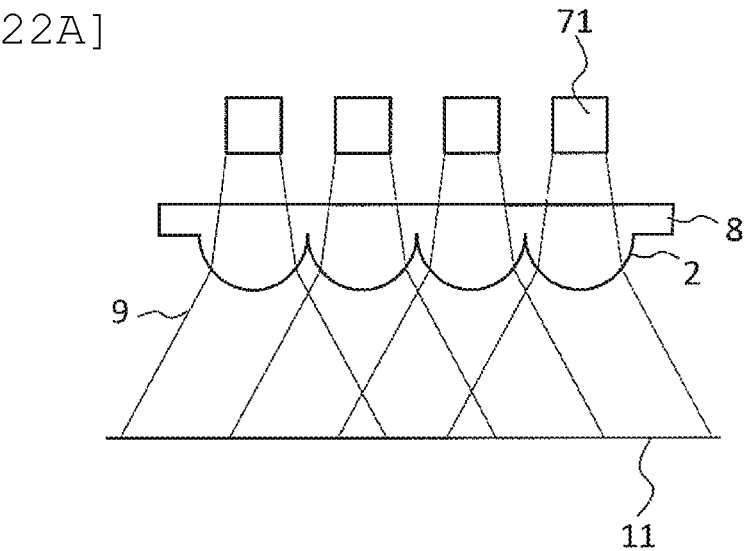
[FIG. 22B]
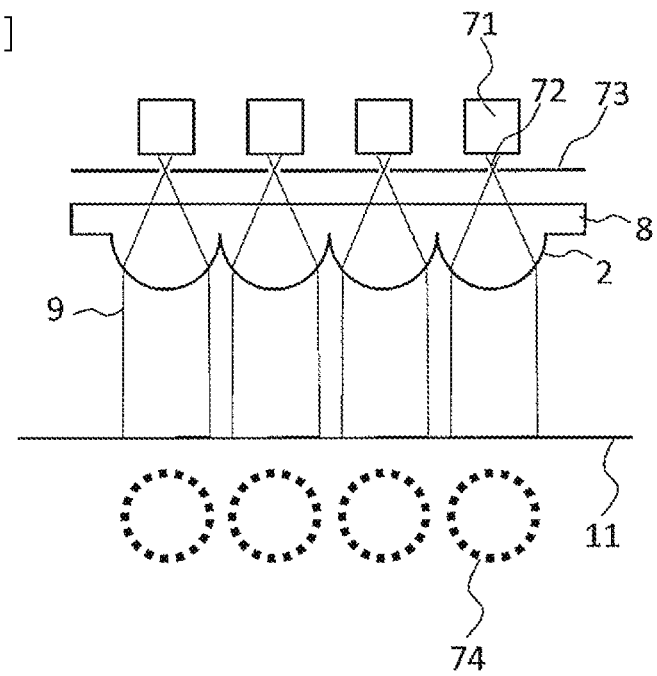

[FIG. 23A]
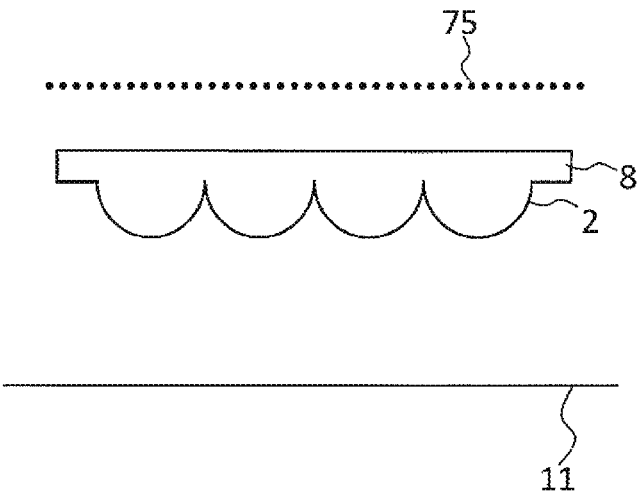
[FIG. 23B]
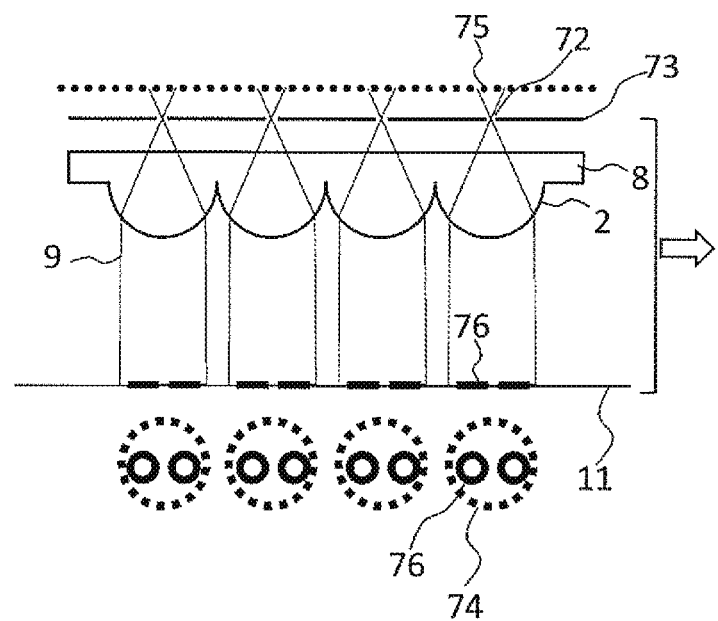

[FIG. 24A]
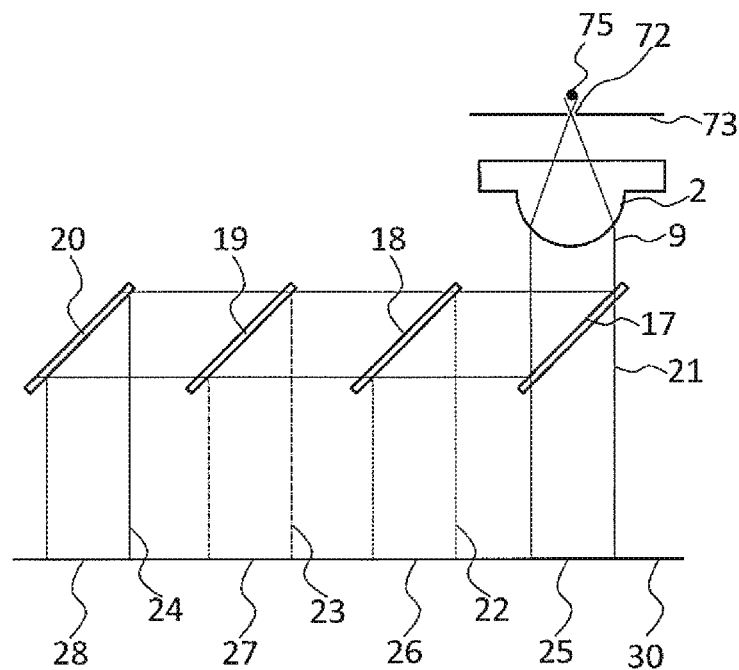
[FIG. 24B]
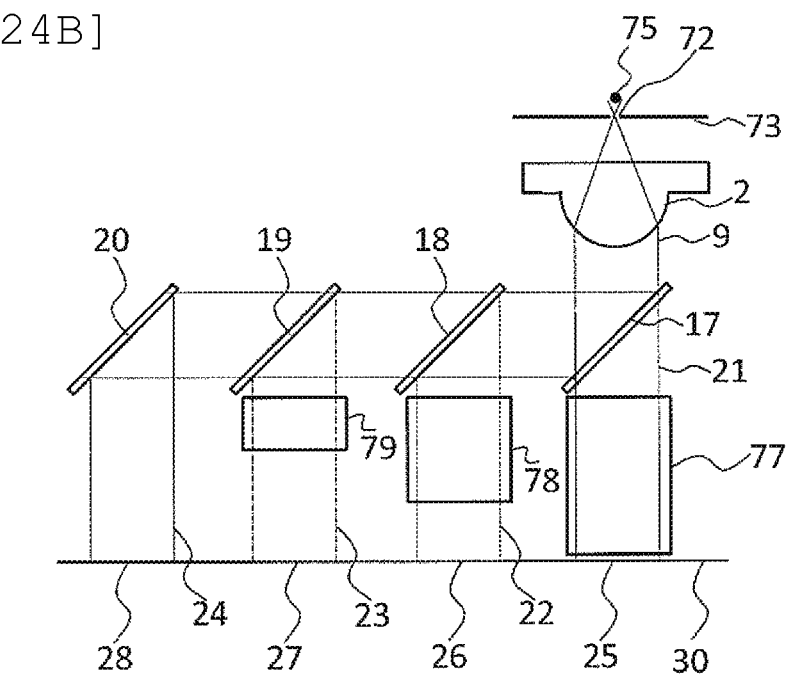

[FIG. 25A]
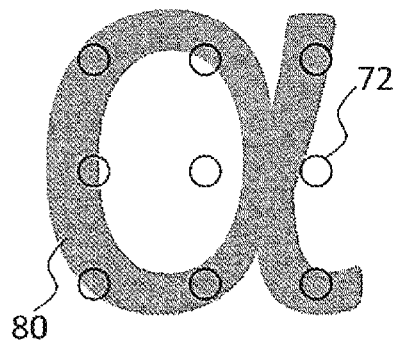
[FIG. 25C]
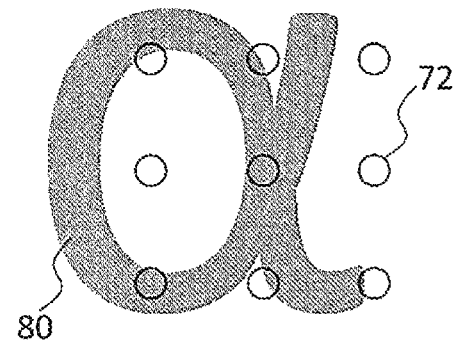
[FIG. 25B]
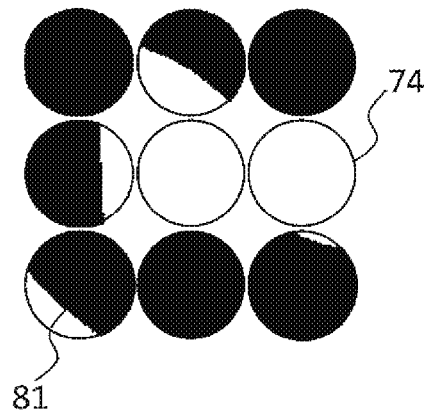
[FIG. 25D]
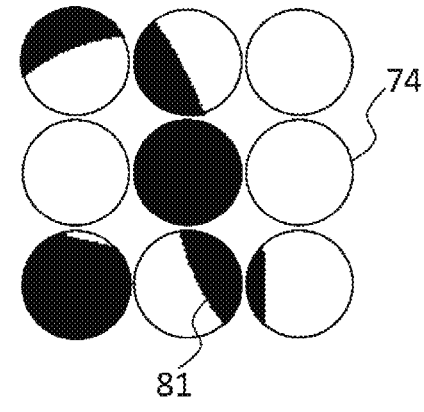

[FIG. 26A]
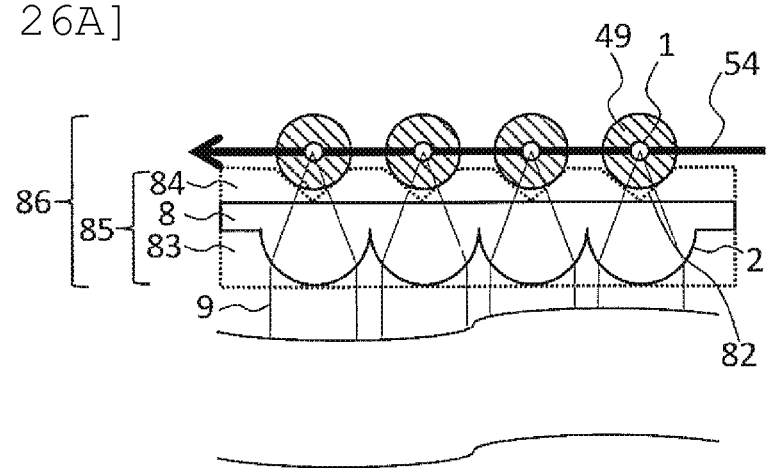
[FIG. 26B]
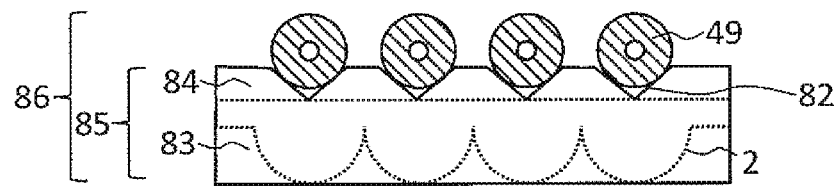
[FIG. 26C]
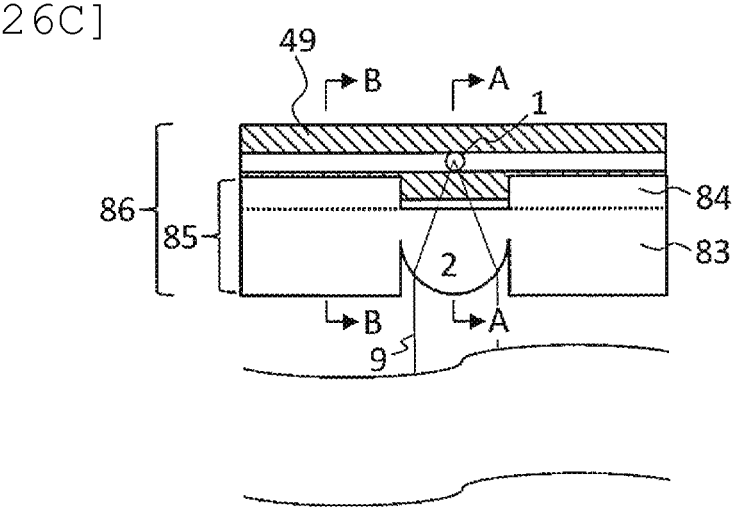

[FIG. 27A]
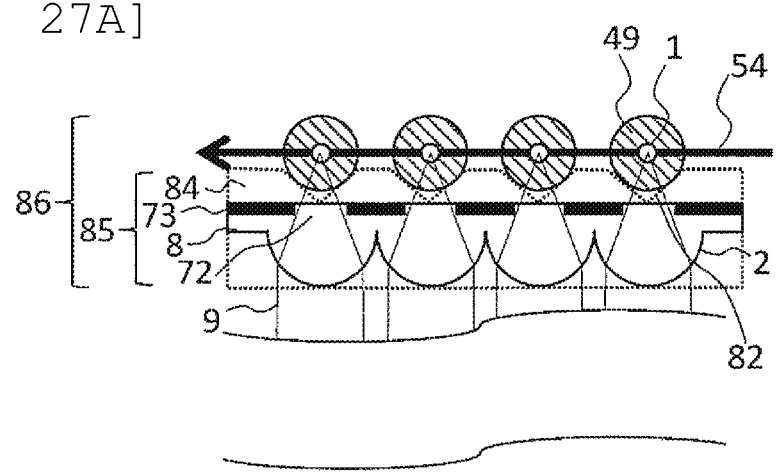
[FIG. 27B]
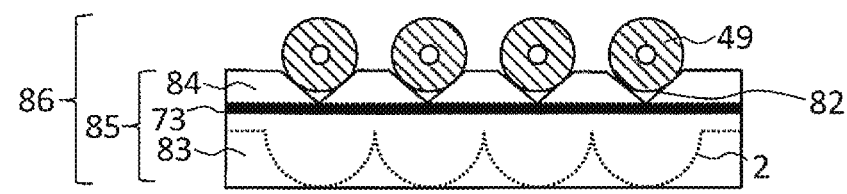
[FIG. 27C]
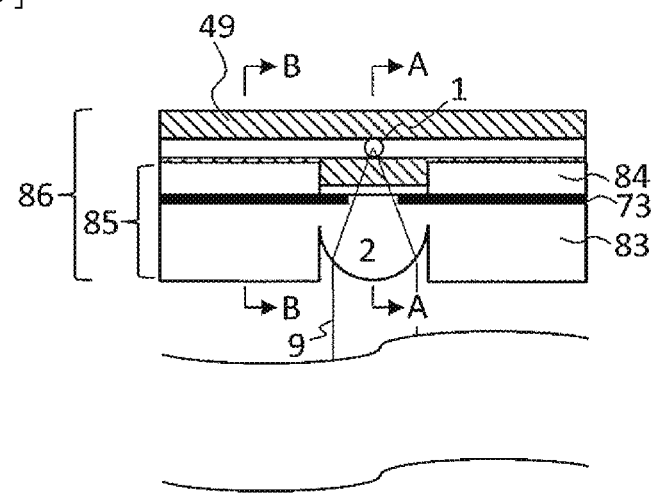

[FIG. 28A]
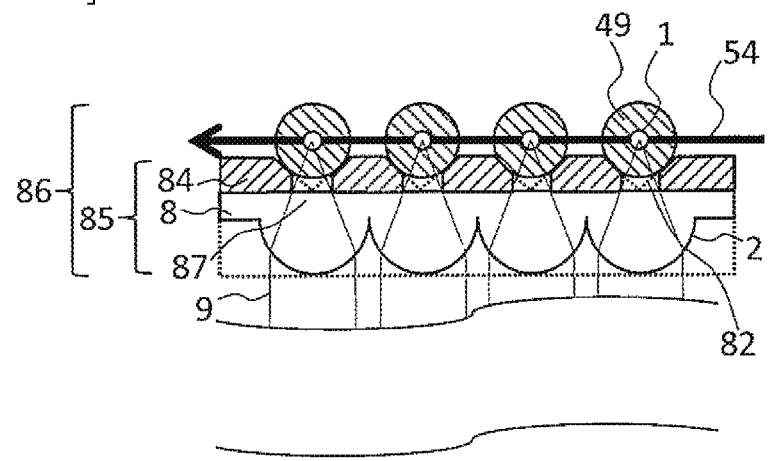
[FIG. 28B]
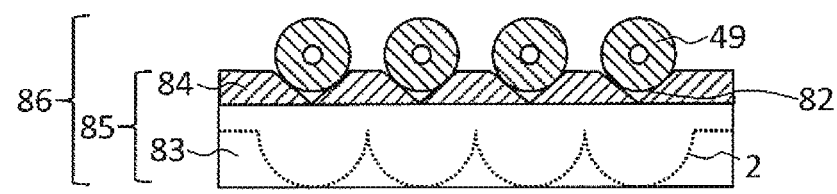
[FIG. 28C]
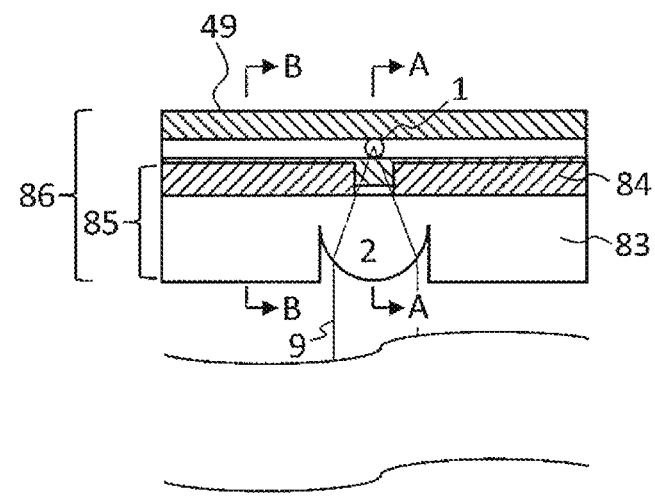

LIGHT-EMITTING DETECTION DEVICE

CROSS REFERENCE TO RELATED APPLICATIONS

This application is a continuation of U.S. patent application Ser. No. 16/076,212, filed Aug. 7, 2018, which is a 371 of International Application No. PCT/JP2016/055031, filed Feb. 22, 2016, the disclosures of all of which are expressly incorporated by reference herein.

TECHNICAL FIELD

The present invention relates to a detection apparatus which irradiates a plurality of channels provided inside a plurality of capillaries or a microchip with light such as a laser beam or a lamp and detects fluorescence, phosphorescence, scattered light, transmitted light, or the like emitted by a substance present inside the capillary or the channel with high sensitivity.

BACKGROUND ART

A capillary array DNA sequencer which collectively deciphers base sequences of different DNA samples in individual capillaries by performing electrophoretic analysis in parallel processing using the plurality of capillaries (glass capillary each having an outer diameter of 100 µm to 400 µm and inner diameter of 25 µm to 100 µm) filled with a separation medium is widely used. This mechanism will be described next. A polyimide coating film is formed on an outer surface of a commercial capillary in order to preserve flexibility. Portions of capillaries having the same electrophoretic length, for example, the vicinities of positions that are 30 cm away in distance from a respective sample-injection end of the capillary, are arranged to be aligned on the same plane (a capillary-array plane) the coating film being removed. Then, a laser beam is irradiated from a side of the capillary-array plane so as to simultaneously irradiate the plurality of capillaries with the laser beam. Hereafter, the capillary-array plane may be simply called an array plane in the present specification. When passing across a laser beam, fluorescent labeled DNA fragments which are subjected to electrophoresis inside each capillary described above emit fluorescence by being excited by laser irradiation. Here, DNA fragments are labeled with fluorescent substances of four colors depending on the terminal base species of A, C, G, and T. As a result, laser-irradiation positions of respective capillaries become emission points and a plurality of emission points are arranged on a straight line at intervals of p. Hereafter, this is called an emission-point array. When the number of the emission points (number of capillaries) is set to M, the entire width AW of the emission-point array is $AW = p*(M-1)$. For example, when $p=0.36$ mm and $M=24$, $AW=8.28$ mm. A fluorescence-detection apparatus collectively detects respective light beams emitted from the emission-point array while spectroscopically separating the light beams. A configuration of the system is illustrated in JP-A-2007-171214 (PTL 1).

First, respective emitted light beams are turned into parallel-light beams by a common condensing lens. Hereafter, an expression of "common" is used as the meaning (M-to-1 correspondence) that one optical element is used for a plurality of emission points (M emission points). In contrast, an expression of "individual" is used as the meaning (1-to-1 correspondence) that one optical element is used for one emission point. Here, when the focal length of the common condensing lens is set as f1 and an effective diameter is set as D1, it needs to be $AW<f$ and $AW<D1$. For example, the condensing lens is a camera lens with $f1=50$ mm and $D1=36$ mm. Next, the parallel-light beams are allowed to be passed through a longpass filter so as to cut the laser beam and further allowed to be transmitted through a common transmission type diffraction grating so as to be subjected to wavelength dispersion in the long axis direction of each capillary, that is, the direction orthogonal to both the array direction of the emission-point array and the optical axis of the common condensing lens. Here, when the effective diameter of the common transmission type diffraction grating is set as DG, it needs to be $D1 \leq DG$ so as not to decrease detection efficiency. For example, $DG=50$ mm. Subsequently, the image of respective parallel-light beams are formed on the two-dimensional sensor by a common imaging lens. Here, when the focal length of the common imaging lens is set as f2 and the effective diameter is set as D2, it needs to be $D1 \leq D2$ so as not to decrease detection efficiency. For example, the imaging lens is a camera lens with $f2=50$ mm, $D2=36$ mm. With matters as described above, it is possible to collectively acquire wavelength dispersion spectra of respective light beams emitted from the emission-point array. Finally, temporal change in respective wavelength dispersion spectra is analyzed so as to obtain temporal change in intensity of fluorescence of four colors and determine the sequence of base species, that is, the base sequence.

Other ways for simultaneous fluorescence detection of four colors is illustrated in NPL 1. First, a light beam emitted from one emission area is turned into a parallel-light beam by one condensing lens (here, objective lens). Here, when the entire width of the emission area is set as AW, the focal length of the objective lens is set as f, and the effective diameter is set as D, $AW<f$ and $AW<D$. The objective lens in use is UPLSAPO 60X W which is the Olympus's product, and $AW=0.44$ mm, $f1=3$ mm, and $D1=20$ mm. Next, the parallel-light beam is divided into four parallel-light beams of four colors by one set of three kinds of dichroic-mirrors. Subsequently, images of respective parallel-light beams are formed on four two-dimensional sensors by one set of four imaging lenses. Here, when the effective diameter of each imaging lens is set as D2, it needs to be $D1 \leq D2$ so as not to decrease detection efficiency. With matters as described above, it is possible to collectively acquire four-divided images of four colors of the emission area.

On the other hand, other means for simultaneous detection of light beams emitted from the emission-point array is illustrated in JP-A-2011-59095 (PTL 2). First, respective light beams emitted from the emission-point array are turned into the individual parallel-light beams by a condensing-lens array. Here, when intervals between the emission points is set as p and the number of emission points is set as M, the entire width of the emission-point array is $AW=p*(M-1)$. When the effective diameter of each condensing lens is set as D, $D<AW$. Therefore, it is a configuration different from those of PTL 1 and NPL 1. Setting D as $D<p$ may provide a condensing-lens array in which individual condensing lenses are respectively aligned in a straight line. Next, respective parallel-light beams are made incident respectively on individual sensors of the sensor array. With matters as described above, it is possible to collectively acquire intensities of light beams emitted from the emission-point array.

CITATION LIST

Patent Literature

PTL 1: JP-A-2007-171214
PTL 2: JP-A-2011-59095

Non-Patent Literature

NPTL 1: Rev Sci Instrum., 2011 February; 82(2):023701.

SUMMARY OF INVENTION

Technical Problem

The emission (fluorescence) detection apparatus (system) of PTL 1 has high light condensing efficiency (light condensing efficiency by the common condensing lens) and high detection efficiency (total utilization efficiency of emitted light contributing to fluorescence-detection by the sensor based on light condensing efficiency, transmissivity of the longpass filter, diffraction efficiency of the diffraction grating, or the like) of light beams emitted from the emission points and also has high spectroscopic accuracy by the diffraction grating. The condensing efficiency can be expressed by the F-number of the common condensing lens and is proportional to $1/F^2$. For example, in a case where the camera lens with $f1=50$ mm and $D1=36$ mm, the F-number is $F=f1/D1=1.4$. Because F-number of 1.4 is relatively small, the emission detection can be performed with high-sensitivity. In addition, since the emitted light beams from the emission points are respectively imaged with the common imaging lens and is detected by a two-dimensional sensor, the emitted light beams do not mix with each other. That is, the emitted light beams can be independently detected with a low crosstalk. The property of above-described high sensitivity and low crosstalk is particularly important in the technical field for accurately detecting a trace amount of an object to be measured or simultaneously and independently detecting a plurality of different objects to be measured. However, the emission detection apparatus includes two common lenses and has a relation in which $AW<f$ and $AW<D1 \leq D2$. Thus, when AW is set to be constant, there is a problem to be solved that the entire size of the system is very large and the manufacturing cost of the system is high. For example, in a case where the camera lenses with $f1=f2=50$ mm, $D1=D2=36$ mm are used, the entire size of the emission detection apparatus becomes larger than the volume of a column ($1.6*10^6$ mm$^3$) having the diameter of 100 mm and the height of 200 mm. In the present specification, an entire size of an emission detection apparatus is represented by an occupation volume of an optical system from a emission point (emission points) to a sensor (a sensor surface), and an occupation volume of the sensor itself is not included in representation of the entire size. Setting of $AW<<f1$ and $AW<<D1$ cannot be allowed (a huge camera lens is needed to achieve the setting) and thus, there is a problem to be solved that detection efficiency of the emission point separated from the optical axis (the emission point positioned in the vicinity of the ends of the emission-point array) is decreased compared to detection efficiency of the emission point in the vicinity of the optical axis (the emission point positioned in the vicinity of the center of the emission-point array), and variation in detection sensitivity occurs among the emission points.

However, means for solving the problems to be solved has not been conducted so far. That is, efforts for realizing miniaturization and cost reduction of a system that detects light beams of four colors emitted from a emission-point array while simultaneously identifying the colors of the emitted-light beams, and for reducing variation in detection sensitivity of the respective emitted-light beams, have not been performed so far. Miniaturizing the emission detection apparatus may allow capillary array DNA sequencers to be installed at a small area, or to be carried. Alternatively, it may improve usability of the apparatus. Also, the number of components in the detection apparatus is reduced, or the size of each component becomes smaller to thereby reduce the manufacturing cost of the apparatus. Furthermore, variation in detection sensitivity of the respective emission points is reduced to thereby make it possible to allow quantitative comparison of samples analyzed in the respective capillaries and improve a dynamic range and total detection sensitivity of the emission-point array. As the results, the capillary array DNA sequencer can be further spread and more contribute to the world.

Using the emission detection apparatus described in NPL 1 may allow performing simultaneous fluorescence-detection of light beams of four colors emitted from a emission-point array in a similar way. However, since the objective lens used in NPL 1 has AW of $AW=0.44$ mm, only a portion of the entire width (for example, 8.28 mm) of the emission-point array can be detected. Accordingly, similar to the capillary array DNA sequencer, a common condensing lens and four common imaging lenses are used, instead of using an objective lens and four imaging lenses. In this case, when the effective diameter of three kinds of dichroic-mirrors is set as DM, the dichroic-mirrors are disposed to be inclined at 45° with respect to parallel-light beams. Therefore, it needs to be $\sqrt{2}*D1<DM$ so as not to reduce detection efficiency. For example, $DM=71$ mm. Accordingly, even when four two-dimensional sensors are not included, the entire size of the emission detection apparatus becomes larger than the case of PTL 1 and manufacturing cost is increased that much. In addition to this, space occupied by four two-dimensional sensors is large and cost for that is very high. Also, the problem of sensitivity variation among emission points remains unsolved.

On the other hand, when the emission detection apparatus disclosed in PTL 2 is used, it is possible to make the size of the apparatus smaller because $D<AW$. However, in a case where each light emitted from the emission-point array is condensed by the individual condensing-lens array, as in this literature, it is difficult to obtain both high sensitivity performance and low crosstalk performance, because these two performances share trade-off relationship. In PTL 2, no discussion or consideration has been made on such problems and means for solving the problems. The problems will be described below in detail.

As described above, light-condensing efficiency can be expressed by $F=f/D$ (the light-condensing efficiency is proportional to $1/F^2$), where f and D are a focal length and an effective diameter of each condensing lens. Here, assuming that D is constant, the smaller the focal length f becomes, that is, the closer the emission point and the condensing lens are, the more the light-condensing efficiency appears to increase. This is correct when the emission point has an infinitely small size, but is not necessarily correct when the emission point has a finitely small size. Here, when the diameter of the emission point is defined as d, the infinitely small size means a case where $d<<f$ or d 26 0, and the finitely small size means a case where $d>0$. In practice, finitely small size means a case where $d\geq 0.01$ mm. Hereinafter, in the present invention, a case where the size of the emission point is finite will be considered. When the center of the emission point is placed at the focal position of the lens, the light emitted from the center of the emission point is converted into a parallel light beam by the lens, and the light beam travels in a direction parallel to the optical axis along the optical axis of the lens. On the other hand, the light emitted from the end of the emission point is converted into a parallel light beam by the lens, and the light beam travels in a direction forming an angle $\theta=\tan-1(d/2/f)$ with the optical axis of the lens. That is, these light beams are separated as being away from the lens. Therefore, when the light beams are detected by arranging a sensor having the size of the parallel light beam of light emitted from the center of the emission point at a position on the optical axis of the lens and being away from the lens by a certain distance (or by assigning a part of an area sensor), all of the condensed light emitted from the center of the emission point can be detected. In contrast, only part of the condensed light emitted from the end of the emission point can be detected. Since the angle $\theta$ decreases as the focal length f increases, the detection ratio of the condensed light emitted from the emission point increases with the focal length f.

As described above, in order to improve the light-condensing efficiency and obtain high sensitivity, it is understood that f should be made smaller from a certain viewpoint, while f should be made larger from another viewpoint. There is a trade-off relation between these viewpoints. However, no studies about the best value for f to obtain high sensitivity have been performed so far, including PTL 2. As will be described below, as a result of carrying out this study under practical conditions in the present invention, it was found that as the f is smaller, the overall light-condensing efficiency improves. This indicates that the effect of decreasing the focal length f to increase the detection-light quantity of the light emitted from the center of the emission point is larger than the effect of increasing the focal length f to increase the detection-light quantity of the light emitted from the end of the emission point.

On the other hand, discussion for crosstalk needs to be made separately from the above light-condensing efficiency. Since the angle $\theta$ becomes large when the f becomes small, the ratio of the condensed light emitted from the end of the emission point overlapping with the adjacent sensor (or an area to which a part of an area sensor is assigned) arranged for detecting the condensed light emitted from the adjacent emission point increases, and thus the crosstalk in detecting the condensed light emitted from the adjacent emission point increases. That is, it was found that there is a trade-off relation between a viewpoint of decreasing f to improve the light-condensing efficiency and obtain the high sensitivity and a viewpoint of increasing f to reduce the crosstalk. However, studies about the best f for achieving both the high sensitivity and the low crosstalk have not been performed so far, including PTL 2.

Solution to Problem

An emission detection apparatus according to the present invention includes: a condensing-lens array that is arranged with M condensing lenses for individually condensing lights emitted from a emission-point array, in which M emission points are arranged, to form M light beams, where M is an integer number more than 2 (M≥2); at least one sensor on which the M light beams are incident in parallel without being re-condensed, wherein when an average of effective diameters of the M emission points is d, an average of focal lengths of the M condensing lenses is f, an average of intervals of the M condensing lenses is p, and an average of maximum optical path lengths between the M condensing lenses and the sensor is g, the d, f, p, and g satisfy a certain relation that is predetermined so as to be capable of detecting the M pieces of light emission with low crosstalk and/or high sensitivity.

Advantageous Effects of Invention

According to the present invention, it is possible to reduce the size of the apparatus which detects lights emitted from the emission-point array with high sensitivity and low crosstalk, and to reduce the entire size of various analytical systems using the apparatus. Accordingly, it is possible to reduce space in which the analytical systems are to be placed, and to carry the analytical systems, and usability of the analytical systems is improved. The number of components constituting the apparatus is reduced and the components themselves are miniaturized to thereby make it possible to reduce manufacturing cost.

In addition to matters described above, other problems to be solved, other configurations, and other effects will be apparent from description of the following embodiments.

BRIEF DESCRIPTION OF DRAWINGS

FIG. 1 is a schematic diagram of a configuration in which light emitted from a emission point is condensed by a condensing lens to form a light beam.

FIG. 2 is a diagram illustrating a relation between an optical path length g (between a condensing lens and a sensor) and a relative detection-light quantity, using the focal length f of the condensing lens as a parameter.

FIG. 3 is a schematic diagram of a configuration in which two lights emitted from adjacent two emission points are individually condensed by two condensing lenses to form two separated light beams.

FIG. 4 is a schematic diagram of a configuration in which two lights emitted from adjacent two emission points are individually condensed by two condensing lenses to form two overlapped light beams.

FIG. 5 is a diagram illustrating a relation between an optical path length g (between the condensing lens and the sensor) and the focal length f of the condensing lens, indicating conditions satisfying high sensitivity and low crosstalk.

FIGS. 6A and 6B are schematic diagrams of a emission detection apparatus by individually condensing lights emitted from a emission-point array using the condensing-lens array and allowing the condensed lights to enter a color sensor in parallel for detection.

FIGS. 7A to 7C are schematic diagrams of a emission detection apparatus by individually condensing lights emitted from a emission-point array using the condensing-lens array, respectively dividing the condensed light beams in parallel into multicolor beams with different wavelengths by a dichroic-mirror array, and making all the multicolor beams incident on a sensor in parallel.

FIGS. 8A to 8C are schematic diagrams of a emission detection apparatus by individually condensing lights emitted from a emission-point array using the condensing-lens array, obtaining dispersing lights of the condensed light beams in parallel with a wavelength dispersion element, and forming individually images of the dispersing lights with an imaging-lens array.

FIGS. 9A and 9B are schematic diagrams of a emission detection apparatus by individually condensing lights emitted from a emission-point array using the condensing-lens array, deflecting the condensed light beams in parallel with an optical element, and making the deflected light beams incident on a sensor in parallel.

FIGS. 10A and 10B are schematic diagrams of a emission detection apparatus by individually condensing lights emitted from a emission-point array using the condensing-lens array, deflecting the condensed light beams in parallel with an optical-fiber array, and making the deflected light beams emitted from the optical-fiber array incident on a sensor in parallel.

FIG. 11 is a schematic diagram illustrating an apparatus configuration example of a capillary array DNA sequencer.

FIG. 12 is a diagram illustrating an example of a dichroic-mirror array in which a parallel light beam parallel to the dichroic-mirror array direction incident on the dichroic-mirror array in parallel is divided to a vertical direction to the dichroic-mirror array direction, and a result of calculation of the largest width of the parallel light beam that can be divided by the dichroic-mirror array.

FIG. 13 is a diagram illustrating an example of a dichroic-mirror array in which a parallel light beam vertical to the dichroic-mirror array direction incident on the dichroic-mirror array is divided to a vertical direction to the dichroic-mirror array direction, and a result of calculation of the largest width of the parallel light beam that can be divided by the dichroic-mirror array.

FIG. 14 is a diagram illustrating an example of a miniaturized dichroic-mirror array in which a parallel light beam vertical to the dichroic-mirror array direction incident on the dichroic-mirror array is divided to a vertical direction to the dichroic-mirror array direction, and a result of calculation of the largest width of the parallel light beam that can be divided by the dichroic-mirror array.

FIG. 15 is a diagram illustrating an example of a miniaturized and shift dichroic-mirror array in which a parallel light beam vertical to the dichroic-mirror array direction incident on the dichroic-mirror array is divided to a vertical direction to the dichroic-mirror array direction, and a result of calculation of the largest width of the parallel light beam that can be divided by the dichroic-mirror array.

FIG. 16 is a diagram illustrating a configuration of a best mode of a dichroic-mirror array that reduce an optical path length and enlarges an aperture width.

FIG. 17 is a diagram illustrating a relation between a thickness $\beta$ of dichroic mirrors and an interval x of a dichroic-mirror array, in which an optical path length of the dichroic-mirror array is $L_{max}$ or less and an aperture width of the dichroic-mirror array is $W_{min}$ or more.

FIG. 18 is a diagram illustrating a relation between an interval x of a dichroic-mirror array, and an aperture width W, and an optical path length change $\Delta L$.

FIGS. 19A and 19B are diagrams illustrating a relation between steps y and z of a dichroic-mirror array and an aperture width W.

FIG. 20 is a diagram illustrating an example of a dichroic-mirror array in which a parallel light beam vertical to the dichroic-mirror array direction incident on the dichroic-mirror array is divided vertically to the dichroic-mirror array direction and dichroic mirrors are inclined over 45° to the parallel light beam direction, and a result of calculation of the largest width of the parallel light beam that can be divided by the dichroic-mirror array.

FIG. 21 is a diagram illustrating a relation between an inclination angle $\theta_0$ of dichroic mirrors to the parallel light beam direction and an aperture width W of a dichroic-mirror array.

FIGS. 22A and 22B are schematic diagrams of an emission detection apparatus by transmitting individually parts of lights emitted from a emission-point array through a pinhole array, condensing individually the transmitted lights with a condensing-lens array, and making the condensed lights incident on a sensor in parallel.

FIGS. 23A and 23B are schematic diagrams of an emission detection apparatus by transmitting individually parts of lights emitted from a emission-point array, where emission points are arranged at intervals smaller than intervals at which condensing lenses are arranged in a condensing-lens array, through a pinhole array, condensing individually the transmitted lights with a condensing-lens array, and making the condensed lights incident on a sensor in parallel.

FIGS. 24A and 24B are schematic diagrams of an emission detection apparatus by transmitting individually parts of lights emitted from a emission-point array through a pinhole array, condensing individually the transmitted lights with a condensing-lens array to form light beams, respectively dividing the condensed light beams in parallel into multicolor beams with different wavelengths with a dichroic-mirror array, and making the multicolor beams incident on a sensor in parallel.

FIGS. 25A to 25D are schematic diagrams of imaging of an emission area by a emission detection apparatus including a pinhole array, a condensing-lens array, and a scanning mechanism.

FIGS. 26A to 26C are schematic diagrams illustrating a configuration example of a device in which a V-groove array where a plurality of capillaries are arranged and an individual condensing-lens arrays are integrated.

FIGS. 27A to 27C are schematic diagrams illustrating a configuration example of a device in which a V-groove array where a plurality of capillaries are arranged, a pinhole array, and an individual condensing-lens arrays are integrated.

FIGS. 28A to 28C are schematic diagrams illustrating a configuration example of an opaque device in which a V-groove array where a plurality of capillaries are arranged and a pinhole array are integrated and an integrated device in which the opaque device and an individual condensing-lens arrays are joined.

DESCRIPTION OF EMBODIMENTS

FIG. 1 is a schematic sectional view including an optical axis of an optical system for condensing light emitted from an emission point 1 using a condensing lens and detecting with a sensor disposed at a position separated from the condensing lens by a certain distance. In the present invention, the terms "emission point" and "light emission" are often used, but this does not necessarily mean that the substance to be detected itself emits fluorescence, phosphorescence, or the like, but often means scattered light generated from the detection object by irradiating the detection object with light or transmitted light through the detection object. Therefore, these terms are expressed collectively as light emission from the emission point.

The diameter of the emission point 1 is defined as "d", the focal length of the condensing lens 2 is defined as "f", the effective diameter of the condensing lens 2 is defined as "D", the diameter of a detection area of the sensor is defined as "D", and the optical distance (optical path length) between the condensing lens 2 and the sensor is defined as "g". When the distance between the emission point 1 is fs, that is, when the center of the emission point 1 is located at the focal position of the condensing lens 2, the light emitted from the center of the emission point 1 forms a parallel light beam 3 having a diameter D by the condensing lens 2, and travels in an optical axis direction. In the sensor located at a position separated from the condensing lens 2 by the optical path length g, the parallel light beam 3 forms a spot 4 having a diameter D. FIG. 1 illustrates the emission point 1 disposed at a lower side of the optical system as viewed in the optical axis direction and the spot 4 and a spot 5 (to be described below) disposed at an upper side thereof as viewed in the optical axis direction. On the other hand, the light emitted from a left end of the emission point 1 is converted into a parallel light beam 3' having a diameter D by the condensing lens 2, and travels in a direction at an angle θ with the optical axis. In the sensor, the parallel light beam 3' forms the spot 5 having a diameter D.

The light-condensing efficiency of the light emitted from the center of the emission point 1 is proportional to $1/F^2$, where F denotes an F-number of the condensing lens 2. Since F=f/D, if D is constant, the smaller the focal length f becomes, the higher the light-condensing efficiency becomes. On the other hand, the spot 5 of the light emitted from the left end of the emission point 1 shifts to a right side from the detection area of the sensor. That is, the spot 4 is wholly detected, but the spot 5 is detected at a rate at which the spot 5 overlaps with the spot 4. As the overlapped portion becomes greater, the quantity of the condensed light to be detected over the entire area of the emission point increases. For this reason, it is preferable that the angle θ at which the parallel light beam 3' propagates with respect to the optical axis becomes smaller. Since $\theta=\tan^{-2}(d/2/f)$, it is preferable that the focal length f is larger, if d is constant. As described above, in order to increase the detection-light quantity of the emission point 1, f should be made smaller from a certain viewpoint, while f should be made larger from an another viewpoint. Although there is a trade-off relation between these viewpoints, studies about the best range of f have not been done so far. Accordingly, conditions of the f and g for increasing the detection-light quantity of the emission point 1 will be clarified below.

In order to evaluate the detection-light quantity, the fluorescence-detection apparatus illustrated in FIG. 3 of PTL 1 is used as a reference. In a typical example of the fluorescence-detection apparatus, a focal length of a common condensing lens f1 is f1=50 mm and an effective diameter D1 is D1≥25 mm. F-number of the lens F is F f1/D1≤2.0. In a case where a condensing lens having $F_0$=2.0 is used, when light emitted from a emission point having an infinitely small size and positioned at a focal point of the lens is turned into a parallel-light beam by the lens and the parallel-light beam is detected by the sensor without loss, a detection-light quantity is set as a reference (100%). Hereafter, a detection-light quantity for any emission point having an infinitely small size is evaluated by a relative detection-light quantity with respect to the reference. It is considered that the emission point having a finite size with the average effective diameter d is composed of a multitude of emission points each having an infinitely small size. In the present specification, the "emission point having a finite size" is simply called a "emission point" and the "emission point having an infinitely small size" is called a "emission point having an infinitely small size" at all such times. The relative detection-light quantity of the emission point is set as an average of the relative detection-light quantities of a large number of emission points each having an infinitely small size and constituting the emission point. For example, in the example described above, when the condensing lens is replaced to F=1.4 from F=2.0, light-condensing efficiency is increased $(F_0/F)^2$=2.0 times and thus, the relative detection-light quantity of the emission point having an infinitely small size becomes 200%. Here, it is assumed that the entire light quantity omni-directionally emitted from the emission point is constant and emission density within the inside the emission point is spatially uniform. In the typical example of the present fluorescence-detection apparatus, the interval between the emission points of the emission-point array is p=0.36 mm, the number of the emission points is M=24, the entire width of the emission-point array is AW=p* (M−1) =8.28 mm. Since the emission point at the center of the emission-point array is positioned at vicinity of the focal point of the lens, the relative detection-light quantity of the emission point is almost 100%. On the other hand, since the emission point at either end of the emission-point array is positioned away from the focal point of the lens, the relative detection-light quantity of the emission point is decreased to approximately 50%. Therefore, the present invention aims to make the relative detection-light quantity of each emission point 50% or more so that detection sensitivity of each emission point becomes greater than or equal to that in the related art.

FIG. 2 is a diagram illustrating the results of calculation of a relation between g and a relative detection-light quantity, by using f as a parameter in the configuration illustrated in FIG. 1. Here, the average effective diameter of the emission point 1 is set as d=0.05 mm. The effective diameter of the individual condensing lens 2 is set as D=0.5 mm. The relative detection-light quantity is calculated based on F-number of the lens, F=f/0.5. The emission point 1 having the effective diameter d=0.05 mm is composed of approximately 500 emission points having an infinitely small size and arranged at 0.1 μm intervals, and the relative detection-light quantity is calculated for each emission point having the infinitely small size, based on the same calculation of overlap area ratio of the spot 4 and the spot 5 of FIG. 1. The relative detection-light quantity of the emission point 1 is obtained by averaging the relative detection-light quantities of all the emission points having the infinitely small size. As a result, as illustrated in FIG. 2, it was firstly figured out that the smaller the f and the smaller the g, the greater the relative detection-light quantity. This indicates that effect of decreasing the f to increase of the relative detection-light quantity of the emission point having the infinitely small size and positioned at the center of the emission point 1 is greater than effect of increasing the f to increase of the overlap area ratio. Also, it indicates that effect of decreasing the g to increase of the overlap area ratio is large for any focal point f.

In FIGS. 1 and 2, the center of the emission point 1 is disposed at the focal point of the condensing lens 2, and the light emission is made into a parallel light beam. The present invention functions satisfactorily even under these conditions, but as will be described below in detail, if the center of the emission point 1 is slightly separated from the focal point of the condensing lens 2 and the light emission is converted into a slightly focused light beam 6, it has been found out that it is more preferable condition for achieving both high sensitivity and low crosstalk. More specifically, since the diameter of the spot of the emission point 1 can be minimized in a case where the image of the emission point 1 is formed at the position of the sensor, that is, at a position of the optical path length g from the condensing lens 2, it was found that the case was the best condition.

FIG. 3 is a sectional view including the optical axes of the optical systems that respectively condenses lights emitted from adjacent two emission points 1 using the individual condensing lenses 2 and respectively obtains emission point images 7, which are images of the emission points 1, at the sensor position. In the present invention, the expression "emission point image" does not necessarily mean an image on which the light emitted from the emission point is just focused, but generally means a cross section of the light beam in which the light emitted from the emission point is condensed, at a predetermined position. The diameter of the emission point 1 is defined as "d", the focal length of the condensing lens 2 is defined as "f", the effective diameter of the condensing lens 2 is defined as "D", the interval between the emission points 1 and the interval between the condensing lenses 2 is respectively defined as "p", the diameter of the detection area of the sensor is defined as "D", the optical distance (optical path length) between the condensing lens 2 and the sensor is defined as "g", and the diameter of the emission point image 7 at the sensor position is defined as "d'". When the distance between the emission point 1 and the condensing lens 2 is adjusted and the light emitted from the emission point 1 is just focused at the sensor position by the condensing lens 2, the diameter d' of the emission point image 7 is minimized.

At this time, since image magnification m is expressed as follows.

$$m=(g-f)/f,$$ [Equation 1]

the diameter d' of the emission point image 7 is as follows.

$$D' \geq m*d = (g-f)/f*d$$ [Equation 2]

Here, Equation (2) establishes an equal sign when the light emitted from the emission point 1 is just focused at the sensor position by the condensing lens 2, and establishes an inequality sign in other cases. FIG. 3 illustrates the emission points 1 disposed at a lower side of the optical systems as viewed in the optical axes direction and the emission point images 7 disposed at an upper side as viewed in the optical axes direction. The present invention functions satisfactorily when $g \geq 2*f$, that is, when $m \geq 1$. More preferably, a good condition is obtained when $m \geq 5$ or $m \geq 10$. This is be cause, as is apparent from FIG. 2, it is necessary to reduce the focal length "f" to the mm-level in order to improve the relative detection-light quantity, but is physically difficult to reduce the optical distance "g" so much.

In each of the drawings of this specification, the emission point 1 and the emission point image 7 are drawn in a circular shape, respectively, but may have other shapes in reality without being limited to the circular shape. In general, the diameter d of the emission point 1 and the diameter d' of the emission point image 7 are respectively widths in an arrangement direction of the emission points and the emission point images 7. Further, as will be described below, a plurality of optical distances (optical path lengths) may be present between the condensing lens 2 and the sensor in the same e optical system. In that case, assuming that the optical distance between the condensing lens 2 and the sensor is generally set to an optical path length "s" and the maximum value of s is set to the optical path length g, the above Equations (1) and (2) and the following Equations (3) to (18) may be established. The reason will be described below. When the optical distance between the condensing lens 2 and the sensor is represented by a variable s, $0 \leq s \leq g$, with g being the maximum value. At this time, the diameter d' (s) of the emission point image at any variable s is smaller than the larger one of d'(s=0)=D and d'(s=g)=d'. That is, when D d', d' (s) D; and when D≤d', d' (s)≤d'. In the former case, the crosstalk does not occur, and in the latter case, if the crosstalk does not occur with s=g, this means that the crosstalk does not occur even if $0 \leq s \leq g$. On the other hand, the relative detection-light quantity is constant regardless of the optical path length "s".

In the description, the condensing lens 2 basically has a circle shape having an effective diameter D as its diameter, but it is not necessary. Generally, the effective diameter D of the condensing lens 2 indicates a width in the arrangement direction of the emission points 1 or the arrangement direction of the condensing lenses 1, and a width in a direction orthogonal to the arrangement directions is not limited thereto. The condensing lens 2 may be circular, elliptical, square, rectangular, or any other shapes. In the above discussion, the diameter d'(s=0)=D of the emission point image 7 may be regarded as a diameter in the arrangement direction of the emission points 1 or the arrangement direction of the condensing lenses 1. The diameter of the emission point image 7 in the direction orthogonal to the arrangement directions does not contribute to the crosstalk no matter how large it is. In addition, if g is sufficiently large, d'(s=g)=d' is irrelevant to D. Therefore, conditions of the following Equations (13) to (18) relating to the crosstalk are established regardless of the width in the direction orthogonal to the arrangement direction of the condensing lenses 2. On the other hand, if the width in the direction orthogonal to the arrangement direction of the condensing lenses 2 is larger than the effective diameter D, the F-number can be smaller than F=f/D, that is, the light-condensing efficiency can be made higher. In this case, conditions of the following Equations (3) to (12) relating to the sensitivity can provide even higher relative detection-light quantity and sensitivity.

First, conditions for obtaining the high sensitivity are considered. The light-condensing efficiency of the light emitted from the emission point 1 by the condensing lens 2 can be expressed by the F-number of the condensing lens 2, F=f/D. In order to make the relative detection-light quantity 50% or more, it may necessary to set F≤2.8, that is, f≤2.8*D. On the other hand, in order to configure the condensing-lens array, since it is necessary to set p D, the following equation satisfies the condition that the relative detection-light quantity is 50% or more.

$$f \leq 2.8*p$$ [Equation 3]

Similarly, the relative detection-light quantity is set to 100% or more, 200% or more, 400% or more, and 800% or more under conditions of F≤2.0, 1.4, 1.0, and 0.7, that is, the following equations (4), (5), (6), and (7).

$$f \leq 2.0*p$$ [Equation 4]

$$f \leq 1.4*p$$ [Equation 5]

$$f \leq 1.0*p$$ [Equation 6]

$$f \leq 0.7*p$$ [Equation 7]

The above Equations (3) to (7) are met when the distance between the emission point 1 and the condensing lens 2 can be approximated by f, but more strictly it can be expressed as follows. Since the distance between the emission point 1 and the condensing lens 2 is $f^2/(g-f)+f$ when the light emitted from the emission point 1 is just focused at the optical distance g by the condensing lens 2, the effective F-number of the condensing lens 2 can be expressed as $F'=(f^2/(g-f)+f)/D$. Accordingly, the relative detection-light quantity is set to 50%, 100% or more, 200% or more, 400% or more, and 800% or more under strict conditions of the following Equations (8), (9), (10), (11), and (12).

$$f \leq (1/(2.8*p)+1/g)^{-1} \quad \text{[Equation 8]}$$

$$f \leq (1/(2.0*p)+1/g)^{-1} \quad \text{[Equation 9]}$$

$$f \leq (1/(1.4*p)+1/g)^{-1} \quad \text{[Equation 10]}$$

$$f \leq (1/(1.0*p)+1/g)^{-1} \quad \text{[Equation 11]}$$

$$f \leq (1/(0.7*p)+1/g)^{-1} \quad \text{[Equation 12]}$$

Next, conditions for obtaining the low crosstalk are considered. When the emission point images 7 of the adjacent two emission points 1 do not overlap with each other as illustrated in FIG. 3, the crosstalk does not exist. However, when the emission point images 7 of the adjacent two emission points 1 overlap with each other as illustrated in FIG. 4, the crosstalk occurs. Hereinafter, the crosstalk is expressed by a ratio X of the overlap area of the adjacent two emission point images 7 with respect to the area of the emission point image 7 in FIG. 4. The crosstalk is set to X or less under conditions as follows.

$$X=1/\pi*(\cos^{-1}(V^2/2-1)-\sin(\cos^{-1}(V^2/2-1))) \quad \text{[Equation 13]}$$

$$V \leq 2*p/d' \quad \text{[Equation 14]}$$

If Equation (14) is transformed using Equation (2), it can be expressed as follows.

$$f \geq 1/((2*p)/(V*d)+1)*g \quad \text{[Equation 15]}$$

In order to execute the detection of the light emitted from the emission point 1 to be detected without being affected by the light emitted from the adjacent emission points 1 on both sides, the distance between the two emission point images 7 is necessary to be larger than at least the radius (or half of the diameter) of the emission point image. If expressed by Equations (13) and (14), X=0.39 (39%) and V=1, whereby Equation (15) can be expressed as follows.

$$f \geq 1/(2*p/d+1)*g \quad \text{[Equation 16]}$$

In order to more effectively and independently detect the light emitted from a plurality of emission points 1, it is desirable to set the total ratio of crosstalk from both sides to 50% or less. For that purpose, if expressed by Equations (13) and (14), X=0.25 (25%) and V=1.27, whereby Equation (15) can be expressed as follows.

$$f \geq 1/(2*p)/(1.27*d)+1)*g \quad \text{[Equation 17]}$$

More desirably, it is better to set the crosstalk to 0%. For that purpose, if expressed by Equations (13) and (14), X=0 (0%) and V=2, whereby Equation (15) can be expressed as follows.

$$F \geq 1/(p/d+1)*g \quad \text{[Equation 18]}$$

As described above, it is possible to obtain a desired relative detection-light quantity and sensitivity by selecting g and f satisfying any one of Equations (3) to (12) for the given p and d. On the other hand, it is possible to obtain desired crosstalk by selecting g and f satisfying any one of Equations (16) to (18) for the given p and d. That is, it is possible to achieve both the relative detection-light quantity and the crosstalk, which share the trade-off relation, at the desired level, by selecting g and f satisfying either one of Equations (3) to (12) and either one of Equations (16) to (18).

FIG. 5 illustrates Equations (3) to (12) and Equations (16) to (18) with a horizontal axis g and a vertical axis f for the case where p=1 mm and d=0.05 mm as a typical example. The numbers illustrated in the curves or the straight lines indicate boundary lines of the corresponding Equations, a symbol ↓ (down arrow) indicates an area below the boundary line, and a symbol ↑ (up arrow) indicates an area above the boundary line. For example, in order to obtain Equation (3) satisfying the condition that the relative detection-light quantity is 50% or more, the g and f may be located at the area below the straight line ↓ (3) in FIG. 5. On the other hand, in order to obtain Equation (17) satisfying the condition that the crosstalk is 25% or less, the g and f may be located at the area above the straight line ↑ (17) in FIG. 5. That is, in order to set the relative detection-light quantity to 50% or more and to set the crosstalk to 25% or less, the g and f may be located at the area below of the straight line ↓ (3) in FIG. 5 and at the area above the straight line ↑ (17) in FIG. 5.

As is apparent from the magnitudes of g and f, the emission detection apparatus using the g and f illustrated in FIG. 5 is characterized in that not only performances of high sensitivity and low crosstalk are improved, but also the size of the apparatus can be reduced by 1 to 3 orders of magnitude compared with the detection apparatus in PTL 1 and NPTL 1. As is apparent from the above, as the p is smaller and the d is larger, the ranges of g and f satisfying the conditions of high sensitivity and low crosstalk become narrower, whereas the downsizing of the emission detection apparatus is inevitable. Conversely, as the p is smaller and the d is larger, the characteristics of the present invention becomes more useful, and the advantage thereof becomes remarkable in comparison to the conventional method. Specifically, in the case of p≤20 mm and more preferably p≤10 mm, the characteristics of the present invention becomes particularly useful. Further, in the case of d≥0.005 mm and more preferably d≥0.01 mm, the characteristics of the present invention becomes particularly useful.

Subsequently, a method of further performing the multi-color detection will be described below based on the above conditions. A color sensor is disposed at the position of the emission point image 7 in FIG. 3 or 4, so that the sensor surface is perpendicular to the optical axes of the condensing lenses 2, that is, the sensor surface is parallel to the array plane of the emission points 1 and the array plane of the condensing lenses 2. Here, the color sensor is configured such that two or more kinds of pixels capable of respectively identifying and detecting at least two kinds of light having different wavelengths are arranged. The most common color sensor is a color sensor which is used for digital cameras for general consumers. In the color sensor, three kinds of pixels for identifying three kinds of colors of R, G, and B, that is, red, green, and blue are two-dimensionally arranged. In the present invention, such a general color sensor can also be used. In recent years, a general color sensor has high sensitivity, and therefore can also be used in this technical field. The above-described color sensor is most suitable for identification of three colors, and can identify four or more colors from the intensity ratio of three kinds of pixels as performed by the digital camera. Therefore, the detection apparatus using the above-described color camera can be applied to a DNA sequencer for performing four-color detection.

However, in order to accurately perform color identification of the light emitted from the emission point 1, it is effective to make the diameter d' of the emission point image 7 larger than the size of each type of pixel. This is because it is possible to avoid the influence of variation in the relative position between the emission point image 7 and the pixels by detecting the light emitted from each emission point 1 by using a plurality of pixels for each type of pixel. Under the appropriate conditions of the present invention indicated in Equations (3) to (12) and Equations (16) to (18), m>1 in Equation (1), that is, d'>d in Equation (2) is often met, and thus it is easy to satisfy the above conditions. In addition, since the array plane of the emission points 1 and the array plane of the condensing lenses 2 are parallel to the sensor surface, it is possible to make the sensor surface approach the array plane of the condensing lenses 2, and to easily follow the conditions of Equations (3) to (12) and Equations (16) to (18).

Recently, color sensors having four kinds of pixels with IR (infrared) added to R, G, and B are commercially available, and it is useful to use such a color sensor for detecting four colors in a DNA sequencer. The plurality of types of pixels may be arranged on the same plane or may be arranged in a direction perpendicular to the sensor surface. As described above, the application of the color sensor already in practice use to the present invention is effective in terms of suppressing development costs. Naturally, it is effective to customize the number of kinds of pixels of the color sensor and the characteristics of each kind of pixel according to the purpose.

FIG. 6 illustrates an example of the multicolor detection apparatus using the color sensor. FIG. 6(a) illustrates the multicolor detection apparatus as viewed in a direction perpendicular to the plane including each optical axis of the condensing lenses 2, and FIG. 6(b) illustrates an image 12 detected by the two-dimensional color sensor 11. Here, an example where four colors are detected will be described.

As illustrated in FIG. 6(a), lights emitted from the respective emission points 1 are condensed individually by the condensing lenses 2 to form light beams 9, and are transmitted through a common longpass filter 10 in parallel, and are incident on a common two-dimensional color sensor 11 in parallel. The longpass filter 10 is provided to block excitation light, for example, light having a wavelength which is an obstacle to multicolor detection. As illustrated in FIG. 6(b), on an image 12 of the two-dimensional color sensor 11, emission point images 7 of the lights emitted from the respective emission points are formed, respectively. The two-dimensional color sensor 11 includes, for example, four kinds of pixels of an A pixel 13, which mainly detects A light-emission, a B pixel 14, which mainly detects B light-emission, a C pixel 15, which mainly detects C light-emission, and a D pixel 16, which mainly detects D light-emission, the four kinds of pixels being respectively arranged regularly in a multitude. The size of all of the pixels 13, 14, 15, and 16 is S=0.05 mm. On the other hand, when d=0.05 mm, f=1 mm, and g=10 mm and the emission points 1 are focused on the two-dimensional color sensor, m=9 from Equation (1) and d'=0.45 mm from Equation (2). That is, S <d' is satisfied, and the emission point image 7 is detected with about 64 pixels and is detected with 16 pixels per one kind of pixel.

As described above, it is possible to accurately detect four colors of the light emitted from each emission point 1 by detecting the respective emission point image 7 by a large number of four kinds of pixels . For example, even if the relative position between each kind of pixel and the emission point image 7 fluctuates, it does not matter. Alternatively, even if the light intensity distribution in the emission point image 7 is non-uniform, each of the colors can be uniformly and stably detected. In the multicolor detection apparatus illustrated in FIG. 6, the diameter d of each emission point 1, the interval p between the respective emission points 1 and between the respective condensing lenses 2, the focal length f and the effective diameter D of each condensing lens 2, and the optical distance g between each condensing lens 2 and the sensor 11 satisfy any one of Equations (3) to (7), Equations (8) to (12), and Equations (16) to (18), the predetermined high sensitivity and low crosstalk are accomplished, and the size and cost of the detection apparatus are reduced.

On the other hand, in the case of using a color sensor in which plural kinds of pixels are arranged on the same plane as illustrated in FIG. 6, there is a problem that the utilization efficiency of the incident light is low. For example, as illustrated in FIG. 6, when four colors are identified by the color sensor in which four kinds of pixels are arranged, the utilization efficiency of the incident light becomes 1/4 or less. This may be an obstacle in performing light-emission detection with higher sensitivity. The utilization efficiency of the incident light may be improved using the color sensor in which a plurality of kinds of pixels are arranged in the direction perpendicular to the sensor surface, but such a color sensor is not still used in general. Therefore, another multicolor detection method with high utilization efficiency of the incident light is proposed below.

One way of increasing the use efficiency of the incident light is a method of using one or more types of dichroic mirrors. A dichroic mirror has a multilayer film formed on a front surface of at least one side of a transparent substrate such as glass to make reflected light and transmitted light of light incident at 45° in general to be lights in different wavelength bands, thereby utilizing both the reflected light and the transmitted light to increase use efficiency of the incident light. Generally, it is possible to detect up to two colors by one kind of dichroic mirror, to detect up to three colors by combining two kinds of dichroic mirrors, and similarly to detect up to (n+1) colors by combining N kinds of dichroic mirrors. In addition to the above dichroic mirrors, bandpass filters, color glass filters, or total reflection mirrors are often used in combination. In some of digital video cameras for general consumers, two kinds of dichroic mirrors and three CCDs are combined to detect three colors. In addition, NPTL 1 is an example in which three kinds of dichroic mirrors and four CCDs are combined to detect four colors. As described above, in the methods of using the dichroic mirrors a plurality of sensors are often used because the reflected light and the transmitted light have different traveling directions. This conflicts with reduction in size and cost of the detection apparatus which is an object of the present invention.

FIG. 7 illustrates an example of a multicolor detection apparatus in which these problems are solved. FIG. 7(a) illustrates the multicolor detection apparatus as viewed in a direction perpendicular to a plane including respective optical axes of the condensing lenses 2, FIG. 7(b) illustrates a cross-section of the multicolor detection apparatus including the optical axis of one condensing lens and perpendicular to the arrangement direction of the condensing-lens array, and FIG. 7(c) illustrates an image detected by a two-dimensional sensor 30. Here, an example in which four colors are detected will be described.

For example, the lights emitted from the respective emission points 1 of the four emission-point array are respectively condensed by the individual condensing lenses 2 to form light beams 9, and are transmitted through the common longpass filter 10 in parallel. This is the same as in FIG. 6. Here, a dichroic-mirror array in which four common four kinds of dichroic mirrors 17, 18, 19, and 20 are arranged side by side is used as illustrated in FIG. 7(b). The light beams 9 are made incident in parallel on respective dichroic mirrors 17 to 20, are divided into four color beams 21, 22, 23, and 24 in the direction perpendicular to the emission-point array direction, and the four color beams 21 to 24 emitted from each emission point 1 travel in the same direction as the light beam 9, that is, the optical axis direction of the condensing lens 2 and are made incident in parallel on a common two-dimensional sensor 30 to form emission point images 25, 26, 27, and 28. Here, the dichroic mirror 20 may be replaced by a total reflection mirror, but for the sake of simplicity, it is called a dichroic mirror 20.

As illustrated in FIG. 7(c), on the image 29 of the two-dimensional sensor 30, sixteen emission point images 25 to 28 obtained by four-division of the lights emitted from four emission points 1 are collectively observed. Here, light beams passing through the dichroic mirror 17 are light beams 21, light beam reflected by the dichroic mirrors 17 and 18 are light beams 26, light beams reflected by the dichroic mirror 17, passing through the dichroic mirror 18, and reflected by the dichroic mirror 19 are light beams 23, and light beams reflected by the dichroic mirror 17, passing through the dichroic mirrors 18 and 19, and reflected by the dichroic mirror 20 are light beams 24. By designing and controlling transmission characteristics and reflection characteristics of the longpass filter 10 and the dichroic mirrors 17 to 20, the light beams 21 have mainly an A-fluorescence component, the light beams 22 have mainly a B-fluorescence component, the light beams 23 have mainly a C-fluorescence component, and the light beams 24 have mainly a D-fluorescence component, and by detection of intensities of the emission point images 25, 26, 27, and 28, the fluorescence of A, B, C, and D can be measured.

Although wavelength bands of the light beams 21, 22, 23, and 24 may be arbitrarily designed, the dichroic mirrors 17 to 20 are easily designed when these light beams are arranged in order of wavelength. That is, the order may be a center wavelength of the A-fluorescence >a center wavelength of the B-fluorescence >a center wavelength of the C-fluorescence >a center wavelength of the D-fluorescence, or a center wavelength of the A-fluorescence <a center wavelength of the B-fluorescence <a center wavelength of the C-fluorescence <a center wavelength of the D-fluorescence. Although not illustrated in FIG. 7, a band pass filter or a color glass filter having different spectral characteristics may be disposed at least one position of the light beams 21, 22, 23, and 24, to effectively supplement or enhance spectral characteristics of the dichroic mirrors 17 to 20. Further, although not illustrated in FIG. 7, it is effective to provide irradiation light such as excitation light for causing the emission point 1 to emit light. If such irradiation light is irradiated from the direction perpendicular to the optical axes of the condensing lenses 2 without using the condensing lenses 2, irradiation light incident on the sensor through the condensing lens 2 can be reduced, which is advantageous in terms of sensitivity. Further, the longpass filter 10 maybe replaced by a dichroic mirror different from the dichroic mirrors 17 to 20, and then the irradiation lights may be reflected by the above dichroic mirror, focused by the condensing lenses 2, and individually irradiated to the emission points 1. Then the lights emitted from the emission points 1 may be condensed by the condensing lenses 2, transmitted through the above dichroic mirror and detected by the multicolor detection apparatus similar to that illustrated in FIG. 7. That is, it is effective to adopt a so-called epi-fluorescence illumination configuration.

In the multicolor detection apparatus illustrated in FIG. 7, the diameter d of each emission point 1, the interval p between the respective emission points 1 and between the respective condensing lenses 2, the focal length f and the effective diameter D of each condensing lens 2, and the optical distance g between each condensing lens 2 and the sensor 30 satisfy any one of Equations (3) to (7), Equations (8) to (12), and Equations (16) to (18), and thus high sensitivity and low crosstalk are accomplished and the size and cost of the detection apparatus are reduced. Here, the following features (1) to (10) summarize features for reducing the size and cost of the multicolor detection apparatus using the dichroic-mirror array illustrated in FIG. 7. All of these features are not necessary to be satisfied, and it is effective to satisfy any one of them.

(1) For M emission points of the emission-point array, M light beams obtained by condensing light emitted from each emission point using the condensing-lens array are divided into N color beams having different wavelength components, respectively, and each of color beams travels in the same direction.

(2) For M emission points of the emission-point array, M light beams obtained by condensing light emitted from each emission point using the condensing-lens array are divided into N color beams having different wavelength components, respectively, and each of color beams travels in the optical axis direction of each condensing lens.

(3) For M emission points of the emission-point array, M light beams obtained by condensing light emitted from each emission point using the condensing-lens array are divided into color beams with different wavelength components, and the direction of the division is perpendicular to the arrangement direction of the emission-point array and the condensing-lens array.

(4) For M emission points of the emission-point array, M light beams obtained by condensing light emitted from each emission point using the condensing-lens array are divided into color beams with different wavelength components, and the direction of the division is perpendicular to the optical axis of each condensing lens.

(5) For M emission points of the emission-point array, M light beams obtained by condensing light emitted from each emission point using the condensing-lens array are divided, using N dichroic mirrors, into color beams with different wavelength components, and the N dichroic mirrors are arranged in the direction perpendicular to the arrangement direction of the emission-point array and the condensing lens array.

(6) For M emission points of the emission-point array, M light beams obtained by condensing light emitted from each emission point using the condensing-lens array are divided, using N dichroic mirrors, into color beams with different wavelength components, and the N dichroic mirrors are arranged in the direction perpendicular to the optical axis of each condensing lens.

(7) For M emission points of the emission-point array, M light beams obtained by condensing light emitted from each emission point using the condensing-lens array are divided into N color beams with different wavelength components to have (M×N) color beams, and then (M×N) color beams are directly incident on the sensor in parallel without being re-condensed.

(8) For M emission points of the emission-point array, the optical axis of each condensing lens of the condensing-lens array for condensing light emitted from each emission point is made perpendicular to the sensor surface.

(9) N dichroic mirrors with different spectroscopic characteristics are provided, and each dichroic mirror with a spectroscopic characteristic is constituted by a single member. M light beams obtained by indivisually condensing lights emitted from M emission points of the emission-point array are incident on the respective dichroic mirrors in parallel.

(10) M light beams obtained by individually condensing lights emitted from M emission points of the emission-point array are divided into N color beams with different wavelength components, respectively, to have (M×N) color beams, and then (M×N) color beams are incident on the single sensor in parallel.

The above description was made with respect to the case where the respective light beams obtained by condensing the lights emitted from the emission-point array using the respective condensing lenses of the condensing-lens array are directly incident on the sensor without being re-condensed by another lenses other than the condensing lenses. Hereinafter, a case will be described in which the respective light beams obtained by condensing the lights emitted from the emission-point array using the respective condensing lenses of the condensing-lens array are incident on the sensor after being re-condensed by another lenses other than the condensing lenses. Hereinafter, a lens for re-condensing each light beam is called a re-condensing lens.

In the derivation of Equations (1) to (18), the optical distance between the condensing lens and the sensor is defined as g, but in a case of using the re-condensing lens, if the optical distance between the condensing lens and the re-condensing lens is g, Equations (1) to (18) can be used as conditions for high sensitivity and low crosstalk. That is, in FIG. 3 or 4, the position of the emission point image 7 may be regarded as a position of the re-condensing lens, but is not the position of the sensor. This is because, if the conditions of high sensitivity and low crosstalk are not satisfied at the position of the re-condensing lens (for example, if the overlap of the adjacent light beams is too large), the performance of high sensitivity and low crosstalk will not be improved irrespective of the configuration after the re-condensing lens. At the position of the optical path length g from the condensing lens, the same number of re-condensing lenses as the condensing lenses are aligned with a interval p so that the optical axes of the paired condensing lens and the re-condensing lens are made to coincide. When the effective diameter of the re-condensing lens is set to be "D" which is equal to the effective diameter of the condensing lens, the loss of the detection-light quantity due to the re-condensing lens can be prevented and a re-condensing-lens array can be configured. The sensor is located at a subsequent stage of the re-condensing lenses, and is disposed at a position at which the optical path length from the condensing lens is larger than g. In this way, it can be seen that the conditions for realizing high sensitivity and low crosstalk in FIG. 3 or 4 are established even when the re-condensing lens is used.

FIG. 8 is a schematic diagram of the multicolor detection apparatus using a wavelength dispersion element and a re-condensing-lens array. FIG. 8(a) is a schematic diagram of the multicolor detection apparatus as viewed in a direction perpendicular to a plane including each optical axis of the condensing lens 2, FIG. 8(b) is a schematic sectional view of the multicolor detection apparatus which includes optical axes of one condensing lens 2 and paired re-condensing lens 33 and is perpendicular to the arrangement directions of the condensing-lens array and the re-condensing-lens array, and FIG. 8(c) illustrates an image 42 detected by a two-dimensional sensor 37. Here, an example of performing three-color detection is illustrated.

As illustrated in FIG. 8(a), the lights emitted from the emission points 1 are individually condensed by the condensing lenses 2 to form light beams 9 and are transmitted through the longpass filter 10 in parallel. These operations are the same as in FIG. 6. Thereafter, as illustrated in FIG. 8(b), the respective light beams 9 are incident in parallel on a common transmission-type diffraction grating 31, which is the wavelength dispersion element, to be subjected to wavelength dispersion in a direction perpendicular to the emission-point array direction, to be individually re-condensed by the re-condensing lenses 33, and to be made incident in parallel on the two-dimensional sensor 37. Here, light beams 34, 35, and 36 indicate light beams having center wavelengths of A-, B-, and C-fluorescence, respectively. As illustrated in FIG. 8(c), a wavelength-dispersed image 41 of the light emitted from each emission point 1 can be obtained on the image 42 of the two-dimensional sensor 37. Here, images 38, 39, and 40 in the wavelength-dispersion spectral image 41 indicate images of the light beams having the center wavelengths of A-, B-, and C-fluorescence, respectively.

In the multicolor detection apparatus illustrated in FIG. 8, the diameter d of each emission point 1, the interval p between the respective emission points 1 and between the respective condensing lenses 2, the focal length f and the effective diameter D of each condensing lens 2, and the optical distance g between each condensing lens 2 and corresponding re-condensing lens 33 satisfy any one of Equations (3) to (7), Equations (8) to (12), and Equations (16) to (18), and thus high sensitivity and low crosstalk are accomplished and the size and cost of the detection apparatus are reduced.

FIG. 8 illustrates that in the case of using the re-condensing lens, it is better to satisfy any one of Equations (3) to (7), Equations (8) to (12), and Equations (16) to (18) as the optical distance g between the condensing lens and the re-condensing lens. Similarly, it is effective to satisfy any one of Equations (3) to (7), Equations (8) to (12), and Equations (16) to (18) by arranging the optical element for allowing the respective light beams to travel in different directions or the optical element for enlarging the interval of the respective light beams at (the position at which the optical distance from the condensing lens for individually condensing the light emitted from each of emission points of the emission-point array to form the light beams is g).

For example, in FIG. 9, a prism 43 is disposed, as the optical element, at a subsequent stage of the longpass filter 10 in FIG. 6, respective light beams 9 are detected by being incident on a common two-dimensional color sensor 11 in parallel after traveling in different directions. FIG. 9(a) illustrates the multicolor detection apparatus as viewed in a direction perpendicular to a plane including each optical axis of the condensing lens 2, and FIG. 9(b) illustrates an image 12 detected by the two-dimensional color sensor 11. The prism 43 changes a direction and an angle of refraction of each light beam 9 depending on incident positions of the light beam 9, and enlarges the interval of each light beam 44 after the refraction. Assuming that the optical distance between the condensing lens 2 and the prism 43 is g, Equations (1) to (18) directly becomes conditions of high sensitivity and low crosstalk. In addition, since the interval between the emission point images 45 on the image 12 of the two-dimensional color sensor is enlarged compared with the case of FIG. 6, it is possible to avoid an increase in crosstalk and to independently detect the lights emitted from the respective emission points 1 with ease. Further, since the interval between the emission point images 45 is large, it is not necessary for the sensor to be a common two-dimensional color sensor as illustrated in FIG. 9, and each light beam 44 can also be detected by an individual color sensor. When the prism 43 is applied to the configuration of FIG. 7, the prism 43 may be disposed between the longpass filter 10 and the dichroic-mirror array. Since the optical path length between the condensing lens 2 and the prism 43 can be made smaller than the optical path length between the condensing lens 2 and the two-dimensional sensor 30, the condition of low crosstalk is further easily satisfied. Although the interval between the emission point images in the light-beam division direction (the interval between the emission point images 25 to 28) in FIG. 7(c) does not change, since the interval between the emission point images in the emission-point array direction increases, the crosstalk is easily reduced.

As described above, the configuration of the apparatus is simplified by commonly using each optical element such as the dichroic mirror, the filter, the total reflection mirror, the diffraction grating, and the sensor for the plurality of emission points and moreover implementation of each optical element is facilitated. In addition, the overall size of the detection apparatus is reduced. Further, according to the above configuration, the detection efficiency and the spectroscopic accuracy are equal for each emission point, and variations in sensitivity and color identification can be reduced.

FIG. 10 illustrates an example in which optical fibers 46 are disposed as optical elements at the subsequent stage of the longpass filter 10 in FIG. 6. The light beams 9 are respectively made to incident to incident ends of the individual optical fibers 46 and are emitted from emission ends thereof. Here the intervals between the emission ends are larger than the intervals between the incident ends. Then, emitted light beams 47 from the emission ends are detected by being incident on a common two-dimensional color sensor 11 in parallel. FIG. 10(a) illustrates the multicolor detection apparatus as viewed in a direction perpendicular to a plane including each optical axis of the condensing lens 2, and FIG. 10(b) illustrates an image 12 detected by the two-dimensional color sensor 11.

If the optical distance between the condensing lens 2 and the incident end of the optical fiber 46 is g, Equations (1) to (18) directly become conditions of high sensitivity and low crosstalk. In addition, since the interval between the emission point images 48 on the image 12 of the two-dimensional color sensor 11 is enlarged compared with the case of FIG. 6, it is possible to avoid an increase in crosstalk and to independently detect the lights emitted from the respective emission points 1 with ease. Further, since the interval between the emission point images 48 is large, it is not necessary for the sensor to be a common two-dimensional color sensor as illustrated in FIG. 10, and each light beam 47 can also be detected by an individual color sensor. When the optical fibers 46 are applied to the configuration of FIG. 7, the incident ends of the optical fibers 46 may be disposed at the position of the two-dimensional sensor 30 in FIG. 7, that is, at the subsequent stage of the dichroic-mirror array. Further, the optical fibers 46 can correspond to all of the emission point images 25 to 28 in FIG. 7(c). This makes it possible to arbitrarily set the interval and arrangement of the emission point images 25 to 28, and thus it is easy to detect the these images with the individual sensors or to detect them with a desired one-dimensional sensor or two-dimensional sensor.

Examples of the present invention will be described below.

EXAMPLE 1

FIG. 11 is a schematic diagram illustrating an apparatus configuration example of a capillary array DNA sequencer. Referring to FIG. 11, an analytical procedure will be described. First, sample-injection ends 50 of a plurality of capillaries 49 (four capillaries 49 are illustrated in FIG. 11) are immersed in a cathode-side buffer solution 60, and sample elution ends 51 are connected to an anode-side buffer solution 61 through a polymer block 55. First, a valve 57 of the pump block 55 is closed, a polymer solution inside the pump block 55 is pressurized by a syringe 56 connected to the pump block 55, and the polymer solution is filled into insides of respective capillaries 49 from the sample-elution ends 51 in a direction of the sample-ejection ends 50. Next, the valve 57 is opened, and different samples are injected into the respective capillaries 49 from the sample injection ends 50, after which a high voltage is applied between a cathode electrode 58 and an anode electrode 59 by using a power source 62, thereby starting capillary electrophoresis. DNA fragments labeled by fluorescent substances of four colors electrophoretically migrate from the sample injection ends 50 to the sample elution ends 51.

A part of a coating of each capillary 49 at position (laser-irradiation position 52) where the DNA fragments electrophoretically migrate a fixed distance from the sample-injection end 50 in each capillary 49 is removed, such that the laser-irradiation positions 52 of the capillaries 49 are arrayed on the same plane (array plane), and are simultaneously irradiated by a laser beam 54 that is oscillated from a laser-light source 53, focused by a lens, and introduced along the array plane from a side of the array plane. The DNA fragments labeled by the fluorescent substances of the four colors electrophoretically migrate inside each capillary 49, and the fluorescent substances are excited and emit fluorescence when the DNA fragments pass across the laser-irradiation position 52. Lights (fluorescences) emitted from the insides of the capillaries 49 forms a emission-point array, and each emitted light (fluorescence) is detected by the multicolor detection apparatus illustrated by FIGS. 6 to 10 from a direction perpendicular to the array plane (direction perpendicular to a paper surface in FIG. 11).

In the example, a case, in which the multicolor detection apparatus using a dichroic-mirror array is used for the capillary DNA sequencer illustrated in FIG. 11, will be described in detail. The laser irradiation-positions 52 of the four capillaries 49 having an outer diameter of 0.36 mm and an inner diameter of 0.05 mm are arrayed on the same plane (array plane) with an interval of p=1 mm, and the laser beam 54 narrowed to a diameter of 0.05 mm is incident on a side of the array plane to irradiate the four capillaries 49 at the laser irradiation-positions 52, thereby obtaining a emission-point array in which four (M=4) of the emission points 1 with an effective diameter of d=0.05 mm are arrayed at the interval of p=1 mm. Here, the effective diameter of the emission point coincides with the inner diameter of the capillary 49. It is set that the wavelength of the laser beam 54 is 505 nm and the fluorescences of four colors (maximum emission wavelengths) are A fluorescence (540 nm), B fluorescence (570 nm), C fluorescence (600 nm), and D fluorescence (630 nm). The entire width of the emission-point array is set as W=p*(M−1)=3 mm. The light emitted from each emission point 1 is individually condensed by each condensing lens 2 of a condensing-lens array 8 in which four condensing lenses 2 having a focal distance of f=1.5 mm and the effective diameter of D=1 mm are arrayed at the intervals of p=1 mm. The above-mentioned d, p, f, and D are basically equal among the emission points and the condensing lenses, but are not necessarily required to be equal. In this case, d, p, f, and D are average values of a plurality of the emission points and the condensing lenses.

FIG. 12 is a cross-sectional diagram illustrating the multicolor detection apparatus. The cross-sectional diagram includes an optical axis of one condensing lens 2, and the paper plane thereof is perpendicular to an array direction of the condensing-lens array 8. Meanwhile, FIG. 12 is different from FIG. 7 in that the optical axis of each condensing lens 2 and a propagating direction of each divided light beams (color beams) by the dichroic-mirror array are vertical, that is, the optical axis of each condensing lens 2 is parallel to a sensor surface of the two-dimensional sensor 30. Other configurations are same as those of FIG. 7. However, the emission points 1 are omitted in FIG. 12.

The longpass filter 10 having a width of $\alpha=5$ mm, a thickness of $\beta=1$ mm, and a depth of $\gamma=5$ mm is disposed at a position of a distance of 3 mm apart from the condensing lens 2, such that a normal line thereof and the optical axis of the condensing lens 2 are parallel to each other. Further, the dichroic mirrors 17, 18, 19 and 20 are arranged at intervals of 5 mm, so that the normal line thereof is inclined at 45 degrees with respect to the optical axis of the condensing lens 2. Each dichroic mirror is composed of a quartz substrate (refractive index $n_0=1.46$), on a lower right front surface of which a multilayer film or a monolayer film is formed. The quartz substrate has a width of $\alpha=5$ mm, a thickness of $\beta=1$ mm, and a depth of $\gamma=5$ mm. In the same manner as those of FIG. 7, the dichroic mirror 20 may be replaced with a total reflection mirror. FIG. 12 illustrates a side surface of $\alpha \times \beta$ of both the longpass filter 10 and the dichroic mirrors 17 to 20, and y is in a direction perpendicular to the paper surface of FIG. 12. Further, an antireflection film for reducing reflection loss is formed on an upper left front surface of each of the dichroic mirrors 17, 18, and 19. Moreover, a light shielding film for preventing penetration of light is formed on each of all side-surfaces of the dichroic mirrors 17, 18, 19 and 20 in order to prevent an unintended stray light. A right end of the dichroic mirror 17 is disposed at a position of a distance of 5 mm apart from the condensing lens 2 (that is, a position of a distance of 2 mm apart from the longpass filter 10). Upper and lower ends of the dichroic mirrors 17, 18, 19 and are respectively disposed on the same planes. The two-dimensional sensor 30 is disposed at a position of a distance of 5 mm apart from the lower ends of the dichroic mirrors 17, 18, 19 and 20. All of the optical system elements are disposed in the air. The arrangement thereof in the air is performed to improve spectral performances of the dichroic mirrors.

Eleven light beam elements 65 illustrated in FIG. 12 shows that the above-described dichroic-mirror array can divide incident a parallel light beam into four light beams according to a designed configuration. The eleven light beam elements 65 illustrate the light beam when the width of the light beam becomes maximum, and illustrate results of calculation of optical paths thereof by using laws of reflection and refraction. Thereafter, the maximum width of the light beam is referred to as an aperture width 63 of the dichroic-mirror array, and a size thereof is described by W. The aperture width represents the maximum width of the light beam that can be fully divided by the dichroic-mirror array according to the designed configuration. The aperture width W is generally different from a width d' (s) of the light beam obtained by condensing the light emitted from the emission point 1 by using the condensing lens 2, where d' (s) is a function of the optical path length s from the condensing lens 2. Further, d'(s) is the width of an actual light beam, and W represents a maximum value of the width of the light beam that can be accepted by the multicolor detection apparatus under a provided condition. That is, it is desirable that Wdy(s) is set for dividing the light beam condensed by the condensing lens 2 without loss of the light quantity. Further, it is desirable that as W is larger, because tolerance with respect to deviation between a center axis of the light beam condensed by the condensing lens 2 and a center axis of the aperture width 63 increases. The eleven light beam elements 65 propagating to the left direction from the condensing lens 2 are formed to have an equal interval, and to be parallel to each other.

As illustrated in FIG. 12, when passing through respective dichroic mirrors 17 to 19, respective light beam elements 65 are sequentially shifted in parallel to an upper side by internal refraction in respective dichroic mirrors 17 to 19. In order to reduce the above-described influence, the optical axis of the condensing lens 2 and the center light beam element emitted from the condensing lens are disposed on a lower side than a center of a lower right front surface of the dichroic mirror 17. Meanwhile, the optical path length s, which is an optical distance between the condensing lens 2 and the two-dimensional sensor 30, is different for the four divided light beams, as is clear from FIG. 12. Then, the light beam that transmits the dichroic mirrors 17 to 19, and is reflected by the dichroic mirror 20 provides the longest optical path length 64. Hereafter, when a plurality of the optical paths exist between the condensing lens and the sensor, the longest optical path length 64 among them is defined as an optical path length of the light-detection apparatus and the length thereof is represented as g. In the multicolor detection apparatus illustrated in FIG. 12, the aperture width 63 is calculated as W=2.1 mm and the optical path length 64 is calculated as g=29 mm. The above-mentioned W and g are basically equal among the emission points and the condensing lenses, but are not necessarily required to be equal. In this case, W and g are average values for a plurality of the emission points and the condensing lenses.

An optical distance between the emission point 1 and the condensing lens 2 having a focal distance of f=1.5 mm is set as about 1.58 mm. This causes the light emitted from the emission point 1 to be just focused at an optical distance g=29 mm from the condensing lens 2, with an image magnification of m=18.3 by Equation (1), and the diameter of the emission point image 7 of the emission point 1 having a diameter of d=0.05 mm to be d'=0.92 mm by Equation (2). Since the effective diameter of D=1 mm of the condensing lens is greater than the diameter d', d'(s)≤1 mm where 0 mm≤s≤29 mm, and then d'(s) ≤W=2.1 mm where 0 mm≤s≤29 mm. Therefore, the light beam divided into four light beams by the dichroic mirrors 17 to 20 can reach the two-dimensional sensor 30 without loss.

In the above-described multicolor detection apparatus, Equations (4), (9), and (18) are satisfied, and it is found out that a relative detection-light quantity can be greater than 100%, a strict relative detection-light quantity can be greater than 100%, crosstalk can be 0%, and therefore a condition for high sensitivity and low crosstalk can be obtained. As illustrated in FIG. 12, a size of the multicolor detection apparatus can be smaller than a volume (668 mm$^2$) of a rectangular parallelepiped which is specified by a total width AW=3 mm of the emission-point array, a width of 24.2 mm in an optical axis direction of the condensing lens 2, and a width of 9.2 mm in a vertical direction with respect to the optical axis of the condensing lens 2 and an array direction of the emission-point array. That is, a size of the fluorescence detection apparatus can be reduced to 1/2, 400 of the size in the case disclosed in PTL 1. Further, since all of the optical elements to be used are fine, a large cost can be reduced. The above-described m and d' are basically equal among the emission points and the condensing lenses, but are not necessarily required to be equal. In this case, m and d' are average values for a plurality of the emission points and the condensing lenses.

EXAMPLE 2

In the multicolor detection apparatus illustrated in FIG. 12 according to Example 1, since all of the array directions of the dichroic-mirror array, the condensing-lens array, and the emission-point array are parallel to the sensor surface of the two-dimensional sensor 30, interference does not occur therebetween. However, since the array planes of the respective capillaries 49 of the capillary array are perpendicular to the sensor surface of the two-dimensional sensor 30, an apparatus configuration has a drawback in that the interference therebetween may occur. Here, proposed herein is a multicolor detection apparatus for solving the above-described drawback according to the example.

In the capillary DNA sequencer, the configurations from the capillary array to the condensing-lens array are the same as those of the Example 1, and the configuration of FIG. 12 is replaced with a configuration of FIG. 13. FIG. 13 is a cross-sectional diagram schematically illustrating a multicolor detection apparatus. The cross-sectional diagram includes an optical axis of one condensing lens 2, and the paper plane thereof is perpendicular to the array direction of the condensing-lens array 8, and the optical axis of each condensing lens 2 is parallel to a propagating direction of the divided light beams (color beams)by the dichroic-mirror array , that is, the optical axis of each condensing lens 2 and the sensor surface of the two-dimensional sensor 30 are set to be vertical, which is the same as those of FIG. 7. The longpass filter 10 having a width of $\alpha=5$ mm, a thickness of $\beta=1$ mm, and a depth of $\gamma=5$ mm is disposed at a position of a distance of 3 mm apart from each condensing lens 2, such that a normal line thereof and the optical axis of each condensing lens 2 are parallel to each other. Further, the dichroic mirror 17 is composed of a quartz substrate (refractive index $n_0=1.46$), on an upper left front surface of which a multilayer film is formed. On the other hand, each of the dichroic mirrors 18, 19 and 20 is composed of a quartz substrate, on a lower right front surface of which a multilayer or the monolayer film is formed. Each of the quartz substrates has a width of $\alpha=5$ mm, a thickness of $\beta=1$ mm, and a depth of $\gamma=5$ mm. The dichroic mirrors 17, 18, 19 and 20 are arranged at intervals of 5 mm, such that the normal line thereof is inclined at 45 degrees with respect to the optical axis of each condensing lens 2. Further, a light shielding film for preventing penetration of light is formed on each of all side-surfaces of the dichroic mirrors 17, 18, 19 and 20 in order to prevent the unintended stray light.

An upper end of the dichroic mirror 17 is disposed at a position of a distance of 5 mm apart from the condensing lens 2. Upper and lower ends of the dichroic mirrors 17, 18, 19 and 20 are respectively disposed on the same planes. The two-dimensional sensor 30 is disposed at a position of a distance of 5 mm apart from the lower ends of the dichroic mirrors 17, 18, 19 and 20. In the same manner as that of FIG. 12, eleven light beam elements 65 are illustrated. As a result, in the multicolor detection apparatus illustrated in FIG. 13, the aperture width 63 is calculated as W=1.7 mm and the optical path length 64 is calculated as g=28 mm, based on which the same performance as that of FIG. 12 can be achieved.

An optical distance between the emission point 1 and the condensing lens 2 is set as about 1.58 mm. This causes the light emitted from the emission point 1 to be just focused at an optical distance g=28 mm from the condensing lens 2, with an image magnification of m=17.7 and the diameter of the emission point image 7 to bed'=0.88 mm Since the effective diameter of D=1 mm of the condensing lens is greater than the diameter d', d'(s)≤1 mm where 0 mm≤s≤28, and then d'(s)≤W=1.7 mm where 0 mm≤s≤28. Therefore, the light beam divided into four light beams by the dichroic mirrors 17 to 20 can reach the two-dimensional sensor 30 without loss.

In the above-described multicolor detection apparatus, Equations (4) and (9), and (18) are satisfied, and it is found out that the relative detection-light quantity can be greater than 100%, the strict relative detection-light quantity can be greater than 100%, the crosstalk can be 0%, and therefore a condition for high sensitivity and low crosstalk can be obtained. A size of the multicolor detection apparatus can be smaller than a volume (818 mm$^2$) of a rectangular parallelepiped which is specified by a total width AW=3 mm of the emission-point array, a width of 14.2 mm in an optical axis direction of the condensing lens 2, and a width of 19.2 mm in a vertical direction with respect to the optical axis of the condensing lens 2 and an array direction of the emission-point array. That is, a size of the fluorescence detection apparatus can be reduced to 1/2,000 of the size in the case disclosed in PTL 1. Further, since all of the optical elements to be used are fine, a large cost can be reduced.

In the multicolor detection apparatus illustrated in FIG. 13, since the array directions of the dichroic-mirror array, the condensing-lens array, the emission-point array, and the array plane of the capillary array are all parallel to the sensor surface of the two-dimensional sensor 30, interference thereof does not occur therebetween, such that implementations thereof become easy.

EXAMPLE 3

The inner diameter of each capillary 49, that is, the diameter of the emission point 1 set as d=0.05 mm in Examples 1 and 2 is expanded to d=0.075 mm. The light emitted from the emission point 1 is just focused at an optical path length g=28 mm by using the multicolor detection apparatus illustrated in FIG. 13 in such a manner that an image magnification is set to m=17.7 and the diameter of the emission point image 7 is set to d'=1.33 mm. Since the diameter d' is greater than the effective diameter of D=1 mm of the condensing lens, d' (s)≤1.33 mm where 0 mm≤s≤28 mm, and then and d' (s) ≤W=1.7 mm where 0 mm≤s≤28 mm. Therefore, in the same manner as that of FIG. 13, the light beam divided into four light beams by the dichroic mirrors 17 to 20 can reach the two-dimensional sensor 30 without loss.

However, in the above-mentioned multicolor detection apparatus, it is found out that Equations (4) and (9) are satisfied in the same manner as that of FIG. 13. However, Equation (18) is not satisfied, and Equation (17) are satisfied. Accordingly, the relative detection-light quantity can be greater than 100%, the strict relative detection-light quantity can be greater than 100%, and therefore a condition for high sensitivity can be obtained. On the other hand, the crosstalk can be equal to or less than 25%. Although a condition for low crosstalk can be obtained, the crosstalk is higher than that of FIG. 13. Then, in this example, the optical path length g is shortened, such that the image magnification m and the diameter d' of the emission point image 7 are reduced, and further the crosstalk is lowered. In order to shorten the optical path length g, it is considered to be effective to reduce the sizes and array intervals of the respective dichroic mirrors 17 to 20.

As shown in FIG. 14, regarding the longpass filter 10 and the dichroic mirrors 17 to 20 in FIG. 13, the width $\alpha$, the thickness $\beta$, and the depth $\gamma$ is reduced from $\alpha=5$ mm, $\beta=1$ mm, and y=5 mm to $\alpha=2.5$ mm, $\beta=1$ mm, and $\gamma=5$ mm. Further, the array intervals of the respective dichroic mirrors 17 to 20 are reduced from x=5 mm to x=2.5 mm.

In this case, a position of a left end of the dichroic mirror 17 coincides with a position of a right end of the dichroic mirror 18 in a lateral direction (direction perpendicular to the optical axis of the condensing lens 2) in FIG. 14. In the same manner, a position of a left end of the dichroic mirror 18 and a position of a right end of the dichroic mirror 19 in a lateral direction, and a position of a left end of the dichroic mirror 19 and a position of a right end of the dichroic mirror 20 in a lateral direction respectively coincide with each other. Other conditions are the same as those of FIG. 13. FIG. 14 is at the same scale as FIG. 13.

As a result, the optical path length 64 can be reduced from g=28 mm to g=19 mm. Accordingly, the image magnification m=11.7 is given by the equation (1), and the diameter of the emission point image d'=0.88 mm is given by Equation (2), and Equations (4), (9), and (18) are satisfied. That is, the relative detection-light quantity can be greater than 100%, the strict relative detection-light quantity can be greater than 100%, the crosstalk can be equal to 0%, and therefore a condition for high sensitivity and low crosstalk can be obtained. However, it has become clear that the aperture width 63 is greatly reduced from W=1.7 mm to W=0.03 mm. That is, it turned out that it is impossible for the light beam condensed by the condensing lens 2 to reach the two-dimensional sensor 30 without loss. Specifically, since a relative ratio of the thickness of $\beta=1$ mm of each dichroic mirror to the reduced size of each dichroic mirror and the interval thereof increases, an influence of the light beam which is sequentially shifted in parallel to the upper side by the internal refraction in respective dichroic mirrors cannot be ignored.

Here, as illustrated in FIG. 15, in order to overcome the above-described influence, the arrangement of the dichroic mirrors 17 to 20 are changed from the same-plane arrangement to a stepwise arrangement. That is, the relative positions of the dichroic mirrors 17 to 20 in the optical axis direction of the condensing lens 2 are respectively shifted from the same-plane to compensate the above-described influence. Hereinafter, differences in comparison with FIG. 14 will be described. First, the upper end of the dichroic mirror 17 is disposed at a position of a distance of 6.3 mm apart from the condensing lens 2. Next, the lower end of the dichroic mirror 18 is shifted to a side opposite to a propagating direction of a light beam that transmits the dichroic mirror 17, that is, shifted to the upper side illustrated in FIG. 15 by y=0.7 mm in comparison with the lower end of the dichroic mirror 17. Then, the lower end of the dichroic mirror 19 is shifted to a side opposite to a propagating direction of a light beam reflected by the dichroic mirror 18, that is, shifted to the upper side illustrated in FIG. 15 by z=0.3 mm in comparison with the lower end of the dichroic mirror 18. Finally, the lower end of the dichroic mirror 20 is shifted to a side opposite to a propagating direction of a light beam reflected by the dichroic mirror 19, that is, shifted to the upper side in FIG. 15 by z=0.3 mm in comparison with the lower end of the dichroic mirror 19.

As a result, it is found out that the aperture width 63 can be greatly expanded from W=0.03 mm of FIGS. 14 to W=1.3 mm. On the other hand, since the optical path length 64 slightly increases to g=21 mm in comparison with FIG. 14, the image magnification m=13 is given by Equation (1) and the diameter of the emission point image d'=0.98 mm is given by Equation (2). Since the effective diameter of D=1 mm of the condensing lens is greater than the diameter d', d' (s)≤1 mm where 0 mm≤s≤21 mm, and then and d'(s) ≤W=1.3 mm where 0 mm≤s≤21 mm. Accordingly, the light beam divided into four light beams by the dichroic mirrors 17 to 20 can reach the two-dimensional sensor 30 without any loss.

In the above-described multicolor detection apparatus, Equations (4), (9), and (18) are satisfied in the same manner as that of FIG. 14, and it is found out that the relative detection-light quantity can be greater than 100%, the strict relative detection-light quantity can be greater than 100%, and the crosstalk can be 0%, and therefore a condition for high sensitivity and low crosstalk can be obtained. A size of the multicolor detection apparatus can be smaller than a volume (414 mm$^2$) of a rectangular parallelepiped which is specified by a total width AW=3 mm of the emission-point array, a width of 13.8 mm in an optical axis direction of the condensing lens 2, and a width of 10 mm in a vertical direction with respect to the optical axis of the condensing lens 2 and an array direction of the emission-point array. That is, a size of the fluorescence detection apparatus can be reduced to 1/3,900 of the size in the case disclosed in PTL 1. Further, since all of the optical elements to be used are fine, a large cost can be reduced.

EXAMPLE 4

According to the examples described above, especially when the multicolor detection apparatus using the dichroic-mirror array is miniaturized, it is important but difficult to achieve both expansion of the aperture width W and reduction of the optical path length g, because both share a trade-off relation therebetween. Adjustments of the array interval x and the stepwise shiftss y and z of the dichroic-mirror array, all of which are illustrated in Example 3, are effective ways for solving the above-described problem. In Example 4, the array interval and the stepwise shift arrangement are generalized, and then a general solution for achieving both the expansion of the aperture width W and the reduction of the optical path length g is derived. A main characteristic of the present invention in the dichroic mirror arrangement is that the thickness β of the dichroic mirrors is taken into consideration. In the related art, the size of the dichroic mirrors (α and γ) is sufficiently large. Accordingly, the thickness β is not required to be taken into consideration. Meanwhile, when the dichroic mirrors are miniaturized, it is important to arrange them taking the thickness β into consideration. Particularly, when each dichroic mirror is installed not in the air but inside a glass material, assuming the thickness β as β=0 does not cause any drawback.

FIG. 16 is a cross-sectional diagram schematically illustrating the multicolor detection apparatus. The cross-sectional diagram includes an optical axis of one condensing lens 2 and the paper plane thereof is perpendicular to the array direction of the condensing-lens array 8. Further, FIG. 16 illustrates a configuration of a multicolor detection apparatus, where the aperture width W is set to the maximum value, and the optical path length g is set to the minimum value, when the width aand the thickness β of each of the dichroic mirrors are provided. The condensing lens 2, the longpass filter 10, and the two-dimensional sensor 30 illustrated in FIG. 15 are omitted.

As illustrated in FIG. 16, a light beam 70 with a diameter of the aperture width W, which is incident from the top to the bottom, is repeatedly reflected by and transmitted through the dichroic mirrors M(1), M(2), M(3) . . . and M(N) to obtain light beams F(1), F(2), F(3) . . . , and F(N) which are emitted from the top to the bottom. The number of the dichroic mirrors, that is, the divided number of the light beams 70 is four in the example in FIG. 16. However, this example generalizes the number as N (N≥2). Further, the Nth dichroic mirror M(N) may be replaced with a total reflection mirror. Hereinabove, as illustrated in FIGS. 12 to 15, the optical path length g of the emission detection apparatus is defined as the the maximum optical path length from the condensing lens 2 to the sensor 30. Hereinafter, as illustrated in FIG. 16, an optical path length L of the dichroic-mirror array as a part of the optical path length g is defined as an optical path length from a position having the same height as the top end of the dichroic-mirror array (the upper end of the dichroic mirror M(N)) on the optical axis of the light beam 70 to a position having the same height as the lowest end (of the dichroic-mirror array the lower end of the dichroic mirror M(1)) on an optical axis of the light beam F(N) in the optical path of the maximum length (the optical path from the light beam 70 to the light beam F(N)).

is composed of a quartz substrate, on a lower right front surface of which a multilayer or the monolayer film is formed. Each of the quartz substrates has a width of α=5 mm, a thickness of β=1 mm, and a depth of γ=5 mm.

Each dichroic mirror is composed of a transparent substrate having a refractive index $n_0$ on a one front surface of which an optical film is formed and is disposed in the air at an interval x. A direction of a normal vector of each dichroic mirror is defined as a direction from a lower right front surface to an upper left front surface of each dichroic mirror in FIG. 16. Each dichroic mirror is set to be inclined in such a manner that each normal vector is inclined by an angle $\theta_0$ is (0≤$\theta_0$≤90°) with respect to a direction opposite to a propagating direction of the light beam 70 (direction from the bottom to the top in FIG. 16). Although $\theta_0$=45° in FIG. 16, $\theta_0$ is set to any angle of 0°≤$\theta_0$≤90° in this example. As described above, the dichroic mirrors M(1) to M(N) are arrayed in approximately parallel to each other, and arrayed at approximately equal intervals. Further, the lower end of the dichroic mirror M(2) is disposed to be shifted to an upper side by y, that is, disposed to be shifted to an opposite direction to the propagating direction of the light beam F(1) by y, with respect to the lower end of the dichro dichroic mirror M(1). Further, the lower end of the dichroic mirror M(3) is disposed to be shifted to an upper side by z, that is, disposed to be shifted to an opposite direction to the propagating direction of the light beam F(2) by z, with respect to the lower end of the dichroic mirror M(2). In the same manner, when 3≤n≤N, the lower end of the dichroic mirror M(n) is disposed to be shifted to an upper side by z, that is, disposed to be shifted to an opposite direction to the propagating direction of the light beam F(n−1) by z, with respect to the lower end of the dichroic mirror M(n−1).

At this time, the incident angle of the light beam on an incident surface (upper left front surface) of the dichroic mirror M (1) is $\theta_0$, and the refraction angle $\theta_1$ of the light beam on the incident surface of the dichroic mirror M (1) is represented as follows.

$$\theta_1 = \sin^{-1}(1/n_0 * \sin\theta_0) \quad \text{[Equation 19]}$$

On the other hand, the incident angle of the light beam on an incident surface (lower right front surface) of each of the di chroicmirrors M(2) to M(N) is 90°−$\theta_0$, respectively. Then, the refraction angle $\theta_2$ of the light beam on the incident surface of each of the dichroic mirrors M(2) to M(N) is represented as follows.

$$\theta_2 = \sin^{-1}(1/n_0 * \sin(90° - \theta_0)) \quad \text{[Equation 20]}$$

The right end of the light beam 70 is illustrated as a light-beam right end 66 with a dashed line, a left end thereof is illustrated as a light-beam left end 67 with a dashed-dotted line. The dashed line and the dashed-dotted line are traced and extended to the light beams F(1), F(2), F(3), . . . , and F(N).

Hereinafter, two conditions for the best mode which maximizes the aperture width W and minimizesg the optical path length L will be described with reference to FIG. 16. The first condition is that the light-beam right end 66 passes through or passes the proximity of the left end corners 69, which are illustrated by triangle marks in FIG. 16, of the dichroic mirrors M(1), M(2), . . . , and M(N−1). The second condition is that the light-beam left end 67 passes through or passes the proximity of the lower end corner 68, which is illustrated by a circular mark in FIG. 16, of the dichroic mirror M(1), and the left end corners 69 of the dichroic mirror M(2), . . . , and M(N−1). According to the above-mentioned conditions, the following relational Equations are derived from geometrical relations in FIG. 16.

First, the interval x between the dichroic mirrors M(1) to M(N) is described in the best mode as follows.

$$x = x_0 = \cos\theta_0 * \alpha + \sin\theta_0 * \beta \quad \text{[Equation 21]}$$

Further, the aperture width W is represented in the best mode as follows.

$$W = W_0 = a_w * \alpha + b_w * \beta \quad \text{[Equation 22]}$$

Here, Equations 23 and 24 are represented as follows.

$$a_W = \cos\theta_0 \quad \text{[Equation 23]}$$

$$b_W = -\cos\theta_0 * \tan\theta_1 \quad \text{[Equation 24]}$$

Further, the optical path length L is represented in the best mode as follows.

$$L = L_0 = a_L * \alpha + b_L * \beta \quad \text{[Equation 25]}$$

Here, Equations 26 and 27 are represented as below.

$$a_L = (N-1) * \cos\theta_0 + \sin\theta_0 \quad \text{[Equation 26]}$$

$$b_L = (N-2)/\cos\theta_0 * (2*\sin(90° - \theta_0 - \theta_2) + 1 - \sin(\theta_0 + \theta_2)) + (N-2)*\sin\theta_0 + 2*\cos\theta_0 \quad \text{[Equation 27]}$$

Meanwhile, the stepwise shifts y and z of the respective dichroic mirrors M(1) to M(N) are represented in the best mode as follows.

$$y = y_0 = \cos\theta_0 * \beta \quad \text{[Equation 28]}$$

$$z = z_0 = \sin(90° - \theta_0 - \theta_2)/\cos\theta_2 * \beta \quad \text{[Equation 29]}$$

As described above, all of the $x_0$, $W_0$, $L_0$, $y_0$, and $z_0$ are associated with α and β.

Basically, the above-described α, β, $n_0$, $\theta_0$, x and z are respectively equal among the dichroic mirrors and the total reflection mirror, but are not necessarily required to be equal. In this case, α, β, $n_0$, $\theta_0$, x and z are respectively average values for a plurality of the dichroic mirrors.

α, β, and x for obtaining a minimum aperture width $W_{min}$ can be derived by solving what is described above. $W_0 \geq W_{min}$ and Equation (22) give Equation (30) as follows (here, an equal sign gives the best mode).

$$\alpha \geq -b_W/a_W * \beta + 1/a_W * W_{min} \quad \text{[Equation 30]}$$

Similarly, Equation (21) gives Equation (31) as follows (here, an equal sign gives the best mode).

$$x \geq (\sin\theta_0 - b_W/a_W * \cos\theta_0) * \beta + 1/a_W * \cos\theta_0 * W_{min} \quad \text{[Equation 31]}$$

α, β, and x for obtaining a maximum optical path length $L_{max}$ can be derived in the same manner. Equation (25) gives Equation (32) as follows (here, an equal sign gives the best mode).

$$\alpha \leq -b_L/a_L * \beta + 1/a_L * L_{max} \quad \text{[Equation 32]}$$

Equation (21) gives Equation (33) as follows (here, an equal sign gives the best mode).

$$x \leq (\sin\theta_0 - b_L/a_L * \cos\theta_0) * \beta + 1/a_L * \cos\theta_0 * L_{max} \quad \text{[Equation 33]}$$

Basically, the above-mentioned $W_{min}$ and $L_{max}$ are respectively equal among the emission points and the condensing lenses, but are not necessarily required to be equal. In this case, $W_{min}$ and $L_{max}$ are respectively average values for a plurality of the emission points and the condensing lenses.

FIG. 17 illustrates a range of satisfying Equations (31) and (33) with a horizontal axis β and a vertical axis x, for example, in a case where N=4, $n_0$=1.46, and $\theta_0$=45°. The parameters are set as $W_{min}$=0.5, 1, 2, 3 and 4 mm, $L_{max}$=5, 10, 20, 30 and 40 mm. Each ↑ indicates a range of an upper side above a straight line and each ↓ indicates a range of a lower side below a straight line. For example, it is possible to select any β and x in a range of the upper side above the straight line of ↑$W_{min}$=0.5 and a range of the lower side below the straight line of ↓$L_{max}$=20 in FIG. 17 to achieve $W_{min}$=0.5 mm and $L_{max}$=20 mm.

Meanwhile, for given the diameter d of the emission points and the interval p of the emission-point array, when the focal distance f of the condensing lenses and the optical path length g between each condensing lens and the sensor are selected such that they satisfy the high sensitivity conditions of any one of Equations (3) to (7) or (8) to (12), and when Equations (31) and (33) are satisfied by $W_{min}$=d' and $L_{max}$=g, a compact multicolor detection apparatus using the dichroic-mirror array satisfying the high sensitivity conditions can be configured. Here, d'=(g-f)/f*d is represented according to Equation (2). In the same manner, for given the diameter d of the emission points and the interval p of the emission-point array, when the focal distance f of the condensing lenses and the optical path length g between each condensing lens and the sensor are selected such that they satisfy the low crosstalk conditions of any one of Equations (16) to (18), and when Equations (31) and (33) are satisfied by $W_{min}$=d' and $L_{max}$=g, a compact multicolor detection apparatus using the dichroic-mirror array satisfying the low crosstalk conditions can be configured. Further, when the focal distance f of the condensing lenses and the optical path length g between each condensing lens and the sensor are selected such that they satisfy the high sensitivity conditions of any one of Equations (3) to (7) or (8) to (12), and satisfy the low crosstalk conditions of any one of Equations (16) to (18), and Equations (31) and (33) are satisfied by $W_{min}$=d' and $L_{max}$=g, a compact multicolor detection apparatus using the dichroic-mirror array satisfying the high sensitivity conditions and the low crosstalk conditions can be configured.

For example, in case of d=0.05 mm, p=1 mm, f=1.5 mm, D=1 mm, g=29 mm according to Example 1, all of Equations (4), (9), (18), (31), and (33) are satisfied when N=4, $n_0$=1.46, $\theta_0$=45°, β=1 mm, x=5 mm, and it is found out that the compact multicolor detection device using the dichroic mirrors having the high sensitivity and the low crosstalk can be accomplished.

Next, the interval x between the respective dichroic mirrors M(1) to M(N) will be described in detail. In the best mode, it may be most desirable to set $x_0$ calculated by Equation (21) as described above. Next, it will be described in detail hereinbelow how much deviation from the best mode may be allowed to obtain the effect. A solid line illustrated in FIG. 18 is a result of calculating a relation between the interval x and the aperture width W in the dichroic-mirror array composed of the two dichroic mirrors (N=2), that is, the dichroic mirrors 17 and 18 in FIG. 15. Generally, there exists a possibility that the aperture width W becomes smaller than the above-mentioned result as the total number N of the dichroic mirrors of the dichroic-mirror array increases. However, in this case, the dichroic-mirror array with N=2 is evaluated as an index. FIG. 15 illustrates a condition of x=$x_0$=2.5 mm calculated under Equation (21) when set as $\theta_0$=45° and β=1 mm. In this case, as illustrated in FIG. 18, the aperture width becomes maximum as W=1.3 mm. In the case of x<$x_0$, W decreases with |x−$x_0$|, and W=0 mm at x=1.6 mm. On the other hand, in the case of x>$x_0$, W is constant at W=1.3 mm. Meanwhile, a broken line illustrated in FIG. 18 illustrates a relation between the interval x and a variation ΔL of the optical path length L in FIG. 15. Here, ΔL is displayed so as to be ΔL=0 mm at x=$x_0$=2.5 mm, ΔL=0 mm is displayed and so as to be the same height as that of W=1.3 mm. Further, scales of a vertical axis for W (left side) and a vertical axis for ΔL (right side) are equalized, and the vertical axis for ΔL is vertically inverted. Generally, there exists a possibility that ΔL becomes greater than the above-mentioned result as the total number N of dichroic mirrors of the dichroic-mirror array increase. However, in this case, the dichroic-mirror array with N=2 is evaluated as an index. Further, ΔL increases in proportion to x, needless to say.

In FIG. 18, both an increasing rate of W with respect to x when 1.6 mm≤x≤2.5 mm, and an increasing rate of ΔL with respect to x when 2.5 mm≤x are equal, and inclinations of the both lines are approximately 1. In other words, it can be seen that their performances deteriorate in proportion to |x−$x_0$|. In contrast, in the related art, β is not taken into consideration, which corresponds to β=0 mm. At this time, in the case where β=0 mm, x=$x_0$=1.8 mm under Equation (21), and then W=0.4 mm as shown in FIG. 18. Accordingly, it is found out that it is desirable to be set as 1.8 mm≤x≤3.2 mm to obtain performance equal to or better than that of the related art. Generally, the array interval x between the dichroic mirrors M(n) and M(n−1) in FIG. 16, where 2≤n≤N, is represented by the following equation.

$$\cos\theta_0 * \alpha \leq x \leq \cos\theta_0 * \alpha + 2 * \sin\theta_0 * \beta \quad \text{[Equation 34]}$$

This may enlarge the aperture width W, and reduce the optical path length L.

Next, the stepwise shifts y and z of the respective dichroic mirrors M(1) to M(N) will be described in detail. As described above, in the best mode, it maybe most desirable to set $Y_0$ and $Z_0$ calculated by Equations (28) and (29). Next, it will be described in detail how much deviation from the best mode is allowed to obtain the effect.

FIG. 19(a) is a result of calculating a relation between the stepwise shift y and the aperture width W in the dichroic-mirror array composed of the two dichroic mirrors (N=2), that is, the dichroic mirrors 17 and 18 in FIG. 15. Generally, there exists a possibility that the aperture width W becomes smaller than the above-mentioned result as the total number N of the dichroic mirrors increases. However, in this case, the dichroic-mirror array with N=2 is evaluated as an index. FIG. 15 illustrates a condition of $y=y_0=0.7$ mm calculated under Equation (28) when set as $\theta_0=45°$ and $\beta=1$ mm. In this case, as illustrated in FIG. 19(a), the aperture width becomes maximum as W=1.3 mm. Further, W decreases in proportion to $|y-y_0|$. W=0.6 mm at y=0 mm and 1.4 mm, and W=0 mm at y=−0.7 and 2.1 mm. Here, a negative y indicates the stepwise shift in a direction opposite to that in FIG. 15. Therefore, it is found out that the effect of the stepwise shift is obtained by setting y to 0 mm≤y≤1.4 mm.

In the same manner, FIG. 19(b) is a result of calculating a relation between the stepwise shift z and the aperture width W in the dichroic-mirror array composed of the two dichroic mirrors (N=2), that is, the dichroic mirrors 18 and 19 in FIG. 15. FIG. 15 illustrates a condition of $z=z_0=0.3$ mm calculated under Equation (29) when set as $\theta_0=45°$ and $\beta=1$ mm. In this case, as illustrated in FIG. 19(b), the aperture width becomes maximum as W=1.3 mm. Further, W decreases in proportion to $|z-z_0|$. W=1 mm at z=0 mm and 0.6 mm, and W=0 mm at z=−1.1 and 1.7 mm. Here, a negative z indicates the stepwise shift in a direction opposite to that in FIG. 15. Therefore, it is found out that the effect of the stepwise shift is obtained by setting z to 0 mm≤z≤0.6 mm. What is described above is generalized as described hereinafter. In FIG. 16, a divided-light-beam-propagation-side end of the dichroic mirror M(2) is shifted to a side opposite to a divided-light-beam-propagation direction by y with respect to a divided-light-beam-propagation-side end of the dichroic mirror M(1). Then, y is represented by the following equation (35).

$$0 \leq y \leq 2*\cos\theta_0*\beta \qquad \text{[Equation 35]}$$

According to Equation (35), the aperture width W may be enlarged, and the optical path length L may be reduced.

Further, in the case of 3≤n≤N, and a divided-light-beam-propagation-side end of the dichroic mirror M(n) is shifted to a side opposite to a divided-light-beam-propagation direction by z with respect to a divided-light-beam-propagation-side of the dichroic mirror M(n−1). Then, z is represented by the following equation (36).

$$0 \leq z \leq 2*\sin(90°-\theta_0-\theta_2)/\cos\theta_2*\beta \qquad \text{[Equation 36]}$$

According to Equation (36), the aperture width W may be enlarged, and the optical path length L may be reduced.

The above description is mainly directed at the configuration in which the optical axis of each condensing lens and the propagation direction of the divided light beams are parallel to each other as shown in FIGS. 15 and 16. Meanwhile, when the optical axis of each condensing lens and the propagation direction of the divided light beams are vertical as illustrated in FIG. 12, a divided-light-beam-propagation-side end of the dichroic mirror M(n) is shifted to a side opposite to a divided-light-beam-propagation direction by z as shown by Equation (36) with respect to a divided-light-beam-propagation-side of the dichroic mirror M(n−1), where 2≤n≤N. In so doing, the aperture width W may be enlarged, and the optical path length L may be reduced.

EXAMPLE 5

In Examples 3 and 4, the expansion of the aperture width W and the reduction of the optical path length L of the dichroic-mirror array are accomplished by the stepwise shift arrangement of a plurality of dichroic mirrors. In the example, proposed herein is a way for expanding the aperture width W and reducing the optical path length L when the stepwise shift arrangement is not performed, that is, when a plurality of dichroic mirrors are disposed on the same plane, more specifically, when the divided-light-beam-propagation-side ends of the respective dichroic mirrors are disposed on the same plane.

FIG. 14 according to Example 3 illustrates the result when $\theta_0=45°$, while FIG. 20 illustrates the result when $\theta_0=50°$. The other conditions are equal for FIG. 14 and FIG. 20, and in both cases of FIGS. 14 and 20, the dichroic mirrors 17 to 20 are disposed on the same plane. Nevertheless, it is clearly found out that the aperture width is only W=0.03 mm in FIG. 14, while the aperture width is significantly expanded to W=0.9 mm in FIG. 20. Here, the maximum optical path length does not change in both FIGS. 14 and 20, and is set as L=19 mm. Accordingly, similar to FIG. 14, the image magnification becomes m=11.7 and the diameter of each emission point image becomes d'=0.88 mm, and Equation (18) is satisfied as well as Equations (4) and (9). Therefore, the relative detection-light quantity becomes greater than 100%, the strict relative detection-light quantity becomes greater than 100%, the crosstalk becomes equal to 0%, and therefore the high sensitivity and the low crosstalk conditions are both achieved.

Hereinafter, a reason why the above-mentioned effects are achieved will be described. As illustrated in FIG. 14, when set as $\theta_0=45°$, the light beam horizontally propagates in the space between different dichroic mirrors. Meanwhile, the light beam propagates to the upper left direction in the respective dichroic mirrors. Therefore, the light beam shifts to the upper direction in a stepwise manner, as the light beam passes through the dichroic mirrors. Due to this, the aperture width W is limited. On the other hand, when set as $\theta_0=50°≥45°$ in FIG. 20, the light beam propagates to a lower left direction in the space between different dichroic mirrors. Meanwhile, since the light beam propagates to the upper left direction in the respective dichroic mirrors. Because both propagations are canceled out, the light beam shift to an up-or-down direction is suppressed when the light beam passes through the dichroic mirrors, thereby expanding the aperture width W. Therefore, it may be desirable that $\theta_0$ is set to be greater than 45°, and then, an optimum value for maximizing the aperture width W exists.

FIG. 21 illustrates a result of calculating W when $\theta_0$ is changed under the conditions illustrated in FIGS. 14 and 20. It is found out that W increases with $\theta_0$ from $\theta_0=45°$, and W becomes a maximum value of 0.92 mm when $\theta_0=52°$. Then, W decreases with $\theta_0$ from $\theta_0=52°$, and to W becomes approximately zero when $\theta_0=57°$. That is, it is found that W can be expanded when set as $45°≤\theta_0≤57°$.

Hereinafter, what is described above will be generalized. In the same manner as that of FIG. 16, following Equations are derived from geometrical relations in FIG. 20. The refraction angle $\theta_1$ of the light beam on the incident surface of the dichroic mirror M(1) is represented by Equation (19), and the refraction angle $\theta_2$ of the light beam on the incident surfaces of the dichroic mirrors M(2) to M(N−1) is represented by the equation (20). A shift distance S↓ of the light beam in the lower direction when the light beam propagates to the lower left direction in the space between different dichroic mirrors is represented as follows.

$$S\downarrow = \tan(2*\theta_0-90°)*\tan\theta_0/(\tan\theta_0-\tan(2*\theta_0-90°))*(x-\beta/\cos(90°-\theta_0)) \qquad \text{[Equation 37]}$$

Meanwhile, a shift distance ST of the light beam in the upper direction when the light beam propagates to the upper left direction in the respective dichroic mirrors is represented as follows.

$$S\uparrow 1/\cos\theta_2 * \beta * \sin(90°-\theta_0-\theta_2) \quad \text{[Equation 38]}$$

Here, β indicates the thickness of each dichroic mirror and x indicates the interval between the dichroic mirrors. It may be most desirable to set $S\downarrow=S\uparrow$ in order to cancel out $S\downarrow$ and $S\uparrow$ as illustrated in FIG. 20. Here, $\theta_0$ in the best mode is specified as $\theta_0$(BM).

When β=1 mm and x=2.5 mm, which are conditions in FIG. 20, Equations (37) and (38) give $\theta_0$(BM)=50°. That is, the configuration illustrated in FIG. 20 is the configuration in the best mode. However, according to FIG. 21, W becomes maximum at $\theta_0$=52°, which is larger by 2° than the above-described $\theta_0$(BM). This means that W can be slightly larger if $\theta_0$ is slightly larger than $\theta_0$(BM), that is, $S\downarrow$ is set to be slightly larger than $S\uparrow$ to let the light beam slightly propagate to the lower left direction.

As described above, a condition for significantly expanding W with respect to $\theta_0$=45°, which is a reference condition of the related art, is represented as follows.

$$45°\leq\theta_0\leq 2*\theta_0(BM)-45° \quad \text{[Equation 39]}$$

Further, in consideration of the deviation of 2° described above, a more accurate condition is represented as follows.

$$45°\leq\theta_0\leq 2*\theta_0(BM)-43° \quad \text{[Equation 40]}$$

EXAMPLE 6

FIG. 22 is a schematic diagram illustrating the emission detection apparatus when size of the emission points is relatively large in the configuration of FIG. 6. The diameter of each emission point 71 is set as d=0.5 mm, which is larger by one digit than that of Example 1, and the interval is set as p=1 mm. Each emission point 71 is respectively constituted of a cubic reaction cell of 0.5 mm×0.5 mm×0.5 mm, and chemi-luminescence is generated by an internal chemical reaction. Temporal changes of the wavelength of the chemi-luminescence and the intensity thereof are measured for every emission point 71, thereby analyzing samples introduced to respective reaction cells. The focal distance and the effective diameter of each condensing lens 2 are respectively set as f=1 mm and D=1 mm, the interval of condensing lenses 2 is set as p=1 mm, and the optical distance between each condensing lens 2 and the two-dimensional color sensor 11 is set as g=10 mm. Not only the array directions of the emission points 71 and the condensing lenses 2 may be lateral as illustrated in FIG. 22(a), but also they may be vertical to the paper plane of FIG. 22(a). In the example, since an excitation light source is not required, the longpass filter 10 illustrated in FIG. 6 is omitted.

As illustrated in FIG. 22(a), when each emission point 71 is imaged on a sensor surface of the two-dimensional color sensor 11, m is set as m=9 according to Equation (1) and d' is set as d'=4.5 mm according to Equation (2). In this case, Equations (6) and (10) are satisfied, and therefore the relative detection-light quantity becomes greater than 400%, and the strict relative-detection-light quantity becomes greater than 200%. On the other hand, as shown by the light beam 9 in FIG. 22(a), the crosstalk between different emission points 71 is significantly large, and any one of Equations (16) to (18) is not satisfied.

As illustrated in FIG. 22(b), a pinhole array 73 having respective pinholes 72 is disposed so that each pinhole 72 is located between each emission point 71 and the corresponding condensing lens 2. The diameter $d_0$ of each pinhole 72 is set as $d_0 \leq d$, here, $d_0$=0.1 mm. An interval between the respective pinholes is set as p=1 mm. Not only the array direction of the pinholes may be lateral as illustrated in FIG. 22(b), but also they may be vertical to the paper surface in FIG. 22(a). Here, the pinhole 72 is considered as the emission point instead of the emission point 71. The pinholes 72 are just focused on a sensor surface of the two-dimensional color sensor 11 to form pinhole images 74 as illustrated in FIG. 22(b). The diameter of each pinhole image 74 is set as d'=0.9 mm under Equation (2). In this case, because Equation (18) is satisfied, the crosstalk can be set as 0%. In the same manner as that of FIG. 22(a), because Equations (6) and (10) are satisfied, the relative detection-light quantity becomes greater than 400%, and the strict relative-detection-light quantity becomes greater than 200%. However, the values described above are set based upon a total light quantity passing through the pinhole 72, and are smaller than those based upon a total light quantity emitted from the emission point 71 in FIG. 22(a).

FIG. 23 is a schematic diagram illustrating another example of applying a detection apparatus which is the same as that of FIG. 22(b). As illustrated in FIG. 23(a), the diameter of each emission point 75 is set as d=0.01 mm, and an interval of emission points 75 is set as p'=0.1 mm. Further, a focal distance and an effective diameter of each condensing lens 2 is set as f=1 mm and D=1 mm, and an interval of emission points 75 is set as p=1. In other words, unlike the examples described above, the interval between the emission points and the interval between the condensing lenses are different from each other. The example shows a case when set as p'<p. The emission points 75 and the condensing lenses 2 may be arrayed at equal intervals in a vertical direction on a paper surface in FIG. 23(a). When each emission point 75 is just focused on a sensor surface of the two-dimensional color sensor 11, since lights emitted from a plurality of the emission points 75 in a wider range than the case of FIG. 22(a) is condensed by the respective condensing lens 2, the crosstalk further increases.

Next, as illustrated in FIG. 23(b), the pinhole array 73 having respective pinholes 72 is disposed, such that each pinhole 72 is disposed between each emission point 75 and the corresponding condensing lens 2. The pinholes 72 are respectively disposed in alignment with the corresponding condensing lenses 2. The diameter $d_0$ of each pinhole 72 is set as $d_0 \leq d$, and, here, $d_0$=0.1 mm. An interval between the respective pinholes is set as p=1 mm. The array direction of the pinholes may also be vertical to a paper plane in FIG. 23(b). Here, each emission point 75 and each pinhole 72 are collectively just focused on a sensor surface of the two-dimensional color sensor 11 to form an emission point image 76 and a pinhole image 74 by sufficiently arranging the emission-point array and the pinhole array 73 close to each other. Because the diameter of the pinhole image 74 is set as 0.9 mm under Equation (2), the crosstalk between the different pinhole images 74 is set as 0%, which is the same as that of FIG. 22(b). On the other hand, each condensing lens 2 condenses lights emitted from plural (in average, two) emission points 75 via each pinhole 72 to form their emission point images 76 inside each pinhole image 74 on the sensor surface of the two-dimensional color sensor 11. Since the diameter of each emission point image 76 is set as 0.09 mm and the interval is set as 0.9 mm, the crosstalk does not exist between the different emission point images 76.

FIG. 23(b) illustrates a configuration achieving highly sensitive and low crosstalk multicolor detection of the lights emitted from the emission points arrayed at intervals narrower than those of the condensing lenses. However, this configuration can detect only a part of the emission points among a plurality of the emission points. In the case of FIG. 23(b), only two emission points among ten emission points are detected on average. However, all of the emission points can be detected by sequentially shifting a relative position of the detection apparatus after the pinhole array 73 to a emission-point array in an arrow direction illustrated in FIG. 23(b), that is, by scanning emission points to be detected among a plurality of the emission points.

As described above, the multicolor detection apparatus using the two-dimensional color sensor is herein used. Alternatively, a multicolor detection apparatus using a two-dimensional monochrome sensor instead of adopting the two-dimensional color sensor can be used as well. The multicolor detection apparatus using the dichroic-mirror array may be used as illustrated in FIG. 7.

FIG. 24(a) is a schematic diagram illustrating examples of a multicolor detection apparatus using a dichroic-mirror array in the example, and is a configuration achieved by combining FIG. 7(b) and FIG. 23(a). In FIG. 24(a), the light beams 21, 22, 23 and 24 respectively have different optical path lengths. Accordingly, if any one of the corresponding emission point images 25, 26, 27, and 28 is in focus on the sensor surface of the two-dimensional sensor 30, other emission point images are out of focus or blurred on the sensor surface. As shown in FIG. 24, when one emission point 75 is condensed by one condensing lens 2 and four emission point images 25, 26, 27, and 28 are obtained, the above-described blur state does not result in crosstalk. On the other hand, when a plurality of the emission points 75 are condensed by one condensing lens 2 as shown in FIG. 23, and the divided four emission point images 25, 26, 27, and 28 are obtained with respect to each emission point, a plurality of the emission point images 76 in the pinhole image 74 are overlapped with each other due to the above-described blur sate. Therefore the above-described blur sate results in the crosstalk.

As illustrated in FIG. 24(b), optical path length adjusting elements 77, 78 and 79 respectively having different lengths are inserted on optical paths of the light beams 21, 22, and 23, and the optical path lengths defined by optical distances between the condensing lens 2 and the two-dimensional sensor 30 as for the light beams 21, 22, 23 and 24 are adjusted to be approximately equal to each other. The optical path length adjusting elements are constituted of a transparent material, a refractive index of which is greater than 1. For example, in the case of a material having a refractive index of 2, even though the same distance is spatially represented, the material has an optical distance 2 times longer than that in the air. According to the constitution, the emission point images 25, 26, 27, and 28 can be simultaneously in focus on the sensor surface of the two-dimensional sensor 30, thereby having an effect of preventing the blur state and the crosstalk caused by the blur state from occurring.

As described above, it is possible to detect the emission point-array where emission points to be detected are arrayed at approximately equal intervals. Additionally, it is also possible to detect any emission distribution with one-dimensional, two-dimensional, or three-dimensional state. Further, it is also possible to reconstruct an original emission distribution from the detection result by an imaging process and the emission detection apparatus which is the same as that of FIG. 23(b). FIG. 25 schematically illustrates examples of the imaging processes.

As illustrated in FIG. 25(a), a emission distribution 80 is distributed in a two-dimensional shape. Here, a case in which the emission distribution 80 draws a character "a" is illustrated as an example. Further, the pinhole array 73 is disposed in parallel to the emission distribution 80 and disposed to be close thereto. FIG. 25(a) schematically illustrates a positional relation and a magnitude relation between a plurality of the pinholes 72 of the pinhole array 73 and the emission distribution 80. Here, 3×3=9 pinholes 72 are arrayed two-dimensionally at equal intervals. Since the emission distribution 80 and each pinhole 72 are disposed to be sufficiently close to each other, light emitted from a overlapping portion of each pinhole 72 and the emission distribution 80 in FIG. 25(a) is detected through each pinhole 72 by the emission detection apparatus which is the same as that of FIG. 23(b).

FIG. 25(b) illustrates 9 pinhole images 74 which are images of 9 pinholes 72 on the two-dimensional color sensor 11, and 9 emission distribution partial images 81 which are partial images of the emission distribution 80 detected through 9 pinholes 72. In the same manner as those of the examples described above, while the image of each pinhole 72 is enlarged, since an interval of the pinholes 72 and an interval of the pinhole images 74 are equal to each other, the interval of the neighboring pinhole images 74 becomes narrowed as illustrated in FIG. 25(b), however, mutual crosstalk is set as 0%. Since each emission distribution partial image 81 is accommodated in each corresponding pinhole image 74, the crosstalk therebetween is also 0%.

FIG. 25(c) illustrates that the relative position of the pinhole array 73 to the emission distribution 80 is shifted in the lateral direction compared with that in FIG. 25(a). Each pinhole 72 is overlapped with a different part of the emission distribution 80 from that in FIG. 25(a). Light emitted from each overlapped part is respectively imaged and detected as illustrated in FIG. 25(d). Accordingly, the relative position of the pinhole array 73 to the emission distribution 80is sequentially slid (that is, slid in order) in the lateral and longitudinal directions, and the above imaging is repeated, and thereby the imaging of a whole image of the emission distribution is made possible. At this time, when the relative positions of the two-dimensional color sensor 11 to the emission distribution 80 is fixed, the whole image of the emission distribution 80 can be obtained without performing an image processing.

EXAMPLE 7

One of the drawbacks in implementing the invention is to accurately and simply align the positions of each emission point and each condensing lens. The example illustrates a way for realizing the above-mentioned alignment of the positions thereof with respect to a plurality of the capillaries.

FIG. 26 is a cross-sectional diagram schematically illustrating configuration examples of a device 86 in which a plurality of the capillaries 49, a V-groove array for arraying the plurality of capillaries 49, and the condensing-lens array 8 are integrated with each other. FIG. 26(a) illustrates a cross section perpendicular to a longitudinal axis of each capillary 49 at an irradiation position of the laser beam 54; FIG. 26(b) illustrates a cross section perpendicular to the longitudinal axis of each capillary 49 at a position other than the irradiation position of the laser beam 54; and FIG. 26(c) illustrates a cross section including a longitudinal axis of any single capillary 49. FIG. 26(a) is a cross section taken along the line A-A of FIG. 26(c), and FIG. 26(b) is a cross section taken along the line B-B of FIG. 26(c).

The device 86 illustrated in FIG. 26 includes the capillary array including a plurality of the capillaries 49, and a sub-device 85. The sub-device 85 is integrated with a V-groove array device 84 including the V-groove array in which a plurality of V-grooves 82 are arrayed at an interval p; and a condensing-lens array device 83 including the condensing-lens array 8 in which a plurality of the condensing lenses 2 are arrayed at an interval p. In FIG. 26(a), the center axes of each emission point 1, each V-groove 82, and each condensing lens 2 are set to coincide with each other. The plurality of capillaries 49 can be simply arrayed on the same plane at the predetermined interval p by pressing the plurality of capillaries 49 against the V-grooves 82. Further, a structure of the sub-device 85 is adjusted in such a manner that each emission point 1 is the irradiation position of the laser beam 54 of each capillary 49 and distance between each emission point 1 and each condensing lens 2 is desirable. Accordingly, the light emitted from the emission point 1 is condensed by the condensing lens 2 as desired.

As illustrated in FIG. 26(a), the condensing lens 2 of the sub-device 85 exists and the V-groove 82 does not exist on a cross section of the capillary 49 at the emission point 1. On the other hand, as illustrated in FIG. 26(b), the condensing lens 2 of the sub-device 83 does not exist and the V groove 82 exists on a cross-section of the capillary 49 at opposite sides of the emission point 1. FIG. 26(c) illustrates a cross section in a longitudinal axis direction of the capillary 49, the condensing lens 2 exists at a center of the sub-device 85, and the V-grooves 82 exist at opposite sides of the condensing lens 2. According to the configuration, it is advantageously possible not only to allow the capillary 49 to be aligned with high accuracy by the V-groove 82, but also to prevent the detection of the light emitted from the emission point 1 from being disturbed by the V-groove 82. When the sub-devices 85 as described above is prepared, highly accurate alignment between the respective emission points 1 and the respective condensing lenses 2 can be simply performed only by pressing the plurality of capillaries 49 against the respective V-grooves 82.

The example can be combined with any one of the examples described above. The sub-device 85, in which the V-groove array device 84 and the condensing-lens array device 83 are integrated with each other, can be integrally molded by a processing method such as injection molding and imprint, thereby having an effect of mass production at a low cost. Further, the V-groove array device 84 and the condensing-lens array device 83 may be separately manufactured and then coupled to each other so as to complete the sub-device 85.

The sub-device is useful even if the V-groove array is not provided. For example, a surface of the capillary-array side of the sub-device may be a plane, instead of the V-groove array. Although the array intervals of a plurality of the capillaries are required to be adjusted by another ways, it is possible to control adistance between each capillary and each condensing lens, that is, a distance between each emission point and each condensing lens by pressing each capillary against the above-mentioned plane of the sub-device. Alternatively, a structure for controlling the position of the capillary may be provided on the sub-device, even though the V-groove is not provided.

When the focal distance of each condensing lens 2 in a direction parallel to the array direction of the emission-point array is defined as f1, and the focal distance thereof in a vertical direction to the array direction of the emission-point array is defined as f2, f1 and f2 are set as $f=f1=f2$ in the examples described above. However, it may be effective to set f1 and f2 as $f1 \neq f2$. For example, according to the example, it is effective when the emission point 1 exists inside the capillary 49. Since the capillary 49 has a cylindrical shape, the capillary 49 has a lens function in an array direction of the emission-point array. However, the capillary 49 does not have the lens function in the longitudinal axis direction of each capillary 49. Accordingly, it is effective to cancel out the lens function difference depending on the direction in order to efficiently condense the light emitted from the emission point 1 by the condensing lens 2. That is, it is desirable to set f1 and f2 as $f1 \neq f2$, more specifically, $f1<f2$. What is described above can be easily achieved by making surfaces of the respective condensing lenses 2 as aspherical shapes. Further, the thickness of the lens can be reduced, and the fluorescence detection apparatus can be further miniaturized by using each condensing lens 2 as a Fresnel lens. The use of the Fresnel lens is also effective when set as $f1=f2$.

FIG. 27 illustrates a configuration in which the pinhole array 73 is added between the emission-point array and the condensing-lens array 8 in FIG. 26. More specifically, the pinhole array 73 is sandwiched between the V-groove array device 84 and the condensing-lens array device 83, and all of the configurations described above are used as the sub-device 86. The pinhole 72 illustrated in FIG. 22(b) limits a light quantity of light emitted from the emission point 71 and condensed by the condensing lens 2.emission On the other hand, in the cases of the pinhole 72 illustrated in FIG. 27, the diameter $d_0$ of each pinhole 72 is formed to be greater than the diameter d of the emission point 1 ($d_0 \geq d$), such that the pinhole 72 illustrated in FIG. 27(a) does not limit the light quantity of light emitted from the emission point 1 and condensed by the condensing lens 2emission. While the pinhole 72 of FIG. 22(b) effectively serves to reduce the diameter of the emission point 71, the pinhole 72 of FIG. 27 serves to avoid condensing light other than the light emitted from the corresponding emission point 1 by the corresponding condensing lens 2. For example, it is possible to prevent or reduce condensing and detecting of the scattered light of the laser beam 54 on an outer surface of each capillary 49 that is generated when the laser beam 54 irradiates the capillary array. Alternatively, it is possible to condense and detect the light emitted from the neighboring emission point 1 of each capillary 49. Accordingly, the light emitted from the emission point 1 can be detected with high sensitivity.

In order to prevent the unnecessary light from reaching the sensor, it is also effective to dispose a color glass filter at any position between the emission point and the sensor. The color glass filter may be combined with the pinhole or only one of the color glass filter and the pinhole may be used. Since the unnecessary light beam condensed by the condensing lens 2 propagates while being inclined to the optical axis of the condensing lens 2 (that is, being inclined to the optical axis of the light beam emitted from the emission point 1 and condensed by the condensing lens 2), it is difficult to cut off the unnecessary light beam by the longpass filter or the dichroic mirror (the reason is that the light emitted from the emission point 1 these are designed for the light beam emitted from the emission point 1 and condensed by the condensing lens 2). On the other hand, the color glass filter can accomplish equivalent filter performance even though an incident angle of the light is different, thereby having an effect of obtaining the above-mentioned effect.

FIG. 28 illustrates another configuration for achieving the same effect as that of FIG. 27. The condensing-lens array device 83, which is a component of the sub-device 85, is constituted by a transparent material such as a glass material and a resin material in the same manner as described above. Meanwhile, the V-groove array device 84 is constituted by an opaque material. The pinholes 87, which are through holes, are respectively formed at positions at the intersections of the optical axes of the condensing lenses 2 with the V-groove array device 84, such that the V-groove array device 84 serves as the pinhole array. According to the configuration, the sub-device 85 can be manufactured more simply than the case of FIG. 27.

The present invention is not limited to the examples described above, but, on the contrary, is intended to cover various modifications and equivalent arrangements included within the spirit and scope of the appended claims. For example, while the examples are described in detail in order to describe the present invention in an easily understood manner, it is understood that the invention is not limited to the disclosed configurations. Further, a part of the configuration of one example can be replaced with a configuration of another example, and the configuration of another example can be added to the configuration of one example. Further, it is possible to add, delete, and replace another configuration with respect to a part of the configuration of each example.

REFERENCE SIGNS LIST

1: emission point
2: condensing lens
3, 3': parallel light beam
4, 5: spot
7: emission point image
8: condensing-lens array
11: two-dimensional color sensor
17~20: dichroic mirror
30: two-dimensional sensor
31: transmission-type diffraction grating
33: re-condensing lens
37: two-dimensional sensor
41: wavelength-dispersed image
43: prism
45, 48: emission point image
49: capillary
53: laser light source
71: emission point
72: pinhole
74: pinhole image
75: emission point
76: emission point image
77~79: optical path length adjusting element
80: emission distribution
83: condensing-lens array device
84: V-groove array device
87: pinhole

The invention claimed is:

1. A light-emission detection apparatus comprising:
a condensing-lens array in which M condensing lenses are arranged, for individually condensing lights emitted from an emission-point array in which M emission points are arranged, to form M light beams, where M≥2;
an optical element that deflects the M light beams to form M deflected light beams;
at least one sensor on which the M deflected light beams are incident in parallel,
wherein when:
an average of effective diameters of the M emission points is d,
an average of focal lengths of the M condensing lenses is f,
an average of intervals of the M condensing lenses is p, and
an average of maximum optical path lengths between the M condensing lenses and an end surface of the optical element to which the M light beams are incident is g,
regarding the d, f, p, and g, the following relation is satisfied:

$$f \geq 1/((2*p)/(1.27*d)+1)*g.$$

2. The light-emission detection apparatus according to claim 1, wherein the following relation is satisfied:

$$f \geq 1/(p/d+1)*g.$$

3. The light-emission detection apparatus according to claim 1, wherein the following relation is satisfied:

$$f \leq 2*p.$$

4. The light-emission detection apparatus according to claim 1, wherein the following relation is satisfied:

$$f \leq p.$$

5. The light-emission detection apparatus according to claim 1, further comprising:
a pinhole array in which M pinholes are arranged while being aligned with the M condensing lenses,
wherein the M emission points are constituted by light emissions of parts of at least one emission region.

6. The light-emission detection apparatus according to claim 1, further comprising:
a capillary array in which a plurality of capillaries is aligned on a plane, and
a device that supports the capillary array,
wherein the emission-point array is generated from individual emission point from the capillary array and the condensing-lens array is integrated in the device.

7. The light-emission detection apparatus according to claim 6, further comprising:
a pinhole array arranged between the capillary array and the condensing-lens array in which M pinholes are arranged while being aligned with the M condensing lenses.

8. A light-emission detection apparatus comprising:
a condensing-lens array in which M condensing lenses are arranged, for individually condensing lights emitted from an emission-point array in which M emission points are arranged, to form M light beams, where M≥2;
a re-condensing-lens array in which M re-condensing lenses are arranged, for individually re-condensing the M light beams to form re-condensed light beams;
at least one sensor on which the M re-condensed light beams are incident in parallel,
wherein when:
an average of effective diameters of the M emission points is d,
an average of focal lengths of the M condensing lenses is f, an average of intervals of the M condensing lenses is p, and an average of maximum optical path lengths between the M condensing lenses and the M re-condensing lenses is g, regarding the d, f, p, and g, the following relation is satisfied:

$$f \geq 1/((2*p)/(1.27*d)+1)*g.$$

9. The light-emission detection apparatus according to claim 8, wherein the following relation is satisfied:

$$f \geq 1/(p/d+1)*g.$$

10. The light-emission detection apparatus according to claim 8, wherein the following relation is satisfied:

$$f \leq 2*p.$$

11. The light-emission detection apparatus according to claim 8, wherein the following relation is satisfied:

$$f \leq p.$$

12. The light-emission detection apparatus according to claim 8, further comprising:

a pinhole array in which M pinholes are arranged while being aligned with the M condensing lenses, wherein the M emission points are constituted by light emissions of parts of at least one emission region.

13. The light-emission detection apparatus according to claim 8, further comprising:

a capillary array in which a plurality of capillaries is aligned on a plane, and a device that supports the capillary array, wherein the emission-point array is generated from individual emission point from the capillary array and the condensing-lens array is integrated in the device.

14. The light-emission detection apparatus according to claim 13, further comprising:

a pinhole array arranged between the capillary array and the condensing-lens array in which M pinholes are arranged while being aligned with the M condensing lenses.

* * * * *